(12) United States Patent  (10) Patent No.: US 8,420,570 B2
Dietrich et al.  (45) Date of Patent: Apr. 16, 2013

(54) CHIRAL 3-(BENZYLSULFINYL)-5,5-DIMETHYL-4,5-DIHYDROISOXAZOLE DERIVATIVES AND 5,5-DIMETHYL-3-[(1H-PYRAZOL-4-YLMETHYL)SULFINYL]-4,5-DIHYDROISOXAZOLE DERIVATIVES, METHOD FOR THE PRODUCTION THEREOF, AND USE OF SAME AS HERBICIDES AND PLANT GROWTH REGULATIONS

(75) Inventors: Hansjoerg Dietrich, Liederbach (DE);
Arianna Martelletti, Sulzback (CH);
Christopher Hugh Rosinger, Hofheim (GB); Jan Dittgen, Frankfurt (DE);
Dieter Feucht, Eschborn (DE)

(73) Assignee: Bayer Cropscience AG, Monheim (DE)

( * ) Notice: Subject to any disclaimer, the term of this patent is extended or adjusted under 35 U.S.C. 154(b) by 105 days.

(21) Appl. No.: 12/744,042

(22) PCT Filed: Nov. 8, 2008

(86) PCT No.: PCT/EP2008/009438
§ 371 (c)(1),
(2), (4) Date: May 20, 2010

(87) PCT Pub. No.: WO2009/068171
PCT Pub. Date: Jun. 4, 2009

(65) Prior Publication Data
US 2010/0255988 A1  Oct. 7, 2010

(30) Foreign Application Priority Data
Nov. 30, 2007  (EP) ..................................... 07023152

(51) Int. Cl.
*A01N 43/80* (2006.01)
*C07D 261/04* (2006.01)
*C07D 413/12* (2006.01)

(52) U.S. Cl.
USPC ............................. 504/103; 504/271; 548/243

(58) Field of Classification Search ........................ None
See application file for complete search history.

(56) References Cited

U.S. PATENT DOCUMENTS

| | | | |
|---|---|---|---|
| 4,021,224 A | 5/1977 | Pallos et al. | |
| 4,021,229 A | 5/1977 | Arneklev et al. | |
| 4,137,070 A | 1/1979 | Pallos et al. | |
| 4,631,211 A | 12/1986 | Houghten | |
| 4,881,966 A | 11/1989 | Nyffeler et al. | |
| 4,891,057 A | 1/1990 | Sohn et al. | |
| 4,902,340 A | 2/1990 | Hubele | |
| 5,013,659 A | 5/1991 | Bedbrook et al. | |
| 2005/0256004 A1 | 11/2005 | Takahashi et al. | |

FOREIGN PATENT DOCUMENTS

| | | |
|---|---|---|
| AU | 3495189 A | 11/1989 |
| CN | 87 1 02789 A | 11/1988 |
| EP | 0 086 750 A2 | 8/1983 |
| EP | 0 094 349 A2 | 11/1983 |
| EP | 0 131 624 A1 | 1/1985 |
| EP | 0 142 924 A2 | 5/1985 |
| EP | 0 149 974 A2 | 7/1985 |
| EP | 0 174 562 A2 | 3/1986 |
| EP | 0 191 736 A2 | 8/1986 |
| EP | 0 193 259 A1 | 9/1986 |
| EP | 0 221 044 A1 | 6/1987 |
| EP | 0 242 236 A1 | 10/1987 |
| EP | 0 242 246 A1 | 10/1987 |
| EP | 0 257 993 A2 | 3/1988 |
| EP | 0 269 806 A1 | 6/1988 |
| EP | 0 305 398 A1 | 3/1989 |
| EP | 0 309 862 A1 | 4/1989 |
| EP | 0 333 131 A1 | 9/1989 |
| EP | 0 346 620 A1 | 12/1989 |
| EP | 0 365 484 A1 | 4/1990 |
| EP | 0 464 461 A2 | 1/1992 |
| EP | 0 492 366 A2 | 7/1992 |
| EP | 0 582 198 A2 | 2/1994 |
| EP | 0 860 750 A2 | 8/1998 |
| EP | 1 019 368 A1 | 7/2000 |
| EP | 1 364 946 A1 | 11/2003 |
| EP | 1 541 561 A1 | 6/2005 |
| JP | 8-225548 A | 9/1996 |
| WO | 84/02919 A1 | 8/1984 |
| WO | 87/06766 A1 | 11/1987 |
| WO | 91/07874 A1 | 6/1991 |
| WO | 91/08202 A1 | 6/1991 |
| WO | 91/13972 A1 | 9/1991 |
| WO | 91/19806 A1 | 12/1991 |
| WO | 92/00377 A1 | 1/1992 |

(Continued)

OTHER PUBLICATIONS

Organic Chemistry: An Intermediate Text, Second Edition, by Robert V. Hoffman, 2004 pp. 125-176.*

(Continued)

*Primary Examiner* — Kamal Saeed
(74) *Attorney, Agent, or Firm* — Baker Donelson Bearman Caldwell and Berkowitz, PC

(57) ABSTRACT

The invention relates to 3-(benzylsulfinyl)-5,5-dimethyl-4,5-dihydroisoxazole derivatives and 5,5-dimethyl-3-[(1H-pyrazol-4-ylmethyl)sulfinyl]-4,5-dihydroisoxazole derivatives of the formula (I) and their salts

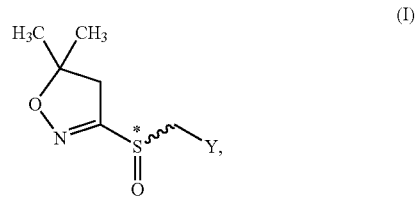

processes for their preparation and their use as herbicides and plant growth regulators, in particular as herbicides for the selective control of harmful plants in crops of useful plants.

19 Claims, No Drawings

FOREIGN PATENT DOCUMENTS

| | | |
|---|---|---|
| WO | 92/11376 A1 | 7/1992 |
| WO | 92/14827 A1 | 9/1992 |
| WO | 95/07897 A1 | 3/1995 |
| WO | 97/45016 A1 | 12/1997 |
| WO | 99/16744 A1 | 4/1999 |
| WO | 01/12613 A1 | 2/2001 |
| WO | 02/34048 A1 | 5/2002 |
| WO | 02/062770 A1 | 8/2002 |
| WO | 03/010165 A1 | 2/2003 |
| WO | 03/000686 A1 | 3/2003 |
| WO | 2004/013106 A1 | 2/2004 |
| WO | 2004/014138 A1 | 2/2004 |
| WO | 2005/104848 A1 | 11/2005 |
| WO | 2005/105755 A1 | 11/2005 |
| WO | 2006/024820 A1 | 3/2006 |
| WO | 2006/037945 A1 | 4/2006 |
| WO | 2007/003294 A1 | 1/2007 |
| WO | 2007/003295 A2 | 1/2007 |
| WO | 2007/071900 A1 | 6/2007 |
| ZA | 8901960 A | 10/1989 |
| ZA | 9407120 A | 5/1995 |

OTHER PUBLICATIONS

International Search Report, PCT/EP2008/009438, Jul. 21, 2009 (10 pages).

* cited by examiner

CHIRAL 3-(BENZYLSULFINYL)-5,5-DIMETHYL-4,5-DIHYDROISOXAZOLE DERIVATIVES AND 5,5-DIMETHYL-3-[(1H-PYRAZOL-4-YLMETHYL)SULFINYL]-4,5-DIHYDROISOXAZOLE DERIVATIVES, METHOD FOR THE PRODUCTION THEREOF, AND USE OF SAME AS HERBICIDES AND PLANT GROWTH REGULATIONS

CROSS REFERENCE TO RELATED APPLICATIONS

This application is a §371 national stage application of PCT/EP2008/009438 filed Nov. 8, 2008, which claims priority to European Application 07023152.7 filed Nov. 30, 2007.

BACKGROUND OF THE INVENTION

1. Field of the Invention

The present invention relates to 3-(benzylsulfinyl)-5,5-dimethyl-4,5-dihydroisoxazole derivatives and 5,5-dimethyl-3-[(1H-pyrazol-4-ylmethyl)sulfinyl]-4,5-dihydroisoxazole derivatives. The present invention furthermore provides mixtures of the isoxazole derivatives mentioned above with other herbicides and/or safeners. In addition, the present invention relates to processes for preparing the isoxazole derivatives mentioned above and to the use of these compounds as plant growth regulators alone and in mixtures with safeners and/or in mixtures with other herbicides, in particular to their use for controlling plants in specific plant crops or as crop protection regulators.

2. Description of Related Art

It is already known from the prior art that certain 5,5-dimethyl-4,5-dihydroisoxazole derivatives have herbicidal properties. Thus, the patents JP 1996/08225548 A and WO 2001/012613 A disclose herbicidally active 4,5-dihydroisoxazole derivatives which carry a benzylthio, benzylsulfinyl or benzylsulfonyl group as substituent at the 3-position of the isoxazoline ring.

WO 2002/062770 A (=EP-A-1 364 946), WO 2003/000686 A, WO 2006/024820 A, WO 2007/003294 A, WO 2007/071900 A, WO 2006/037945 A, WO 2005/104848 A and US 2005/256004 A1 describe various 3-[(pyrazolylmethyl)thio], 3-[(pyrazolylmethyl)sulfinyl] and 3-[(pyrazolylmethyl)sulfonyl]-4,5-dihydroisoxazole derivatives, their preparation and their use as herbicides.

Furthermore, WO 2004/013106 A and WO 2007/003295 A describe processes for preparing corresponding isoxazole derivatives.

However, on application, the active compounds already known from the prior art have disadvantages, be it
(a) that they have no or else insufficient herbicidal activity against harmful plants,
(b) that the spectrum of harmful plants that can be controlled with one active compound is not wide enough, and/or
(c) that their selectivity in crops of useful plants is insufficient.

In particular, the herbicidally active isoxazole compounds known from the prior art have unsatisfactory herbicidal activity against specific weed grasses and at the same time unsatisfactory crop compatibility in specific crops.

SUMMARY OF THE INVENTION

It is therefore desirable to provide alternative chemical active compounds based on isoxazole derivatives which can be used as herbicides or plant growth regulators and which are associated with certain advantages compared to systems known from the prior art.

It is thus the general object of the present invention to provide alternative isoxazole derivatives which can be used as herbicides or plant growth regulators, in particular having a satisfactory herbicidal action against harmful plants, covering a broad spectrum of harmful plants and/or having high selectivity in crops of useful plants. Preferably, these isoxazole derivatives should have a better property profile, in particular better herbicidal activity against harmful plants, cover a broader spectrum of harmful plants and/or have higher selectivity in crops of useful plants than the isoxazole derivatives known from the prior art.

A particular object of the present invention is to provide herbicidally active isoxazole compounds having improved herbicidal activity against specific weed grasses compared to isoxazole derivatives known from the prior art.

Another particular object of the present invention is to provide herbicidally active isoxazole compounds having improved crop compatibility in specific crops compared to isoxazole derivatives known from the prior art.

A particular object of the present invention is to provide herbicidally active isoxazole compounds which, at the same time, have improved herbicidal activity against specific weed grasses and improved crop compatibility in specific crops compared to isoxazole derivatives known from the prior art.

The present invention now provides specific 3-(benzylsulfinyl)-5,5-dimethyl-4,5-dihydroisoxazole and 5,5-dimethyl-3-[(1H-pyrazol-4-ylmethyl)sulfinyl]-4,5-dihydroisoxazole derivatives optically active at the sulfoxide function, which compounds have advantages compared to the compounds known from the prior art or racemic mixtures thereof.

According to the invention, it has been found that these 3-(benzylsulfinyl)-5,5-dimethyl-4,5-dihydroisoxazole and 5,5-dimethyl-3-[(1H-pyrazol-4-ylmethyl)sulfinyl]-4,5-dihydroisoxazole derivatives according to the invention and which are optically active at the sulfoxide function have improved herbicidal activity against *Alopecurus myosuroides* (black-grass), *Lolium multiflorum* (Italian ryegrass) and *Setaria viridis* (green foxtail) compared to isoxazole derivatives known from the prior art.

According to the invention, it has furthermore been found that these 3-(benzylsulfinyl)-5,5-dimethyl-4,5-dihydroisoxazole and 5,5-dimethyl-3-[(1H-pyrazol-4-ylmethyl)sulfinyl]-4,5-dihydroisoxazole derivatives according to the invention and which are optically active at the sulfoxide function, have improved crop compatibility in *Brassica napus* (winter rape) compared to isoxazole derivatives known from the prior art.

According to the invention, it has finally also been found that these 3-(benzylsulfinyl)-5,5-dimethyl-4,5-dihydroisoxazole and 5,5-dimethyl-3-[(1H-pyrazol-4-ylmethyl)sulfinyl]-4,5-dihydroisoxazole derivatives according to the invention and which are optically active at the sulfoxide function, have both improved herbicidal activity against *Alopecurus myosuroides* (black-grass), *Lolium multiflorum* (Italian ryegrass) and *Setaria viridis* (green foxtail) and improved crop compatibility in *Brassica napus* (winter rape) compared to isoxazole derivatives known from the prior art.

Accordingly, the present invention provides optically active compounds of the formula (I), their agrochemically acceptable salts and their agrochemically acceptable quaternized nitrogen derivatives

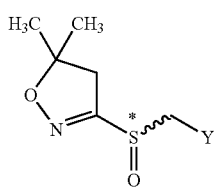

(I)

in which
Y is either

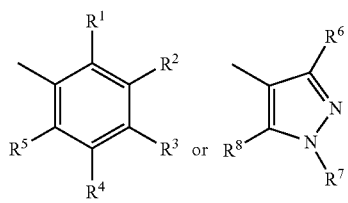

and
the individual substituents $R^1$ to $R^8$ are each independently of one another selected from the group consisting of
hydrogen, halogen, hydroxyl, cyano, nitro, amino, C(O)OH, formyl,
($C_1$-$C_6$)-alkyl, ($C_1$-$C_6$)-haloalkyl, ($C_1$-$C_6$)-alkylcarbonyl, ($C_1$-$C_6$)-haloalkylcarbonyl, ($C_1$-$C_6$)-alkylcarbonyloxy, ($C_1$-$C_6$)-haloalkylcarbonyloxy, ($C_1$-$C_6$)-alkylcarbonyl-($C_1$-$C_4$)-alkyl, ($C_1$-$C_6$)-haloalkylcarbonyl-($C_1$-$C_4$)-alkyl, ($C_1$-$C_6$)-alkylcarbonyl-($C_1$-$C_4$)-haloalkyl, ($C_1$-$C_6$)-haloalkylcarbonyl-($C_1$-$C_4$)-haloalkyl,
($C_1$-$C_6$)-alkoxy, ($C_1$-$C_6$)-haloalkoxy, ($C_1$-$C_6$)-alkoxycarbonyl, ($C_1$-$C_6$)-halo-alkoxycarbonyl, ($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkoxycarbonyl-($C_1$-$C_6$)-haloalkyl, ($C_1$-$C_6$)-haloalkoxycarbonyl-($C_1$-$C_6$)-haloalkyl,
($C_2$-$C_6$)-alkenyl, ($C_2$-$C_6$)-haloalkenyl, ($C_2$-$C_6$)-alkenylcarbonyl, ($C_2$-$C_6$)-haloalkenylcarbonyl, ($C_2$-$C_6$)-alkenyloxy, ($C_2$-$C_6$)-haloalkenyloxy, ($C_2$-$C_6$)-alkenyloxycarbonyl, ($C_2$-$C_6$)-haloalkenyloxycarbonyl,
($C_2$-$C_6$)-alkynyl, ($C_2$-$C_6$)-haloalkynyl, ($C_2$-$C_6$)-alkynylcarbonyl, ($C_2$-$C_6$)-haloalkynylcarbonyl, ($C_2$-$C_6$)-alkynyloxy, ($C_2$-$C_6$)-haloalkynyloxy, ($C_2$-$C_6$)-alkynyloxycarbonyl, ($C_2$-$C_6$)-haloalkynyloxycarbonyl,
($C_1$-$C_6$)-alkylthiocarbonyl, ($C_1$-$C_6$)-haloalkylthiocarbonyl, ($C_1$-$C_6$)-alkylthiocarbonyloxy, ($C_1$-$C_6$)-haloalkylthiocarbonyloxy,
($C_1$-$C_6$)-alkylthio-($C_1$-$C_6$)-alkoxy, ($C_1$-$C_6$)-alkylthio-($C_1$-$C_6$)-alkylcarbonyl, ($C_1$-$C_6$)-alkylthio-($C_1$-$C_6$)-alkylcarbonyloxy,
($C_6$-$C_{14}$)-aryl, ($C_6$-$C_{14}$)-aryloxy, ($C_6$-$C_{14}$)-arylcarbonyl, ($C_6$-$C_{14}$)-aryloxycarbonyl,
($C_6$-$C_{14}$)-aryl-($C_1$-$C_6$)-alkyl, ($C_6$-$C_{14}$)-aryloxy-($C_1$-$C_6$)-alkyl, ($C_6$-$C_{14}$)-aryl-($C_1$-$C_6$)-alkoxy, ($C_6$-$C_{14}$)-aryl-($C_1$-$C_6$)-alkyl-carbonyl, ($C_6$-$C_{14}$)-aryl-($C_1$-$C_6$)-alkyl-carbonyloxy, ($C_6$-$C_{14}$)-aryl-($C_1$-$C_6$)-alkoxycarbonyl, ($C_6$-$C_{14}$)-aryl-($C_1$-$C_6$)-alkoxycarbonyloxy,
($C_1$-$C_6$)-alkylsulfonyl, ($C_1$-$C_6$)-alkylthio, ($C_1$-$C_6$)-alkylsulfinyl, ($C_1$-$C_6$)-haloalkylsulfonyl, ($C_1$-$C_6$)-haloalkylthio, ($C_1$-$C_6$)-haloalkylsulfinyl, ($C_1$-$C_6$)-alkylsulfonyl-($C_1$-$C_6$)-alkyl, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-haloalkylsulfonyl-($C_1$-$C_6$)-alkyl, ($C_1$-$C_6$)-haloalkylthio-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-haloalkyl, ($C_1$-$C_6$)-alkylthio-($C_1$-$C_6$)-haloalkyl, ($C_1$-$C_6$)-alkylsulfinyl-($C_1$-$C_6$)-haloalkyl, ($C_1$-$C_6$)-haloalkylsulfonyl-($C_1$-$C_6$)-haloalkyl, ($C_1$-$C_6$)-haloalkylthio-($C_1$-$C_6$)-haloalkyl, ($C_1$-$C_6$)-haloalkylsulfinyl-($C_1$-$C_6$)-haloalkyl, ($C_1$-$C_6$)-alkylsulfonyloxy, ($C_1$-$C_6$)-haloalkylsulfonyloxy,
($C_4$-$C_{14}$)-arylsulfonyl, ($C_6$-$C_{14}$)-arylthio, ($C_6$-$C_{14}$)-arylsulfinyl,
mono-(($C_1$-$C_6$)-alkyl)-amino, mono-(($C_1$-$C_6$)-haloalkyl)-amino, di-(($C_1$-$C_6$)-alkyl)-amino, di-(($C_1$-$C_6$)-haloalkyl)-amino, (($C_1$-$C_6$)-alkyl-($C_1$-$C_6$)-haloalkyl)-amino, N—(($C_1$-$C_6$)-alkanoyl)-amino, N—(($C_1$-$C_6$)-haloalkanoyl)-amino, aminocarbonyl-($C_1$-$C_6$)-alkyl, mono-($C_1$-$C_6$)-alkylaminocarbonyl-($C_1$-$C_6$)-alkyl, mono-(($C_1$-$C_6$)-alkyl)-aminocarbonyl, di-($C_1$-$C_6$)-alkylaminocarbonyl-($C_1$-$C_6$)-alkyl,
($C_1$-$C_6$)-alkoxy-($C_1$-$C_6$)-alkyl, ($C_1$-$C_6$)-alkoxy-($C_1$-$C_6$)-alkoxy, ($C_1$-$C_6$)-alkoxycarbonyl-($C_1$-$C_6$)-alkoxy,
($C_3$-$C_8$)-cycloalkyl, ($C_3$-$C_8$)-cycloalkoxy, ($C_3$-$C_8$)-cycloalkyl-($C_1$-$C_6$)-alkyl, ($C_3$-$C_8$)-cycloalkyl-($C_1$-$C_6$)-haloalkyl, ($C_3$-$C_8$)-cycloalkyl-($C_1$-$C_6$)-alkoxy, ($C_3$-$C_8$)-cycloalkyl-($C_1$-$C_6$)-haloalkoxy, ($C_3$-$C_8$)-cycloalkylcarbonyl, ($C_3$-$C_8$)-cycloalkoxycarbonyl, ($C_3$-$C_8$)-cycloalkyl-($C_1$-$C_6$)-alkylcarbonyl, ($C_3$-$C_8$)-cycloalkyl-($C_1$-$C_6$)-haloalkylcarbonyl, ($C_3$-$C_8$)-cycloalkyl-($C_1$-$C_6$)-alkoxycarbonyl, ($C_3$-$C_8$)-cycloalkyl-($C_1$-$C_6$)-haloalkoxycarbonyl, ($C_3$-$C_8$)-cycloalkylcarbonyloxy, ($C_3$-$C_8$)-cycloalkoxycarbonyloxy, ($C_3$-$C_8$)-cycloalkyl-($C_1$-$C_6$)-alkylcarbonyloxy, ($C_3$-$C_8$)-cycloalkyl-($C_1$-$C_6$)-haloalkylcarbonyloxy, ($C_3$-$C_8$)-cycloalkyl-($C_1$-$C_6$)-alkoxycarbonyloxy, ($C_3$-$C_8$)-cycloalkyl-($C_1$-$C_6$)-haloalkoxycarbonyloxy,
($C_3$-$C_8$)-cycloalkenyl, ($C_3$-$C_8$)-cycloalkenyloxy, ($C_3$-$C_8$)-cycloalkenyl-($C_1$-$C_6$)-alkyl, ($C_3$-$C_8$)-cycloalkenyl-($C_1$-$C_6$)-haloalkyl, ($C_3$-$C_8$)-cycloalkenyl-($C_1$-$C_6$)-alkoxy, ($C_3$-$C_8$)-cycloalkenyl-($C_1$-$C_6$)-haloalkoxy, ($C_3$-$C_8$)-cycloalkenylcarbonyl, ($C_3$-$C_8$)-cycloalkenyloxycarbonyl, ($C_3$-$C_8$)-cycloalkenyl-($C_1$-$C_6$)-alkylcarbonyl, ($C_3$-$C_8$)-cycloalkenyl-($C_1$-$C_6$)-haloalkylcarbonyl, ($C_3$-$C_8$)-cycloalkenyl-($C_1$-$C_6$)-alkoxycarbonyl, ($C_3$-$C_8$)-cycloalkenyl-($C_1$-$C_6$)-haloalkoxycarbonyl, ($C_3$-$C_8$)-cycloalkenylcarbonyloxy, ($C_3$-$C_8$)-cycloalkenyloxycarbonyloxy, ($C_3$-$C_8$)-cycloalkenyl-($C_1$-$C_6$)-alkylcarbonyloxy, ($C_3$-$C_8$)-cycloalkenyl-($C_1$-$C_6$)-haloalkylcarbonyloxy, ($C_3$-$C_8$)-cycloalkenyl-($C_1$-$C_6$)-alkoxycarbonyloxy, ($C_3$-$C_8$)-cycloalkenyl-($C_1$-$C_6$)-haloalkoxycarbonyloxy,
($C_3$-$C_8$)-cycloalkylthio, ($C_3$-$C_8$)-alkenylthio, ($C_3$-$C_8$)-cycloalkenylthio, ($C_3$-$C_6$)-alkynylthio,
hydroxy-($C_1$-$C_6$)-alkyl, hydroxy-($C_1$-$C_6$)-alkoxy, cyano-($C_1$-$C_6$)-alkoxy, cyano-($C_1$-$C_6$)-alkyl,
3-oxetanyloxy,
pyrimidinyl-2-yl and 4,6-dimethoxypyrimidinyl-2-yl,
C(O)$NR^9R^{10}$ where $R^9$ and $R^{10}$ independently of one another are hydrogen, ($C_1$-$C_6$)-alkyl, ($C_3$-$C_6$)-cycloalkyl, ($C_1$-$C_6$)-haloalkyl, or where $R^9$ and $R^{10}$ together form a ($C_1$-$C_6$)-alkylene group which may contain one oxygen or sulfur atom or one or two amino or ($C_1$-$C_6$)-alkylamino groups,
where the radicals mentioned may, if appropriate, be attached cyclically to one another, provided they are ortho to one another and/or
two substituents ortho to one another together form a ($C_1$-$C_6$)-alkylene group which may contain one or more oxygen and/or sulfur atoms, where the ($C_1$-$C_6$)-alkylene group may be mono- or polysubstituted by halogen and the halogen substituents in question may be identical or different; and where the radicals cycloalkyl and aryl may be mono- or polysubstituted independently of one another.

DETAILED DESCRIPTION OF A PREFERRED EMBODIMENT

If the radicals comprising cycloalkyl and aryl are substituted, the substituents are preferably selected from the group consisting of ($C_1$-$C_6$)-alkyl, ($C_1$-$C_6$)-haloalkyl, ($C_1$-$C_6$)-alkoxy, nitro, cyano, ($C_1$-$C_3$)-cycloalkyl, ($C_1$-$C_6$)-haloalkoxy, ($C_1$-$C_6$)-alkylthio, ($C_1$-$C_6$)-alkylcarbonyl, ($C_1$-$C_6$)-alkoxycarbonyl or halogen, where the radicals mentioned may, if appropriate, be cyclically attached to one another, provided they are ortho to each other.

In the first instance, preferred, particularly preferred and very particularly preferred meanings of the individual substituents $R^1$ to $R^8$ are described below.

A first embodiment of the present invention comprises compounds of the formula (I) in which
Y is

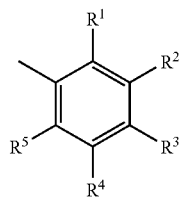

and
$R^1$ is preferably selected from the group consisting of hydrogen, hydroxyl, halogen, cyano, nitro, amino, C(O)OH, ($C_1$-$C_4$)-alkyl, ($C_3$-$C_6$)-cycloalkyl, ($C_1$-$C_4$)-haloalkyl, ($C_1$-$C_4$)-alkoxy, ($C_1$-$C_4$)-haloalkoxy, ($C_1$-$C_4$)-alkoxy-($C_1$-$C_2$)-alkyl, ($C_1$-$C_3$)-alkylcarbonyl, ($C_1$-$C_3$)-alkylcarbonyloxy, ($C_1$-$C_4$)-alkoxycarbonyl, ($C_1$-$C_4$)-alkoxy-($C_1$-$C_4$)-alkoxy, ($C_3$-$C_6$)-cycloalkoxycarbonyl, ($C_3$-$C_6$)-cycloalkyl-($C_1$-$C_2$)-alkoxy, ($C_3$-$C_6$)-cycloalkoxy, ($C_1$-$C_4$)-alkoxycarbonyl-($C_1$-$C_2$)-alkoxy, ($C_3$-$C_4$)-alkenyloxy, ($C_3$-$C_4$)-alkynyloxy, ($C_1$-$C_4$)-alkylthio, ($C_1$-$C_4$)-haloalkylthio, ($C_1$-$C_4$)-alkylsulfinyl, ($C_1$-$C_4$)-haloalkylsulfinyl, ($C_1$-$C_4$)-alkylsulfonyl, ($C_1$-$C_4$)-haloalkylsulfonyl, ($C_1$-$C_4$)-alkylsulfonyloxy, di-($C_1$-$C_4$)-alkylamino, $C_6$-aryl-($C_1$-$C_4$)-alkyl, ($C_3$-$C_4$)-alkenyloxycarbonyl, ($C_2$-$C_4$)-alkynyloxycarbonyl, $C_6$-aryl-($C_1$-$C_4$)-alkoxycarbonyl, $C_6$-aryl-($C_1$-$C_4$)-alkoxy, formyl, ($C_2$-$C_4$)-alkenyl, ($C_2$-$C_4$)-alkynyl, phenyl; —C(O)NR$^9$R$^{10}$, where $R^9$ and $R^{10}$ independently of one another are selected from the group consisting of hydrogen, ($C_1$-$C_6$)-alkyl, ($C_3$-$C_6$)-cycloalkyl, ($C_1$-$C_6$)-haloalkyl, or where $R^9$ and $R^{10}$ together form a ($C_1$-$C_6$)-alkylene group which may contain one oxygen or sulfur atom or one or two amino or ($C_1$-$C_6$)-alkylamino groups; or $R^1$ together with $R^2$ forms a radical —OCH$_2$CH$_2$O—, —OCF$_2$O— or —OCH$_2$OCH$_2$—,
where the radicals cycloalkyl and aryl may be mono- or polysubstituted independently of one another;
$R^1$ is particularly preferably selected from the group consisting of H, F, Cl, Br, I, CN, OH, NH$_2$, NO$_2$, Me, Et, Ph, CHF$_2$, CF$_3$, OMe, OEt, OPr, OiPr, OBu, OcPen, OcHex, OCHF$_2$, OCF$_3$, OCH$_2$CF$_3$, C(O)OH, C(O)OMe, C(O)OEt, C(O)OPr, C(O)OiPr, C(O)OBu, C(O)OiBu, C(O)OsBu, C(O)OcPen, C(O)OCH$_2$CH=CH$_2$, C(O)OCH$_2$C≡CH, C(O)OCH$_2$Ph, CH$_2$OMe, CH$_2$OEt, CH$_2$OBu, OCH$_2$cPr, OCH$_2$CH=CH$_2$, OCH$_2$C≡CH, OCH$_2$Ph, OCH$_2$C(O)OMe, OCH$_2$C(O)OEt, OCH$_2$CH$_2$C(O)OMe, OCH$_2$CH$_2$C(O)OEt, OC(O)Me, OSO$_2$Me, S(O)Me, SCF$_3$, S(O)CF$_3$OCH$_2$CH$_2$OMe, OCH$_2$CH$_2$OEt, C(O)OCH$_2$Ph($_2$—Cl), C(O)OCH$_2$Ph(3-Cl), C(O)OCH$_2$Ph(4-Cl) and S(O)$_2$CF$_3$; or $R^1$ together with $R^2$ forms a radical —OCH$_2$CH$_2$O—, —OCF$_2$O— or —OCH$_2$OCH$_2$—,
$R^1$ is very particularly preferably selected from the group consisting of H, F, Cl, Br, Me, CHF$_2$, CF$_3$, OMe, OCHF$_2$, OCF$_3$ and OCH$_2$CF$_3$.

A second embodiment of the present invention comprises compounds of the formula (I) in which
Y is

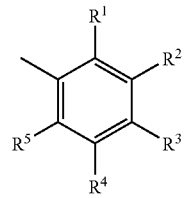

and
$R^2$ is preferably selected from the group consisting of hydrogen, hydroxyl, halogen, cyano, nitro, amino, C(O)OH, ($C_1$-$C_4$)-alkyl, ($C_3$-$C_6$)-cycloalkyl, ($C_1$-$C_4$)-haloalkyl, ($C_1$-$C_4$)-alkoxy, ($C_1$-$C_4$)-haloalkoxy, ($C_1$-$C_4$)-alkoxy-($C_1$-$C_2$)-alkyl, ($C_1$-$C_3$)-alkylcarbonyl, ($C_1$-$C_3$)-alkylcarbonyloxy, ($C_1$-$C_4$)-alkoxycarbonyl, ($C_3$-$C_6$)-cycloalkoxycarbonyl, ($C_3$-$C_6$)-cycloalkyl-($C_1$-$C_2$)-alkoxy, ($C_3$-$C_6$)-cycloalkoxy, ($C_1$-$C_4$)-alkoxycarbonyl-($C_1$-$C_2$)-alkoxy, ($C_3$-$C_4$)-alkenyloxy, ($C_3$-$C_4$)-alkynyloxy, ($C_1$-$C_4$)-alkylthio, ($C_1$-$C_4$)-haloalkylthio, ($C_1$-$C_4$)-alkylsulfinyl, ($C_1$-$C_4$)-haloalkylsulfinyl, ($C_1$-$C_4$)-alkylsulfonyl, ($C_1$-$C_4$)-haloalkylsulfonyl, ($C_1$-$C_4$)-alkylsulfonyloxy, di-($C_1$-$C_4$)-alkylamino, $C_6$-aryl-($C_1$-$C_4$)-alkyl, ($C_3$-$C_4$)-alkenyloxycarbonyl, ($C_2$-$C_4$)-alkynyloxycarbonyl, $C_6$-aryl-($C_1$-$C_4$)-alkoxycarbonyl, $C_6$-aryl-($C_1$-$C_4$)-alkoxy, formyl, ($C_2$-$C_4$)-alkenyl, ($C_2$-$C_4$)-alkynyl, $C_6$-aryl, —C(O)NR$^9$R$^{10}$, where $R^9$ and $R^{10}$ independently of one another are selected from the group consisting of hydrogen, ($C_1$-$C_6$)-alkyl, ($C_3$-$C_6$)-cycloalkyl, ($C_1$-$C_6$)-haloalkyl, or where $R^9$ and $R^{10}$ together form a ($C_1$-$C_6$)-alkylene group which may contain one oxygen or sulfur atom or one or two amino or ($C_1$-$C_6$)-alkylamino groups; or $R^2$ together with $R^1$ or $R^3$ forms a radical —OCH$_2$CH$_2$O—, —OCF$_2$O— or —OCH$_2$OCH$_2$—;
where the radicals cycloalkyl and aryl may be mono- or polysubstituted independently of one another;
$R^2$ is particularly preferably selected from the group consisting of H, F, Cl, Br, CN, OH, NO$_2$, Me, iPr, CHF$_2$, CF$_3$, OMe, OEt, OPr, OiPr, OBu, OCHF$_2$, OCF$_3$, OCH$_2$CF$_3$, C(O)OH and C(O)OMe, or $R^2$ together with $R^1$ or $R^3$ forms a radical —OCH$_2$CH$_2$O—, —OCF$_2$O— or —OCH$_2$OCH$_2$—;
$R^2$ is very particularly preferably selected from the group consisting of H, F, Cl, Me and CF$_3$.

A third embodiment of the present invention comprises compounds of the formula (I) in which Y is

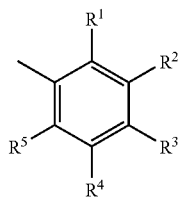

and
$R^3$ is preferably selected from the group consisting of hydrogen, hydroxyl, halogen, cyano, nitro, amino, C(O)OH, ($C_1$-$C_4$)-alkyl, ($C_3$-$C_6$)-cycloalkyl, ($C_1$-$C_4$)-haloalkyl, ($C_1$-$C_4$)-alkoxy, ($C_1$-$C_4$)-haloalkoxy, ($C_1$-$C_4$)-alkoxy-($C_1$-$C_2$)-alkyl, ($C_1$-$C_3$)-alkylcarbonyl, ($C_1$-$C_3$)-alkylcarbonyloxy, ($C_1$-$C_4$)-alkoxycarbonyl, ($C_3$-$C_6$)-cycloalkoxycarbonyl, ($C_3$-$C_6$)-cycloalkyl-($C_1$-$C_2$)-alkoxy, ($C_3$-$C_6$)-cycloalkoxy, ($C_1$-$C_4$)-alkoxycarbonyl-($C_1$-$C_2$)-alkoxy, ($C_3$-$C_4$)-alkenyloxy, ($C_3$-$C_4$)-alkynyloxy, ($C_1$-$C_4$)-alkylthio, ($C_1$-$C_4$)-haloalkylthio, ($C_1$-$C_4$)-alkylsulfinyl, ($C_1$-$C_4$)-haloalkylsulfinyl, ($C_1$-$C_4$)-alkylsulfonyl, ($C_1$-$C_4$)-haloalkylsulfonyl, ($C_1$-$C_4$)-alkylsulfonyloxy, di-($C_1$-$C_4$)-alkylamino, $C_6$-aryl-($C_1$-$C_4$)-alkyl, ($C_3$-$C_4$)-alkenyloxycarbonyl, ($C_2$-$C_4$)-alkynyloxycarbonyl, $C_6$-aryl-($C_1$-$C_4$)-alkoxycarbonyl, $C_6$-aryl-($C_1$-$C_4$)-alkoxy, formyl, ($C_2$-$C_4$)-alkenyl, ($C_2$-$C_4$)-alkynyl, $C_6$-aryl, —C(O)NR$^9$R$^{10}$, where $R^9$ and $R^{10}$ independently of one another are selected from the group consisting of hydrogen, ($C_1$-$C_6$)-alkyl, ($C_3$-$C_6$)-cycloalkyl, ($C_1$-$C_6$)-haloalkyl, or where $R^9$ and $R^{10}$ together form a ($C_1$-$C_6$)-alkylene group which may contain one oxygen or sulfur atom or one or two amino or ($C_1$-$C_6$)-alkylamino groups; or $R^3$ together with $R^2$ or $R^4$ forms a radical —OCH$_2$CH$_2$O—, —OCF$_2$O— or —OCH$_2$OCH$_2$—;

where the radicals cycloalkyl and aryl may be mono- or polysubstituted independently of one another;
$R^3$ is particularly preferably selected from the group consisting of H, halogen, OH, Me, CF$_3$, OMe, OCHF$_2$, OCF$_3$, OCH$_2$CF$_3$, C(O)OMe and C(O)OEt, or $R^3$ together with $R^2$ or $R^4$ forms a radical —OCH$_2$CH$_2$O—, —OCF$_2$O— or —OCH$_2$OCH$_2$—; and
$R^3$ is very particularly preferably selected from the group consisting of H, F, Cl and CF$_3$.

A fourth embodiment of the present invention comprises compounds of the formula (I) in which
Y is

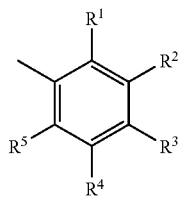

and
$R^4$ is preferably selected from the group consisting of hydrogen, hydroxyl, halogen, cyano, nitro, amino, C(O)OH, ($C_1$-$C_4$)-alkyl, ($C_3$-$C_6$)-cycloalkyl, ($C_1$-$C_4$)-haloalkyl, ($C_1$-$C_4$)-alkoxy, ($C_1$-$C_4$)-haloalkoxy, ($C_1$-$C_4$)-alkoxy-($C_1$-$C_2$)-alkyl, ($C_1$-$C_3$)-alkylcarbonyl, ($C_1$-$C_3$)-alkylcarbonyloxy, ($C_1$-$C_4$)-alkoxycarbonyl, ($C_3$-$C_6$)-cycloalkoxycarbonyl, ($C_3$-$C_6$)-cycloalkyl-($C_1$-$C_2$)-alkoxy, ($C_3$-$C_6$)-cycloalkoxy, ($C_1$-$C_4$)-alkoxycarbonyl-($C_1$-$C_2$)-alkoxy, ($C_3$-$C_4$)-alkenyloxy, ($C_3$-$C_4$)-alkynyloxy, ($C_1$-$C_4$)-alkylthio, ($C_1$-$C_4$)-haloalkylthio, ($C_1$-$C_4$)-alkylsulfinyl, ($C_1$-$C_4$)-haloalkylsulfinyl, ($C_1$-$C_4$)-alkylsulfonyl, ($C_1$-$C_4$)-haloalkylsulfonyl, ($C_1$-$C_4$)-alkylsulfonyloxy, di-($C_1$-$C_4$)-alkylamino, $C_6$-aryl-($C_1$-$C_4$)-alkyl, ($C_3$-$C_4$)-alkenyloxycarbonyl, ($C_2$-$C_4$)-alkynyloxycarbonyl, $C_6$-aryl-($C_1$-$C_4$)-alkoxycarbonyl, $C_6$-aryl-($C_1$-$C_4$)-alkoxy, formyl, ($C_2$-$C_4$)-alkenyl, ($C_2$-$C_4$)-alkynyl, $C_6$-aryl, —C(O)NR$^9$R$^{10}$, where $R^9$ and $R^{10}$ independently of one another are selected from the group consisting of hydrogen, ($C_1$-$C_6$)-alkyl, ($C_3$-$C_6$)-cycloalkyl, ($C_1$-$C_6$)-haloalkyl, or where $R^9$ and $R^{10}$ together form a ($C_1$-$C_6$)-alkylene group which may contain one oxygen or sulfur atoms or one or two amino or ($C_1$-$C_6$)-alkylamino groups; or $R^4$ together with $R^3$ forms a radical —OCH$_2$CH$_2$O—, —OCF$_2$O— or —OCH$_2$OCH$_2$—;

where the radicals cycloalkyl and aryl may be mono- or polysubstituted independently of one another;
$R^4$ is particularly preferably selected from the group consisting of H, halogen, NO$_2$, Me, iPr, OMe, OEt, OPr, OiPr, OBu, OCHF$_2$, CF$_3$, OCF$_3$, OCH$_2$CF$_3$, OCH$_2$CH═CH$_2$ and OCH$_2$C≡CH, or $R^4$ together with $R^3$ forms a radical —OCH$_2$CH$_2$O—, —OCF$_2$O— or —OCH$_2$OCH$_2$—; and
$R^4$ is very particularly preferably selected from the group consisting of H, F, Cl, Me and CF$_3$.

A fifth embodiment of the present invention comprises compounds of the formula (I) in which
Y is

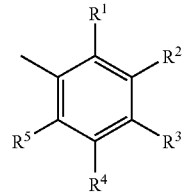

and
$R^5$ is preferably selected from the group consisting of hydrogen, hydroxyl, halogen, cyano, nitro, amino, C(O)OH, ($C_1$-$C_4$)-alkyl, ($C_3$-$C_6$)-cycloalkyl, ($C_1$-$C_4$)-haloalkyl, ($C_1$-$C_4$)-alkoxy, ($C_1$-$C_4$)-haloalkoxy, ($C_1$-$C_4$)-alkoxy-($C_1$-$C_2$)-alkyl, ($C_1$-$C_3$)-alkylcarbonyl, ($C_1$-$C_3$)-alkylcarbonyloxy, ($C_1$-$C_4$)-alkoxycarbonyl, ($C_3$-$C_6$)-cycloalkoxycarbonyl, ($C_3$-$C_6$)-cycloalkyl-($C_1$-$C_2$)-alkoxy, ($C_3$-$C_6$)-cycloalkoxy, ($C_1$-$C_4$)-alkoxycarbonyl-($C_1$-$C_2$)-alkoxy, ($C_3$-$C_4$)-alkenyloxy, ($C_3$-$C_4$)-alkynyloxy, ($C_1$-$C_4$)-alkylthio, ($C_1$-$C_4$)-haloalkylthio, ($C_1$-$C_4$)-alkylsulfinyl, ($C_1$-$C_4$)-haloalkylsulfinyl, ($C_1$-$C_4$)-alkylsulfonyl, ($C_1$-$C_4$)-haloalkylsulfonyl, ($C_1$-$C_4$)-alkylsulfonyloxy, di-($C_1$-$C_4$)-alkylamino, $C_6$-aryl-($C_1$-$C_4$)-alkyl, ($C_3$-$C_4$)-alkenyloxycarbonyl, ($C_2$-$C_4$)-alkynyloxycarbonyl, $C_6$-aryl-($C_1$-$C_4$)-alkoxycarbonyl, $C_6$-aryl-($C_1$-$C_4$)-alkoxy, formyl, ($C_2$-$C_4$)-alkenyl, ($C_2$-$C_4$)-alkynyl, $C_6$-aryl, —C(O)NR$^9$R$^{10}$, where $R^9$ and $R^{10}$ independently of one another are selected from the group consisting of hydrogen, ($C_1$-$C_6$)-alkyl, ($C_3$-$C_6$)-cycloalkyl, ($C_1$-$C_6$)-haloalkyl, or where $R^9$ and $R^{10}$ together form a ($C_1$-$C_6$)-alkylene group which may contain one oxygen or sulfur atom or one or two amino or ($C_1$-$C_6$)-alkylamino groups;

where the radicals cycloalkyl and aryl may be mono- or polysubstituted independently of one another;
$R^5$ is particularly preferably selected from the group consisting of H, halogen, OH, NO$_2$, NMe$_2$, NEt$_2$, Me, Et, CHF$_2$, CF$_3$, OMe, OEt, OPr, OiPr, OBu, OiBu, OCHF$_2$, OCF$_3$, OCH$_2$CF$_3$, C(O)OH, C(O)OMe, C(O)OEt, C(O)OPr, C(O)OiPr, C(O)OBu, C(O)OiBu, C(O)OsBu, C(O)OCH₂Ph, OCH₂CH=CH₂, OCH₂C≡CH and C(O)OCH₂Ph(2-Cl), C(O)OCH₂Ph(3-Cl) and C(O)OCH₂Ph(4-Cl); and R⁵ is very particularly preferably selected from the group consisting of H, F, Cl, Me, CF₃, OCHF₂ and OCF₃.

In the context of the first to fifth embodiments of the present invention, it is possible to combine the specific preferred, particularly preferred and very particularly preferred meanings of the substituents R¹ to R⁵ as desired. This means that the invention comprises compounds of the formula (I) where Y is

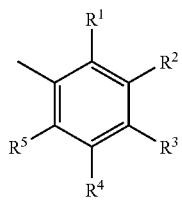

in which, for example, the substituent R¹ has a preferred meaning and the substituents R² to R⁵ have the general meaning, or else, for example, the substituent R² has a preferred meaning, the substituent R³ has a particularly preferred meaning, the substituent R⁴ has a very particular meaning and the substituents R¹ and R⁵ have the general meaning.

A sixth embodiment of the present invention comprises compounds of the formula (I) in which
Y is

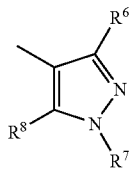

and

R⁶ is preferably selected from the group consisting of hydrogen, halogen, hydroxyl, cyano, nitro, amino, (C₁-C₄)-alkyl, (C₃-C₆)-cycloalkyl, (C₁-C₄)-haloalkyl, (C₁-C₄)-alkoxy, (C₁-C₄)-alkoxy-(C₁-C₂)-alkyl, (C₃-C₆)-cycloalkoxy, (C₁-C₄)-haloalkoxy, (C₁-C₄)-alkylthio, (C₁-C₄)-alkylthio-(C₁-C₂)-alkyl, (C₁-C₄)-alkylsulfinyl, (C₁-C₄)-alkylsulfinyl-(C₁-C₂)-alkyl, (C₁-C₄)-alkylsulfonyl, (C₁-C₄)-alkylsulfonyl-(C₁-C₂)-alkyl, di-(C₁-C₄)-alkylamino, (C₂-C₄)-alkenyl, (C₂-C₄)-alkynyl, (C₃-C₄)-alkenyloxy, (C₃-C₄)-alkynyloxy, (C₃-C₆)-cycloalkyl-(C₁-C₂)-alkoxy, hydroxy-(C₁-C₂)-alkyl, hydroxy-(C₁-C₂)-alkoxy, cyano-(C₁-C₂)-alkoxy, cyano-(C₁-C₂)-alkyl, C₆-aryl, C₆-aryl-(C₁-C₂)-alkyl, C₆-aryl-(C₁-C₂)-alkoxy, phenoxy, (C₁-C₄)-alkylcarbonyloxy, (C₃-C₆)-cycloalkyl-(C₁-C₂)-alkyl, (C₁-C₄)-alkylcarbonyl-(C₁-C₂)-alkyl, (C₁-C₄)-alkoxycarbonyl-(C₁-C₂)-alkyl, aminocarbonyl-(C₁-C₂)-alkyl and 3-oxetanyloxy, —C(O)NR⁹R¹⁰, where R⁹ and R¹⁰ independently of one another are selected from the group consisting of hydrogen, (C₁-C₆)-alkyl, (C₃-C₆)-cycloalkyl, (C₁-C₆)-haloalkyl, or where R⁹ and R¹⁰ together form a (C₁-C₆)-alkylene group which may contain one oxygen or sulfur atom or one or two amino or (C₁-C₆)-alkylamino groups;

where the radicals cycloalkyl and aryl may be mono- or polysubstituted independently of one another;
and R⁶ is particularly preferably selected from the group consisting of H, F, Cl, Br, I, CN, OH, NH₂, NO₂, Me, Et, Pr, iPr, tBu, CHF₂, CF₃, Ph, OMe, OEt, OCHF₂ and OCH₂CF₃; and R⁶ is very particularly preferably selected from the group consisting of F, Cl, Br, CHF₂, CF₃, OCHF₂, OCF₃ and OCH₂CF₃.

A seventh embodiment of the present invention comprises compounds of the formula (I) in which
Y is

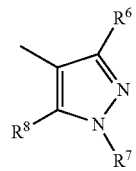

and

R⁷ is preferably selected from the group consisting of hydrogen, (C₁-C₄)-alkyl, (C₁-C₄)-haloalkyl, phenyl, phenyl-(C₁-C₂)-alkyl, (C₃-C₆)-cycloalkyl; (C₃-C₆)-cycloalkyl-(C₁-C₂)-alkyl, where the cycloalkyl radical is optionally substituted by (C₁-C₄)-alkyl; (C₂-C₄)-alkenyl, (C₂-C₄)-alkynyl, (C₁-C₄)-alkoxy-(C₁-C₂)-alkyl, (C₁-C₄)-alkylthio-(C₁-C₂)-alkyl, (C₁-C₄)-alkylsulfinyl-(C₁-C₂)-alkyl, cyano-(C₁-C₂)-alkyl, (C₁-C₄)-alkylsulfonyl-(C₁-C₂)-alkyl, (C₁-C₄)-alkoxycarbonyl-(C₁-C₂)-alkyl, aminocarbonyl-(C₁-C₂)-alkyl, mono-(C₁-C₄)-alkylaminocarbonyl-(C₁-C₂)-alkyl, di-(C₁-C₄)-alkylaminocarbonyl-(C₁-C₂)-alkyl, hydroxy-(C₁-C₄)-alkyl, (C₁-C₄)-alkylcarbonyl-(C₁-C₄)-alkyl, (C₁-C₄)-alkoxycarbonyl-(C₁-C₂)-alkyl, (C₁-C₄)-alkylsulfonyl; phenylsulfonyl which is optionally substituted by one or more identical or different radicals from the group consisting of halogen, nitro, cyano, (C₁-C₆)-alkyl, (C₁-C₆)-haloalkyl, (C₃-C₆)-cycloalkyl, (C₁-C₆)-alkoxy, (C₁-C₆)-haloalkoxy, (C₁-C₆)-alkylcarbonyl, (C₁-C₆)-alkoxycarbonyl and (C₁-C₆)-alkylthio; (C₁-C₄)-alkylcarbonyl; phenylcarbonyl which is optionally substituted by one or more identical or different radicals from the group consisting of halogen, nitro, cyano, (C₁-C₆)-alkyl, (C₁-C₆)-haloalkyl, (C₃-C₆)-cycloalkyl, (C₁-C₆)-alkoxy, (C₁-C₆)-haloalkoxy, (C₁-C₆)-alkylcarbonyl, (C₁-C₆)-alkoxycarbonyl and (C₁-C₆)-alkylthio; pyrimidinyl-2-yl, 4,6-dimethoxypyrimidinyl-2-yl and (C₁-C₄)-alkoxycarbonyl;

where the radicals cycloalkyl and aryl may be mono- or polysubstituted independently of one another;

R⁷ is particularly preferably selected from the group consisting of H, Me, Et, Pr, cPr, iPr, Bu, iBu, sBu, tBu, cPen, cHex, CHF₂, CH₂CF₃, Ph, CH₂cPr, CH₂cPr(2-Me), CHMecPr, CH₂cBu, CH₂cPen, CH₂cHex, CH₂Ph, CH₂CH=CH₂, CH₂C≡CH, CHMeC≡CH, CH₂C≡CMe, CH₂OMe, CH₂OEt, CH₂CH₂OH, CH₂CH₂OMe, CH₂CH₂OEt, CH₂CH₂C(O)Me, CH₂SMe, CH₂SO₂Me, CH₂CN, CH₂C(O)OMe, CH₂C(O)OEt, CH₂C(O)NH₂, CH₂C(O)NMe₂, CH₂C(O)Me, SO₂Me, SO₂Ph, C(O)Me, C(O)Ph, C(O)OMe, Ph(2-Cl), Ph(3-Cl), Ph(4-Cl), Ph(4-OMe), Ph(4-Me), Ph(4-NO₂), Ph(4-CN) and Ph(4-C(O)OMe); or R⁷ together with R⁸ forms a radical —O(CH₂)₃O—;

and

R$^7$ is very particularly preferably selected from the group consisting of Me, Et and CHF$_2$.

An eighth embodiment of the present invention comprises compounds of the formula (I) in which Y is

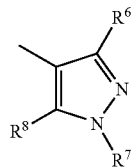

and selected from the group consisting of hydrogen, halogen, hydroxyl, cyano, nitro, amino, (C$_1$-C$_4$)-alkyl, (C$_1$-C$_4$)-halo-alkyl, (C$_3$-C$_6$)-cycloalkyl, (C$_1$-C$_4$)-alkoxy, (C$_1$-C$_4$)-alkoxy-(C$_1$-C$_2$)-alkyl, (C$_3$-C$_6$)-cycloalkoxy, (C$_1$-C$_4$)-haloalkoxy, (C$_1$-C$_4$)-alkylthio, (C$_1$-C$_4$)-alkylthio-(C$_1$-C$_2$)-alkyl, (C$_1$-C$_4$)-alkylsulfinyl, (C$_1$-C$_4$)-alkylsulfinyl-(C$_1$-C$_2$)-alkyl, (C$_1$-C$_4$)-alkylsulfonyl, (C$_1$-C$_4$)-alkylsulfonyl-(C$_1$-C$_2$)-alkyl, di-(C$_1$-C$_4$)-alkylamino, (C$_2$-C$_4$)-alkenyl, (C$_2$-C$_4$)-alkynyl, (C$_3$-C$_4$)-alkenyloxy, (C$_3$-C$_4$)-alkynyloxy, (C$_3$-C$_6$)-cycloalkyl-(C$_1$-C$_2$)-alkoxy, hydroxy-(C$_1$-C$_2$)-alkyl, hydroxy-(C$_1$-C$_2$)-alkoxy, cyano-(C$_1$-C$_2$)-alkoxy, cyano-(C$_1$-C$_2$)-alkyl, C$_6$-aryl, C$_6$-aryl-(C$_1$-C$_2$)-alkyl, C$_6$-aryl-(C$_1$-C$_2$)-alkoxy, phenoxy, (C$_1$-C$_4$)-alkylcarbonyloxy, (C$_3$-C$_6$)-cycloalkyl-(C$_1$-C$_2$)-alkyl, (C$_1$-C$_4$)-alkylcarbonyl-(C$_1$-C$_2$)-alkyl, (C$_1$-C$_4$)-alkoxycarbonyl-(C$_1$-C$_2$)-alkyl, aminocarbonyl-(C$_1$-C$_2$)-alkyl and 3-oxetanyloxy, —C(O)NR$^9$R$^{10}$, where R$^9$ and R$^{10}$ independently of one another are selected from the group consisting of hydrogen, (C$_1$-C$_6$)-alkyl, (C$_3$-C$_6$)-cycloalkyl, (C$_1$-C$_6$)-haloalkyl, or where R$^9$ and R$^{10}$ together form a (C$_1$-C$_6$)-alkylene group which may contain one oxygen or sulfur atom or one or two amino or (C$_1$-C$_6$)-alkylamino groups; or R$^8$ together with R$^7$ forms a radical —O(CH$_2$)$_3$O—, where the radicals cycloalkyl and aryl may be mono- or polysubstituted independently of one another and R$^8$ is particularly preferably selected from the group consisting of H, F, Cl, Br, I, CN, OH, NH$_2$, NO$_2$, Me, Et, CHF$_2$, CF$_3$, OCHF$_2$, OCH$_2$CF$_3$, OMe, OEt, OPr, OiPr, OBu, OtBu, SO$_2$Me, SO$_2$iPr, 3-oxetanyloxy, OPh, OPh(2-Cl), OPh(3-Cl), OPh(4-Cl), OPh(3-OMe), OPh(4-Me), OPh(4-OMe), OCH$_2$CHF$_2$, OCH$_2$CN, OCH$_2$Ph, SEt, SO$_2$Et, SO$_2$Ph, NMe$_2$, OcHex, OCH$_2$Pr, OCH$_2$Pen, OCH$_2$cHex, OcPen, OC(O)Me, CH$_2$cPen, CH$_2$cHex, CH$_2$CH=CH$_2$, CH$_2$C=CH, CHMeC=CH, CH$_2$C=CMe, CH$_2$OMe, CH$_2$OEt, CH$_2$CH$_2$OH, CH$_2$CH$_2$OMe, CH$_2$CH$_2$OEt, CH$_2$SMe, CH$_2$SO$_2$Me, OCH$_2$CH=CH$_2$ and OCH$_2$C≡CH; and R$^8$ is very particularly preferably selected from the group consisting of F, Cl, CHF$_2$, CF$_3$, OCHF$_2$ and OCH$_2$CF$_3$.

In the context of the sixth to eighth embodiments of the present invention, it is possible to combine the specific preferred, particularly preferred and very particularly preferred meanings of the substituents R$^6$ to R$^8$. This means that the invention comprises compounds of the formula (I) where Y is

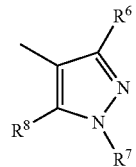

in which, for example, the substituent R$^6$ has a preferred meaning and the substituents R$^7$ and R$^8$ have the general meaning, or else the substituent R$^7$ has a preferred meaning, the substituent R$^8$ has a particularly preferred meaning and the substituent R$^6$ has a very particular meaning.

In the context of the present invention, the compounds of the formula (I) also comprise compounds quaternized at a nitrogen atom by a) protonation, b) alkylation or c) oxidation.

If appropriate, the compounds of the formula (I) may also be able to form salts by forming an adduct with a suitable inorganic or organic acid, such as, for example, HCl, HBr, H$_2$SO$_4$ or HNO$_3$, or else oxalic acid or sulfonic acids, to a basic group, such as, for example, amino or alkylamino. Suitable substituents present in deprotonated form, such as, for example, sulfonic acids or carboxylic acids, are capable of forming inner salts with groups, such as amino groups, which can be protonated for their part. Salts can also be formed by replacing the hydrogen of suitable substituents, such as, for example, sulfonic acids or carboxylic acids, with a cation suitable in the agrochemical sector. These salts are, for example, metal salts, in particular alkali metal salts or alkaline earth metal salts, especially sodium salts and potassium salts, or else ammonium salts, salts with organic amines or quaternary ammonium salts having cations of the formula [NRR'R''R''']$^+$ in which R to R''' in each case independently are an organic radical, in particular alkyl, aryl, aralkyl or alkylaryl.

In the formula (I) and in all the other formulae of the present invention, the radicals alkyl, alkoxy, haloalkyl, haloalkoxy, alkylamino, alkylthio, haloalkylthio, alkylsulfinyl, alkylsulfonyl, haloalkylsulfinyl and haloalkylsulfonyl and the corresponding unsaturated and/or substituted radicals can in each case be straight-chain or branched in the carbon skeleton. Unless indicated specifically, preference is given for these radicals to the lower carbon skeletons, for example those having 1 to 6 carbon atoms, especially 1 to 4 carbon atoms, or in the case of unsaturated groups having 2 to 6 carbon atoms, especially 2 to 4 carbon atoms. Alkyl radicals, also in composite definitions such as alkoxy, haloalkyl, etc., are for example methyl, ethyl; propyls, such as n-propyl or isopropyl; butyls, such as n-, iso-, t- or 2-butyl; pentyls, such as n-pentyl, isopentyl or neopentyl; hexyls, such as n-hexyl, isohexyl, 3-methylpentyl, 2,2-dimethylbutyl or 2,3-dimethylbutyl; heptyls, such as n-heptyl, 1-methylhexyl or 1,4-dimethylpentyl; alkenyl and alkynyl radicals have the meaning of the possible unsaturated radicals corresponding to the alkyl radicals; where at least one double bond or triple bond is present, preferably one double bond or triple bond, respectively. Alkenyl is, for example, vinyl, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, ethynyl, propargyl, but-2-yn-1-yl, but-3-yn-1-yl and 1-methylbut-3-yn-1-yl.

Cycloalkyl groups are, for example, cyclopropyl, cyclobutyl, cyclopentyl, cyclohexyl, cycloheptyl and cyclooctyl. The cycloalkyl groups can be present in bi- or tricyclic form.

If haloalkyl groups and haloalkyl radicals of haloalkoxy, haloalkylthio, haloalkenyl, haloalkynyl etc. are stated, the lower carbon skeletons of these radicals having, for example, 1 to 6 carbon atoms or 2 to 6 carbon atoms, in particular 1 to 4 carbon atoms or preferably 2 to 4 carbon atoms, and the corresponding unsaturated and/or substituted radicals are in each case straight-chain or branched in the carbon skeleton. Examples are difluoromethyl, 2,2,2-trifluoroethyl, trifluoroallyl, 1-chloroprop-1-yl-3-yl.

Alkylene groups in these radicals are the lower carbon skeletons, for example those having 1 to 10 carbon atoms, in particular 1 to 6 carbon atoms, or preferably 2 to 4 carbon atoms, and also the corresponding unsaturated and/or substituted radicals in the carbon skeleton which may in each case be straight-chain or branched. Examples are methylene, ethylene, n- and isopropylene and n-, s-, iso-, t-butylene.

Hydroxyalkyl groups in these radicals are the lower carbon skeletons, for example those having 1 to 6 carbon atoms, in particular 1 to 4 carbon atoms, and also the corresponding unsaturated and/or substituted radicals in the carbon skeleton which may in each case be straight-chain or branched. Examples of these are 1,2-dihydroxyethyl and 3-hydroxypropyl.

Halogen is fluorine, chlorine, bromine or iodine; haloalkyl, haloalkenyl and haloalkynyl are alkyl, alkenyl and alkynyl, respectively, which are fully or partially substituted by halogen, preferably by fluorine, chlorine or bromine, in particular by fluorine and/or chlorine, examples being monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$, and $OCH_2CH_2Cl$; this correspondingly applies to haloalkenyl and other halogen-substituted radicals.

Aryl is a monocyclic, bicyclic or polycyclic aromatic system, for example phenyl or naphthyl, preferably phenyl.

The definition "substituted by one or more radicals" refers, unless otherwise defined, to one or more identical or different radicals.

The substituents given by way of example ("first substituent level") can, if they include hydrocarbon-containing fractions, be further substituted therein if desired ("second substituent level"), by for example one of the substituents as defined for the first substituent level. Corresponding further substituent levels are possible. The term "substituted radical" preferably embraces just one or two substituent levels.

In the case of radicals having carbon atoms, preference is given to those having 1 to 6 carbon atoms, preferably 1 to 4 carbon atoms, in particular 1 or 2 carbon atoms. Preference is generally given to substituents from the group consisting of halogen, for example fluorine and chlorine, $(C_1-C_4)$-alkyl, preferably methyl or ethyl, $(C_1-C_4)$-haloalkyl, preferably trifluoromethyl, $(C_1-C_4)$-alkoxy, preferably methoxy or ethoxy, $(C_1-C_4)$-haloalkoxy, nitro and cyano.

Optionally substituted aryl is preferably phenyl which is unsubstituted or mono- or polysubstituted, preferably up to trisubstituted, by identical of different radicals from the group consisting of halogen, $(C_1-C_4)$-alkyl, $(C_3-C_6)$-cycloalkyl, $(C_1-C_4)$-alkoxy, $(C_1-C_4)$-haloalkyl, $(C_1-C_4)$-haloalkoxy, $(C_1-C_4)$-alkylthio, $(C_1-C_6)$-alkylcarbonyl, $(C_1-C_6)$-alkoxycarbonyl, cyano and nitro, for example o-, m- and p-tolyl, dimethylphenyls, 2-, 3- and 4-chlorophenyl, 2-, 3- and 4-trifluoromethyl and 2-, 3- and 4-trichloromethylphenyl, 2,4-, 3,5-, 2,5- and 2,3-dichlorophenyl, o-, m- and p-methoxyphenyl.

Primarily for reasons of higher herbicidal activity, better selectivity and/or better producibility, compounds of the formula (I) according to the invention or their agrochemical salts or quaternary N derivatives are of particular interest in which individual radicals have one of the preferred meanings already specified or specified below, or in particular those in which one or more of the preferred meanings already specified or specified below occur in combination.

The abovementioned general or preferred radical definitions apply both to the end products of the formula (I) and, correspondingly, to the starting materials or the intermediates required in each case for the preparation. These radical definitions can be exchanged for one another as desired, i.e. including combinations between the given preferred ranges.

The present compounds of the formula (I) have a chiral sulfur atom which, in the structure shown above, is illustrated by the marker (*). According to the rules of Cahn, Ingold and Prelog (CIP rules), this sulfur atom can have either an (R) configuration or an (S) configuration.

The present invention encompasses compounds of the formula (I) both with (S) and with (R) configuration, i.e. the present invention encompasses the compounds of the formula (I) in which the sulfur atom in question has (1) an (R) configuration; or
(2) an (S) configuration In addition, the scope of the present invention also encompasses (3) any mixtures of compounds of the formula (I) having an (R) configuration (compounds of the formula (I-(R)) with compounds of the formula (I) having an (S) configuation (compounds of the formula (I-(S)), where a racemic mixture of the compounds of the formula (I) having (R) and (S) configuration is excluded from the present invention.

However, within the context of the present invention, preference is given to using in particular compounds of the formula (I) having (S) configuration (compounds of the formula (I-S)) as compared to the (R) configuration (compounds of the formula (I-R)) with a selectivity of 60 to 100%, preferably 80 to 100%, in particular 90 to 100%, very particularly preferably 95 to 100%, where the particular (S) compound is preferably present with an enantioselectivity of in each case more than 50% ee, preferably 60 to 100% ee, in particular 80 to 100% ee, very particularly 90 to 100% ee, most preferably 95 to 100% ee, based on the total content of (S) compound in question.

Accordingly, the present invention relates in particular to compounds of the formula (I) in which the stereochemical configuration on the sulfur atom(s) marked by (*) is present with a stereochemical purity of 60 to 100% (S), preferably 80 to 100% (S), in particular 90 to 100% (S), very particularly 95 to 100% (S).

Depending on the type and attachment of the substituents, the compounds of the formula (I) may contain further centers of chirality in addition to the sulfur atom marked (*) in formula (I), in which case they are then present as stereoisomers. In the context of the present invention, the definition of the formula (I) comprises all stereoisomers, such as enantiomers, diasteromers and Z and E isomers, defined by their specific spatial form, i.e. the present invention comprises both the pure stereoisomers and less pure mixtures thereof. Here, preference is given in particular to compounds which, at the sulfur atom marked (*), have a stereochemical purity of from 60 to 100% (S), preferably from 80 to 100% (S), in particular from 90 to 100% (S), very particularly from 95 to 100% (S), and, at the remaining futher stereocenters, are present in racemic form or in a more or less pronounced stereochemical purity.

If, for example, one or more alkenyl groups are present, there may be diastereomers (Z and E isomers).

If, for example, one or more asymmetric carbon atoms are present, there may be enantiomers and diastereomers.

Corresponding stereoisomers may be obtained from the mixtures resulting from the preparation using customary separation methods, for example by chromatographic separation techniques. It is also possible to prepare stereoisomers selectively by using stereoselective reactions employing optically active starting materials and/or auxiliaries. Accordingly, the invention also relates to all stereoisomers embraced by the formula (I) but not shown in their specific stereoform, and to their mixtures.

For the possible combinations of the various substituents of the formula (I) the general principles of the construction of of chemical compounds have to be observed, i.e. the formula (I) does not comprise any compounds known to the person skilled in the art as being chemically impossible.

The present invention furthermore provides processes for preparing corresponding compounds of the formula (I) and/or salts thereof and/or agrochemically acceptable quaternized nitrogen derivatives thereof:

a.) To prepare optically active sulfoxides of the formula (I), for example, a thioether of the formula (II)

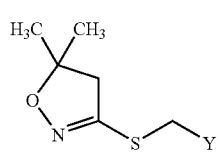

in which Y has the meaning given above for formula (I) is oxidized with one equivalent of an oxidizing agent to the sulfoxide of the formula (I).

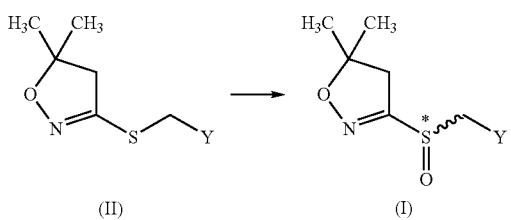

The oxidizing agents which can be used for this reaction are not subject to any particular limitations, and it is possible to use any oxidizing agent capable of oxidizing the sulfur compounds in question to sulfoxide compounds. Oxidizing agents suitable for preparing the sulfoxides are inorganic peroxides, such as, for example, hydrogen peroxide, sodium metaperiodate, organic peroxides, such as, for example, tert-butyl hydroperoxide, or organic peracids, such as peracetic acid or, preferably, 3-chloroperbenzoic acid. The reaction can be carried out in halogenated hydrocarbons, for example dichloromethane, 1,2-dichloroethane, an alcohol, such as, for example, methanol, or in dimethylformamide, water or acetic acid, or in a mixture of the solvents mentioned above. The reaction can be carried out in a temperature range of between −80° C. and 120° C., preferably between −20° C. and 50° C. Such processes are known in the literature and described, for example, in J. Org. Chem., 58 (1993) 2791, J. Org. Chem., 68 (2003) 3849 and J. Heterocyclic Chem., 15 (1978) 1361, any relevant disclosure is incorporated by reference into the present invention.

The preparation of the thioether of the formula (II) is known, for example, from WO 01/12613 A, WO 02/62770 A, WO 03/00686 A and WO 03/10165 A.

b) Compounds of the formula (I) can additionally be prepared by processes as described, for example, in WO 2001/012613, WO 2002/062770, WO 2003/000686, WO 2004/013106, WO 2006/024820, WO 2007/003294 and WO 2007/003295.

c) The enantioselective synthesis of chiral sulfoxides of the formula (I) in optically enriched or pure form can be carried out from thio compounds of the formula (II) using methods as described, for example, in Chem. Rev., 103 (2003) 3651-3705 and in the literature cited therein. The corresponding disclosure of this literature reference is incorporated into the present invention by way of reference. Here, in each individual case, the absolute configuration of the product depends on the structure of the optically active catalyst.

Corresponding salts can be prepared in a manner known per se to the person skilled in the art.

Compounds of the formula (Ia)

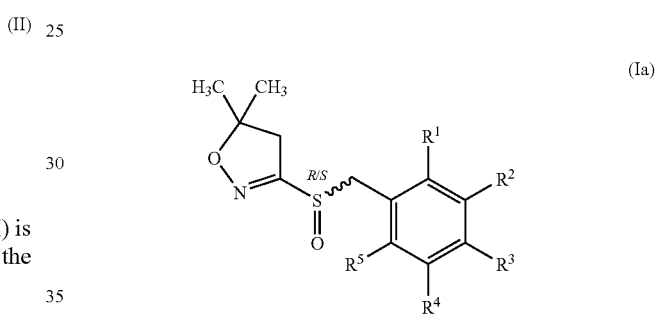

consist of a mixture of the respective enantiomers (Ia-S) and (Ia-R) which are chiral at the sulfoxide function

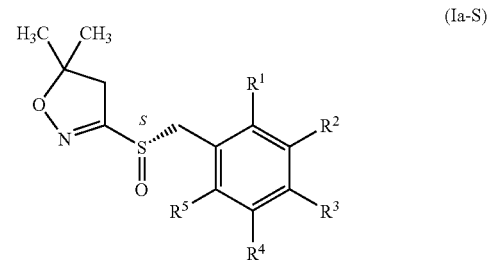

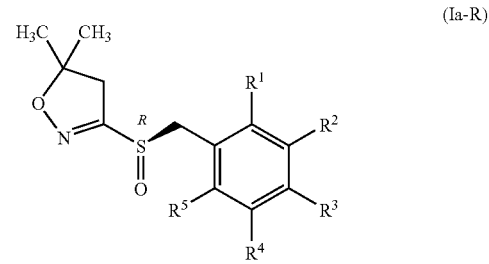

where the radicals $R^1$, $R^2$, $R^3$, $R^4$ and $R^5$ have the meanings given above for the formula (I).

Compounds of the formula (Ib)

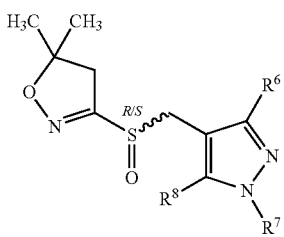

consist of a mixture of the respective enantiomers (Ib-S) and (Ib-R) which are chiral at the sulfoxide function

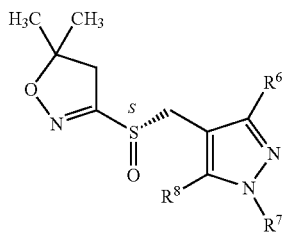

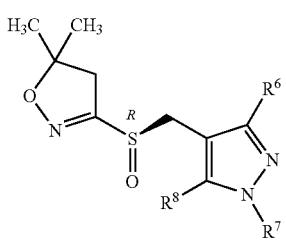

where the radicals $R^6$, $R^7$ and $R^8$ have the meanings given above for the formula (I).

Suitable for preparing enantiomers of the formula (I) are, in addition to enantioselective syntheses, also customary methods for the separation of racemates (cf. textbooks of stereochemistry).

Racemic mixtures, for example of optically active sulfoxides of the formula (I), can be separated by known processes. Such methods for the separation of racemates are described in textbooks of stereochemistry, for example in "Basic Organic Stereochemistry" (Eds.: Eliel, Ernest L.; Wilen, Samuel H.; Doyle, Michael P.; 2001; John Wiley & Sons) and "Stereochemisty of Organic Compounds (Eds.: Eliel, Ernest L.; Wilen, Samuel H.; Mander, Lewis N.; 1994; John Wiley & Sons), the relevant disclosure of which is incorporated by reference into the present invention. Suitable for this purpose are, for example, adduct formation with an optically active auxiliary, separation of the diastereomeric adducts into the corresponding diastereomers, for example by crystallization, chromatographic methods, especially column chromatography and high pressure liquid chromatography, distillation, if appropriate under reduced pressure, extraction and other methods and subsequent cleavage of the diastereomers to afford the enantiomers. Suitable for preparative amounts or on an industrial scale are processes such as the crystallization of diastereomeric salts which can be obtained from the compounds (I) using optically active acids and, if appropriate, provided that acidic groups are present, using optically active bases.

Optically active acids which are suitable for racemate separation by crystallization of diastereomeric salts are, for example, camphorsulfonic acid, camphoric acid, bromocamphorsulfonic acid, quinic acid, tartaric acid, dibenzoyltartaric acid and other analogous acids; suitable optically active bases are, for example, quinine, cinchonine, quinidine, brucine, 1-phenylethylamine and other analogous bases.

The crystallizations are then in most cases carried out in aqueous or aqueous-organic solvents, where the diastereomer which is less soluble precipitates first, if appropriate after seeding. One enantiomer of the compound of the formula (I) is then liberated from the precipitated salt, or the other is liberated from the crystals, by acidification or using a base.

Furthermore, racemates can be separated chromatographically using chiral stationary phases. Such enantiomer separations can be carried out in the mg to 100 kg range using preparative HPLC units operated batch-wise or continuously.

The "inert solvents" referred to in the above process variants are in each case solvents which are inert under the particular reacton conditions, i.e. do not react with the starting materials in particular, but need not be inert under all reaction conditions.

Libraries of compounds of the formula (I) and/or salts thereof which can be synthesized by the aforementioned reactions can also be prepared in a parallel manner, it being possible for this to take place in a manual, partly automated or completely automated manner. In this connection, it is, for example, possible to automate the reaction procedure, the work-up or the purification of the products and/or intermediates. Overall, this is understood as meaning a procedure as described, for example, by D. Tiebes in Combinatorial Chemistry—Synthesis, Analysis, Screening (editor Günther Jung), Verlag Wiley 1999, on pages 1 to 34.

For the parallel reaction procedure and work-up, it is possible to use a series of commercially available instruments, for example Calpyso reaction blocks from Barnstead International, Dubuque, Iowa 52004-0797, USA or reaction stations from Radleys, Shirehill, Saffron Walden, Essex, CB 11 3AZ, England or MultiPROBE Automated Workstations from Perkin Elmer, Waltham, Mass. 02451, USA. For the parallel purification of compounds of the formula (I) and salts thereof or of intermediates produced during the preparation, there are available, inter alia, chromatography apparatuses, for example from ISCO, Inc., 4700 Superior Street, Lincoln, Nebr. 68504, USA.

The apparatuses listed lead to a modular procedure in which the individual process steps are automated, but between the process steps manual operations have to be carried out. This can be circumvented by using partly or completely integrated automation systems in which the respective automation modules are operated, for example, by robots. Automation systems of this type can be acquired, for example, from Caliper, Hopkinton, Mass. 01748, USA.

The implementation of single or several synthesis steps can be supported through the use of polymer-supported reagents/ scavenger resins. The specialist literature describes a series of experimental protocols, for example in Chem Files, Vol. 4, No. 1, Polymer-Supported Scavengers and Reagents for Solution-Phase Synthesis (Sigma-Aldrich).

Besides the methods described here, the preparation of compounds of the formula (I) and salts thereof can take place completely or partially by solid-phase supported methods. For this purpose, individual intermediates or all intermediates in the synthesis or a synthesis adapted for the corresponding procedure are bonded to a synthesis resin. Solid-phase supported synthesis methods are sufficiently described in the specialist literature, e.g. Barry A. Bunin in "The Combinatorial Index", Verlag Academic Press, 1998 and Combinatorial Chemistry—Synthesis, Analysis, Screening (editor Günther Jung), Verlag Wiley, 1999. The use of solid-phase supported synthesis methods permits a series of protocols known in the literature, which again can be carried out manually or in an automated manner. For example, the "teabag method" (Houghten, U.S. Pat. No. 4,631,211; Houghten et al., Proc. Natl. Acad. Sci., 1985, 82, 5131-5135), in which products from IRORI, 11149 North Torrey Pines Road, La Jolla, Calif. 92037, USA, are employed, may be semiautomated. The automation of solid-phase-supported parallel syntheses is performed successfully, for example, by apparatuses from Argonaut Technologies, Inc., 887 Industrial Road, San Carlos, Calif. 94070, USA or MultiSynTech GmbH, Wullener Feld 4, 58454 Witten, Germany. The reactions can be carried out, for example, by means of IRORI technology in microreactors from Nexus Biosystems, 12140 Community Road, Poway, Calif. 92064, USA.

Both on a solid phase and in liquid phase can the procedure of individual or several synthesis steps be supported through the use of microwave technology. The specialist literature describes a series of experimental protocols, for example in Microwaves in Organic and Medicinal Chemistry (editor C. O. Kappe and A. Stadler), Verlag Wiley, 2005.

The preparation according to the process described here produces compounds of the formula (I) and their salts in the form of substance collections which are called libraries. The present invention also provides libraries which comprise at least two compounds of the formula (I) and their salts.

On account of the herbicidal property of the compounds of the formula (I), the invention also further provides the use of the compounds of the formula (I) according to the invention as herbicides for controlling harmful plants.

The compounds of the formula (I) according to the invention and their salts, also referred to synonymously below together as compounds of the formula (I), have excellent herbicidal efficacy against a broad spectrum of economically important monocotyledonous and dicotyledonous harmful plants. Difficult-to-control perennial weeds which produce shoots from rhizomes, root stocks or other perennial organs are also well controlled by the active compounds. Here, it is immaterial whether the substances are applied by the presowing method, the pre-emergence method or the post-emergence method.

Specific examples may be mentioned of some representatives of the monocotyledonous and dicotyledonous weed flora which can be controlled by the compounds of the formula (I) according to the invention, without the enumeration being restricted to certain species.

On the side of the monocotyledonous weed species, e.g. *Agrostis, Alopecurus, Apera, Avena, Brachicaria, Bromus, Dactyloctenium, Digitaria, Echinochloa, Eleocharis, Eleusine, Festuca, Fimbristylis, Ischaemum, Lolium, Monochoria, Panicum, Paspalum, Phalaris, Phleum, Poa, Sagittaria, Scirpus, Setaria, Sphenoclea*, and also *Cyperus* species predominantly from the annual group and on the sides of the perennial species *Agropyron, Cynodon, Imperata* and *Sorghum* and also perennial *Cyperus* species are well controlled.

In the case of dicotyledonous weed species, the spectrum of action extends to species such as, for example, *Galium, Viola, Veronica, Lamium, Stellaria, Amaranthus, Sinapis, Ipomoea, Matricaria, Abutilon* and *Sida* on the annual side, and *Convolvulus, Cirsium, Rumex* and *Artemisia* in the case of the perennial weeds. Moreover, herbicidal effect in the case of dicotyledonous weeds such as *Ambrosia, Anthemis, Carduus, Centaurea, Chenopodium, Cirsium, Convolvulus, Datura, Emex, Galeopsis, Galinsoga, Lepidium, Lindernia, Papaver, Portlaca, Polygonum, Ranunculus, Rorippa, Rotala, Seneceio, Sesbania, Solanum, Sonchus, Taraxacum, Trifolium, Urtica* and *Xanthium* is observed.

If the compounds of the formula (I) according to the invention are applied to the soil surface before germination, the weed seedlings are either prevented completely from emerging or else the weeds grow until they have reached the cotyledon stage, but then their growth stops, and, eventually, after three to four weeks have elapsed, they die completely.

If the active compounds of the formula (I) are applied post-emergence to the green parts of the plants, growth likewise stops drastically a very short time after the treatment, and the weed plants remain at the growth stage of the point of time of application, or they die completely after a certain time, so that in this manner competition by the weeds, which is harmful to the crop plants, is eliminated very early and in a sustained manner.

Although the compounds of the formula (I) according to the invention have excellent herbicidal activity in respect of monocotyledonous and dicotyledonous weeds, crop plants of economically important crops, such as, for example, wheat, barley, rye, rice, corn, sugarbeet, cotton, oilseed rape and soybean, are only damaged negligibly, if at all. This is why the present compounds are highly suitable for the selective control of unwanted plant growth in agriculturally useful plants.

In addition, the substances of the formula (I) according to the invention have excellent growth regulatory properties in crop plants. They engage in the plant metabolism in a regulatory fashion and can therefore be employed for the influencing, in a targeted manner, of plant constituents and for facilitating harvesting, such as, for example, by triggering desiccation and stunted growth. Moreover, they are also suitable for generally controlling and inhibiting unwanted vegetative growth without destroying the plants in the process. Inhibiting the vegetative growth plays an important role in many monocotyledonous and dicotyledonous crops since lodging can be reduced, or prevented completely, hereby.

By virtue of their herbicidal and plant-growth-regulatory properties, the active compounds can also be employed for controlling harmful plants in crops of known genetically modified plants or genetically modified plants still to be developed. In general, the transgenic plants are distinguished by especially advantageous properties, for example by resistances to certain pesticides, mainly certain herbicides, resistances to plant diseases or causative organisms of plant diseases, such as certain insects or microorganisms such as fungi, bacteria or viruses. Other specific characteristics relate, for example, to the harvested material with regard to quantity, quality, storeability, composition and specific constituents. Thus, transgenic plants are known whose starch content is increased, or whose starch quality is altered, or those where the harvested material has a different fatty acid composition. Other particular properties may be tolerance or resistance to abiotic stressors, for example heat, low temperatures, drought, salinity and ultraviolet radication.

It is preferred to use the compounds of the formula (I) according to the invention or salts thereof in economically important transgenic crops of useful plants and ornamental plants, for example of cereals such as wheat, barley, rye, oats, sorghum and millet, rice, cassava and corn or else crops of sugar beet, cotton, soybean, oilseed rape, potato, tomato, peas and other vegetables.

It is preferred to be able to employ the compounds of the formula (I) as herbicides in crops of useful plants which are resistant, or have been made resistant by recombinant means, to the phytotoxic effects of the herbicides.

Conventional methods of generating novel plants which have modified properties in comparison to plants occurring to date consist, for example, in traditional breeding methods and the generation of mutants. Alternatively, novel plants with altered properties can be generated with the aid of recombinant methods (see, for example, EP 0221044, EP 0131624). For example, the following have been described in several cases:

recombinant modifications of crop plants for the purposes of modifying the starch synthesized in the plants (for example WO 92/011376, WO 92/014827, WO 91/019806), transgenic crop plants which are resistant to certain herbicides of the glufosinate type (cf., for example, EP 0242236, EP 0242246) or the glyphosate type (WO 92/000377) or the sulfonylurea type (EP 0257993, U.S. Pat. No. 5,013,659), transgenic crop plants, for example cotton, which is capable of producing *Bacillus thuringiensis* toxins (Bt toxins), which make the plants resistant to certain pests (EP 0142924, EP 0193259), transgenic crop plants with a modified fatty acid composition (WO 91/013972).

genetically modified crop plants with novel constituents or secondary metabolites, for example novel phytoalexins, which bring about an increased disease resistance (EP 0309862, EP 0464461), genetically modified plants with reduced photorespiration which feature higher yields and higher stress tolerance (EP 0305398), transgenic crop plants which produce pharmaceutically or diagnostically important proteins ("molecular pharming"), transgenic crop plants which are distinguished by higher yields or better quality, transgenic crop plants which are distinguished by a combination, for example of the abovementioned novel properties ("gene stacking").

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg. oder Christou, "Trends in Plant Science" 1 (1996) 423-431).

To carry out such recombinant manipulations, nucleic acid molecules which allow mutagenesis or sequence changes by recombination of DNA sequences can be introduced into plasmids. For example, base substitutions can be carried out, part-sequences can be removed, or natural or synthetic sequences may be added with the aid of standard methods. To link the DNA fragments with one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, N.Y.; or Winnacker "Gene and Klone", V C H Weinheim 2nd ed., 1996.

For example, the generation of plant cells with a reduced activity of a gene product can be achieved by expressing at least one corresponding antisense RNA, a sense RNA for achieving a cosuppression effect or by expressing at least one suitably constructed ribozyme which specifically cleaves transcripts of the abovementioned gene product.

To this end, it is possible to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the coding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants can be plants of any desired plant species, i.e. not only monocotyledonous, but also dicotyledonous, plants.

Thus, transgenic plants can be obtained whose properties are altered by overexpression, suppression or inhibition of homologous (=natural) genes or gene sequences or the expression of heterologous (=foreign) genes or gene sequences.

It is preferred to employ the compounds of the formula (I) according to the invention in transgenic crops which are resistant to growth regulators such as, for example, dicamba, or against herbicides which inhibit essential plant enzymes, for example acetolactate synthases (ALS), EPSP synthases, glutamine synthases (GS) or hydroxyphenylpyruvate dioxygenases (HPPD), or against herbicides from the group of the sulfonylureas, glyphosate, glufosinate or benzoylisoxazoles and analogous active substances.

When the active compounds of the formula (I) according to the invention are used in transgenic crops, effects are frequently observed—in addition to the effects on harmful plants which can be observed in other crops—which are specific for the application in the transgenic crop in question, for example a modified or specifically widened spectrum of weeds which can be controlled, modified application rates which may be employed for application, preferably good combinability with the herbicides to which the transgenic crop is resistant, and an effect on growth and yield of the transgenic crop plants.

The invention therefore also relates to the use of the compounds of the formula (I) according to the invention as herbicides for controlling harmful plants in transgenic crop plants.

The compounds of the formula (I) can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical technology], Volume 7, C. Hanser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active ethylene oxide adducts], Wiss. Verlagsgesell., Stuttgart 1976; Winnacker-Küchler, "Chemische Technologie", Volume 7, C. Hanser Verlag Munich, 4th Ed. 1986.

Based on these formulations, it is also possible to produce combinations with other pesticidally active compounds, such as, for example, insecticides, acaricides, herbicides, fungicides, and also with safeners, fertilizers and/or growth regulators, for example in the form of a finished formulation or as a tank mix.

Wettable powders are preparations which can be dispersed uniformly in water and, as well as the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleylmethyltauride. To prepare the wettable powders, the herbicidally active compounds are ground finely, for example in customary apparatus such as hammer mills, blower mills and air-jet mills and simultaneously or subsequently mixed with the formulation assistants.

Emulsifiable concentrates are prepared by dissolving the active compound in an organic solvent, for example butanol, cyclohexanone, dimethylformamide, xylene or else relatively high-boiling aromatics or hydrocarbons or mixtures of the organic solvents with addition of one or more surfactants of the ionic and/or nonionic type (emulsifiers). The emulsifiers used may, for example, be: alkylarylsulfonic calcium salts, such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, such as, for example, sorbitan fatty acid esters, or polyoxyethylene sorbitan esters, such as, for example, polyoxyethylene sorbitan fatty acid esters.

Dusts are obtained by grinding the active compound with finely distributed solid substances, for example talc, natural clays, such as kaolin, bentonite and pyrophillite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, e.g. oil-in-water emulsions (EW), can be prepared, for example, by means of stirrers, colloid mills and/or static mixers using aqueous organic solvents and if appropriate surfactants, as have for example already been listed above in connection with the other types of formulation.

Granules can be prepared either by spraying the active compound onto granular inert material capable of adsorption or by applying active compound concentrates to the surface of carrier substances, such as sand, kaolinites or granular inert material, by means of adhesives, for example polyvinyl alcohol, sodium polyacrylate or mineral oils. Suitable active compounds can also be granulated in the manner customary for the preparation of fertilizer granules—if desired as a mixture with fertilizers.

Water-dispersible granules are prepared generally by the customary processes such as spray-drying, fluidized bed granulation, pan granulation, mixing with high-speed mixers and extrusion without solid inert material.

For the preparation of pan, fluidized bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th Ed., McGraw-Hill, New York 1973, p. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations comprise generally from 0.1 to 99% by weight, in particular from 0.1 to 95% by weight, of active compound of the formula (I).

In wettable powders, the active compound concentration is, for example, from about 10 to 90% by weight, the remainder to 100% by weight consisting of customary formulation components. In the case of emulsifiable concentrates, the active compound concentration can be from about 1 to 90, preferably from 5 to 80, % by weight. Dust-type formulations contain from 1 to 30% by weight of active compound, preferably usually from 5 to 20% by weight of active compound; sprayable solutions contain from about 0.05 to 80% by weight, preferably from 2 to 50% by weight of active compound. In the case of water-dispersible granules, the active compound content depends partially on whether the active compound is present in liquid or solid form and on which granulation auxiliaries, fillers, etc., are used. In the water-dispersible granules, the content of active compound is, for example, between 1 and 95% by weight, preferably between 10 and 80% by weight.

In addition, the active compound formulations mentioned optionally comprise the respective customary adhesives, wetting agents, dispersants, emulsifiers, penetrants, preservatives, antifreeze agents and solvents, fillers, carriers and dyes, defoamers, evaporation inhibitors and agents which influence the pH and the viscosity.

The compounds of the formula (I) or salts thereof can be employed as such or in the form of their preparations (formulations) combined with other pesticidally active compounds, such as, for example, insecticides, acaricides, nematicides, herbicides, fungicides, safeners, fertilizers and/or growth regulators, for example as finished formulation or as tank mixes. Combination partners which can be used for the active compounds of the formula (I) according to the invention in mixture formulations or in the tank mix are, for example, known active compounds whose action is based on the inhibition of, for example, acetolactate synthase, acetyl-coenzyme-A carboxylase, PS I, PS II, HPPDO, phytoene desaturase, protoporphyrinogen oxidase, glutamine synthetase, 5-enolpyruvylshikimate 3-phosphate synthetase or cellulose biosynthesis. Such compounds and also other compounds that can be used, some of which having an unknown or other mechanism of action, are described, for example, in Weed Research 26, 441-445 (1986), or "The Pesticide Manual", 11th edition 1997 (hereinbelow also referred to abbreviated as "PM") and 12th edition 2000, The British Crop Protection Council and the Royal Soc. of Chemistry (publisher), and the literature cited therein. Herbicides known from the literature which can be combined with the compounds of the formula (I) are, for example, the following active compounds (note: the compounds are referred to either by the "common name" in accordance with the International Organization for Standardization (ISO) or by the chemical name, if appropriate together with a customary code number):

acetochlor; acifluorfen(-sodium); aclonifen; AKH 7088, i.e. [[[1-[5-[2-chloro-4-(trifluoromethyl)phenoxy]-2-nitrophenyl]-2-methoxyethylidene]amino]oxy]acetic acid and methyl[[[1-[5-[2-chloro-4-(trifluoromethyl)phenoxy]-2-nitrophenyl]-2-methoxyethylidene]amino]oxy]acetate; acrolein; alachlor; alloxydim(-sodium); ametryn; amicarbazone, amidochlor, amidosulfuron; aminopyralid, amitrol; AMS, i.e. ammonium sulfamate; anilofos; asulam; atraton; atrazine; azafenidin, azimsulfuron (DPX-A8947); aziprotryn; barban; BAS 516 H, i.e. 5-fluoro-2-phenyl-4H-3,1-benzoxazin-4-one; BCPC; beflubutamid, benazolin(-ethyl); benfluralin; benfuresate; bensulfuron(-methyl); bensulide; bentazone; benzfendizone; benzobicyclon, benzofenap; benzofluor; benzoylprop(-ethyl); benzthiazuron; bifenox; bialaphos; bifenox; bispyribac(-sodium), borax; bromacil; bromobutide; bromofenoxim; bromoxynil; bromuron; buminafos; busoxinone; butachlor; butafenacil, butamifos; butenachlor; buthidazole; butralin; butroxydim, butylate; cacodylic acid; calcium chlorate; cafenstrole (CH-900); carbetamide; carfentrazone(-ethyl); caloxydim, CDAA, i.e. 2-chloro-N,N-di-2-propenylacetamide; CDEC, i.e. 2-chlorallyl diethyldithiocarbamate; chlorflurenol(-methyl); chlomethoxyfen; clethodim; clomeprop; chloramben; chlorazifop-butyl, chlormesulon; chlorbromuron; chlorbufam; chlorfenac; chlorflurecol-methyl; chloridazon; chlorimuron(-ethyl); chloroacetic acid; chlornitrofen; chlorotoluron; chloroxuron; chlorpropham; chlorsulfuron; chlorthal(-dimethyl); chlorthiamid; chlortoluron, cinidon(-methyl and -ethyl), cinmethylin; cinosulfuron; cisanilide; clefoxydim, clethodim; clodinafop and its ester derivatives (for example clodinafop-propargyl); clomazone; clomeprop; cloproxydim; clopyralid; clopyrasulfuron(-methyl); cloransulam(-methyl), cresol; cumyluron (JC 940); cyanamide; cyanazine; cycloate; cyclosulfamuron (AC 104); cycloxydim; cycluron; cyhalofop and its ester derivatives (for example the butyl ester, DEH-112); cyperquat; cyprazine; cyprazole; daimuron; 2,4-D, 2,4-DB, 3,4-DA, 3,4-DB, 2,4-DEB, dalapon; dazomed; desmedipham; desmetryn; di-allate; dicamba; dichlobenil; ortho-dichlorobenzene; para-dichlorobenzene; dichlorprop; dichlorprop-P; diclofop and its esters, such as diclofop-methyl; diclosulam, diethatyl(-ethyl); difenoxuron; difenzoquat; difenzoquat-methylsulfate; diflufenican; diflufenzopyr, dimefuron; dimepiperate, dimethachlor; dimethametryn; dimethenamid (SAN-582H); dimethenamid-P; dimethazone, dimexyflam, dimethipin; dimethylarsinic acid; dimetrasulfuron, dinitramine; dinoseb; dinoterb; diphenamid; dipropetryn; diquat; diquat-dibromide; dithiopyr; diuron; DNOC; 3,4-DP; DSMA; EBEP; eglinazine-ethyl; EL77, i.e. 5-cyano-1-(1,1-dimethylethyl)-N-methyl-1H-pyrazole-4-carboxamide; endothal; epoprodan, EPTC; esprocarb; ethalfluralin; ethametsulfuron(-methyl); ethidimuron; ethiozin; ethofumesate; ethoxyfen and its esters (for example the ethyl ester, HN-252); ethoxysulfuron, etobenzanid (HW 52); F5231, i.e. N-[2-chloro-4-fluoro-5-[4-(3-fluoropropyl)-4,5-dihydro-5-oxo-1H-tetrazol-1-yl]phenyl]ethanesulfonamide; fenoprop; fenoxan, fenoxaprop and fenoxaprop-P and also their esters, for example fenoxaprop-P-ethyl and fenoxaprop-ethyl; fenoxydim; fentrazamide, fenuron; ferrous sulfate; flamprop(-methyl or -isopropyl or -isopropyl-L); flazasulfuron; floazulate, florasulam, fluazifop and fluazifop-P and their esters, for example fluazifop-butyl and fluazifop-P-butyl; fluazolate; flucarbazone(-sodium), flucetosulfuron; fluchloralin; flufenacet; flufenpyr(-ethyl); flumetsulam; flumeturon; flumiclorac(-pentyl), flumioxazin (S-482); flumipropyn; fluometuron, fluorochloridone, fluorodifen; fluoroglycofen(-ethyl); flupoxam (KNW-739); flupropacil (UBIC-4243); flupropanate, flupyrsulfuron(-methyl or -sodium), flurenol(-butyl), fluridone; flurochloridone; fluroxypyr(-meptyl); flurprimidol; flurtamone; fluthiacet(-methyl) (KIB-9201); fluthiamide; fomesafen; foramsulfuron; fosamine; furyloxyfen; glufosinate(-ammonium); glyphosate (-isopropylammonium); halosafen; halosulfuron(-methyl) and its esters (for example the methyl ester, NC-319); haloxyfop and its esters; haloxyfop-P (=R-haloxyfop) and its esters; HC-252; hexazinone; imazamethabenz(-methyl); imazapyr; imazaquin and salts, such as the ammonium salt; imazamethapyr, imazamox, imazapic, imazethamethapyr; imazethapyr; imazosulfuron; indanofan, iodomethane; iodosulfuron(methylsodium); ioxynil; isocarbamid; isopropalin; isoproturon; isouron; isoxaben; isoxachlortole, isoxaflutole, isoxapyrifop; karbutilate; lactofen; lenacil; linuron; MAA; MAMA; MCPA; MCPA-2-ethylhexyl; MCPA-thioethyl; MCPB; mecoprop; mecoprop-P; mefenacet; mefluidid; mesosulfuron(-methyl); mesotrione, metamifop; metamitron, metazachlor; methabenzthiazuron; metham; methazole; methoxyphenone; methylarsonic acid; methyldymron; methyl isothiocyanate; metabenzuron, metamifop; methobenzuron; metobromuron; (alpha-)metolachlor; S-metolachlor; metosulam (XRD 511); metoxuron; metribuzin; metsulfuron-methyl; MK-616; MH; molinate; monalide; monocarbamide dihydrogensulfate; monolinuron; monuron; MSMA; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; nonanoic acid; norflurazon; oleic acid (fatty acid); orbencarb; orthosulfamuron; oryzalin; oxadiargyl (RP-020630); oxadiazon; oxasulfuron, oxaziclomefone, oxyfluorfen; paraquat; paraquat-dichloride; pebulate; pelargonic acid, pendimethalin; penoxsulam; pentachlorophenol; pentanochlor; pentoxazone, perfluidone; phenisopham; phenmedipham(ethyl); pethoxamid; picloram; picolinafen, pinoxaden, piperophos; piributicarb; pirifenop-butyl; pretilachlor; primisulfuron(-methyl); potassium arsenite; potassium azide; procarbazone-(sodium), procyazine; prodiamine; profluazol; proflluralin; profoxydim; proglinazine(-ethyl); prometon; prometryn; propachlor; propanil; propaquizafop and its esters; propazine; propham; propisochlor; propoxycarbazone(-sodium) (BAY MKH 6561); propyzamide; prosulfalin; prosulfocarb; prosulfuron (CGA-152005); prynachlor; pyraclonil; pyraflufen(-ethyl), pyrasulfotole; pyrazolinate; pyrazon; pyrazosulfuron(-ethyl); pyrazoxyfen; pyribambenz-isopropyl; pyribenzoxim, pyributicarb, pyridafol, pyridate; pyriftalid; pyrimidobac(-methyl), pyrimisulfan, pyrithiobac(-sodium) (KIH-2031); pyroxasulfone; pyroxofop and its esters (for example the propargyl ester); pyroxsulam (triflosulam); quinclorac; quinmerac; quinoclamine, quinofop and its ester derivatives, quizalofop and quizalofop-P and their ester derivatives, for example quizalofop-ethyl; quizalofop-P-tefuryl and -ethyl; renriduron; rim-sulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and methyl 2-[[7-[2-chloro-4-(trifluoromethyl)phenoxy]-2-naphthalenyl]oxy] propanoate; SMA; sodium arsenite; sodium azide; sodium chlorate; sulcotrione, sulfentrazon (FMC-97285, F-6285); sulfazuron; sulfometuron(-methyl); sulfosate (ICI-A0224); sulfosulfuron, 2,3,6-TBA; TCA(sodium); tebutam (GCP-5544); tebuthiuron; tefuryltrione, tembotrione, tepraloxydim, terbacil; terbucarb; terbuchlor; terbumeton; terbuthylazine; terbutryn; TFH 450, i.e. N,N-diethyl-3-[(2-ethyl-6-meth-ylphenyl)sulfonyl]-1H-1,2,4-triazole-1-carboxamide; the-nylchlor (NSK-850); thiafluamide, thiazafluron; thiazopyr (Mon-13200); thidiazimin (SN-24085); thiencarbazone-methyl, thifensulfuron(-methyl); thiobencarb; tiocarbazil; tralkoxydim; tri-allate; triasulfuron; triaziflam, triazofena-mide; tribenuron(-methyl); tricamba; triclopyr; tridiphane; trietazine; trifloxysulfuron(sodium); trifluralin; triflusulfuron and esters (for example the methyl ester, DPX-66037); trihy-droxytriazine; trimeturon; tritosulfuron; tropamezone; tsito-def; vernolate; [3-[2-chloro-4-fluoro-5-(1-methyl-6-trifluo-romethyl-2,4-dioxo-1,2,3,4-tetrahydropyrimidin-3-yl) phenoxy]-2-pyridyloxy]acetic acid ethyl ester; WL 110547, i.e. 5-phenoxy-1-[3-(trifluoromethyl)phenyl]-1H-tetrazole; UBH-509; D-489; LS 82-556, i.e. [(S)-3-N-(methylbenzyl) carbamoyl-5-propionyl-2,6-lutidine]; KPP-300; NC-324; NC-330; KH-218; DPX-N8189; SC-0774; DOWCO-535; DK-8910; V-53482; PP-600; MBH-001; ET-751, i.e. h ethyl [2-chloro-5-(4-chloro-5-difluoromethoxy-1-methyl-1H-pyrazol-3-yl)-4-fluorophenoxy]acetate; KIH-6127, i.e. pyriminobac-methyl; KIH-2023, i.e. bispyribac-sodium; and SYP-249, i.e ethyl 2-{2-nitro-5-[(2-chloro-4-trifluorom-ethyl)phenoxy]benzoxy}-3-methyl-3-butenoate; SYN-523.

Of particular interest is the selective control of harmful plants in crops of useful plants and ornamentals. Although the compounds of the formula (I) according to the invention have already demonstrated very good to adequate selectivity in a large number of crops, in principle, in some crops and in particular also in the case of mixtures with other, less selective herbicides, phytotoxicities on the crop plants may occur. In this connection, combinations of compounds of the formula (I) according to the invention are of particular interest which comprise the compounds of the formula (I) or their combinations with other herbicides or pesticides and safeners. The safeners, which are used in an antidotically effective amount, reduce the phytotoxic side effects of the herbicides/pesticides employed, for example in economically important crops, such as cereals (wheat, barley, rye, corn, rice, millet), sugar beet, sugar cane, oilseed rape, cotton and soybeans, preferably cereals. The following groups of compounds are suitable, as safeners for the compounds (I) alone or else in their combinations with further pesticides:

a) compounds of the formulae (S-II) to (S-IV)
where the symbols and indices have the following meanings:

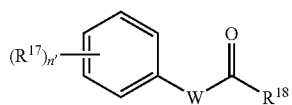
(S-II)

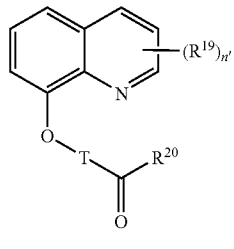
(S-III)

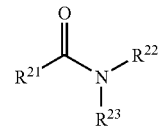
(S-IV)

n' is a natural number from 0 to 5, preferably from 0 to 3;
T is a ($C_1$- or $C_2$)-alkanediyl chain which is unsubstituted or substituted by one or two ($C_1$-$C_4$)-alkyl radicals or by [($C_1$-$C_3$)-alkoxy]carbonyl;
W is an unsubstituted or substituted divalent heterocyclic radical from the group consisting of partially unsaturated or aromatic five-membered heterocycles having 1 to 3 hetero ring atoms of the type N or O, where at least one nitrogen atom and at most one oxygen atom is present in the ring, preferably a radical from the group consisting of (W1) to (W4),

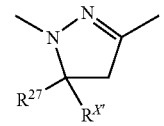
(W1)

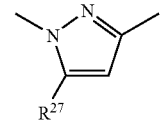
(W2)

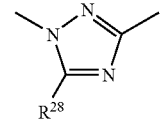
(W3)

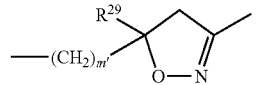
(W4)

m' is 0 or 1;
$R^{17}$, $R^{19}$ are identical or different and are halogen, ($C_1$-$C_4$)-alkyl, ($C_1$-$C_4$)-alkoxy, nitro or ($C_1$-$C_4$)-haloalkyl;
$R^{18}$, $R^{20}$ are identical or different and are $OR^{24}$, $SR^{24}$ or $NR^{24}R^{25}$ or a saturated or unsaturated 3- to 7-membered heterocycle having at least one nitrogen atom and up to 3 heteroatoms, preferably from the group consisting of O and S, which is attached via the nitrogen atom to the carbonyl group in (S-II) or (S-III) and is unsubstituted or substituted by radicals from the group consisting of ($C_1$-$C_4$)-alkyl, ($C_1$-$C_4$)-alkoxy or optionally substituted phenyl, preferably a radical of the formula $OR^{24}$, $NHR^{25}$ or $N(CH_3)_2$, in particular of the formula $OR^{24}$;
$R^{24}$ is hydrogen or an unsubstituted or substituted aliphatic hydrocarbon radical having preferably a total of 1 to 18 carbon atoms;

$R^{25}$ is hydrogen, $(C_1-C_6)$-alkyl, $(C_1-C_6)$-alkoxy or substituted or unsubstituted phenyl;

$R^{x-}$ is H, $(C_1-C_8)$-alkyl, $(C_1-C_8)$-haloalkyl, $(C_1-C_4)$-alkoxy-$(C_1-C_8)$-alkyl, cyano or $COOR^{26}$ where $R^{26}$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkylsilyl;

$R^{27}, R^{28}, R^{29}$ are identical or different and are hydrogen, $(C_1-C_8)$-alkyl, $(C_1-C_8)$-haloalkyl, $(C_3-C_{12})$-cycloalkyl or substituted or unsubstituted phenyl;

$R^{21}$ is $(C_1-C_4)$-alkyl, $(C_1-C_4)$-haloalkyl, $(C_2-C_4)$-alkenyl, $(C_2-C_4)$-haloalkenyl, $(C_3-C_7)$-cycloalkyl, preferably dichloromethyl;

$R^{22}, R^{23}$ are identical or different and are hydrogen, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$-alkyl, $(C_1-C_4)$-alkoxy-$(C_1-C_4)$-alkyl, dioxolanyl-$(C_1-C_4)$-alkyl, thiazolyl, furyl, furylalkyl, thienyl, piperidyl, substituted or unsubstituted phenyl, or $R^{22}$ and $R^{23}$ together form a substituted or unsubstituted heterocyclic ring, preferably an oxazolidine, thiazolidine, piperidine, morpholine, hexahydropyrimidine or benzoxazine ring;

b) one or more compounds from the group consisting of:

1,8-naphthalic anhydride, methyl diphenylmethoxyacetate, 1-(2-chlorobenzyl)-3-(1-methyl-1-phenylethyl)urea (cumyluron), O,O-diethyl S-2-ethylthioethyl phosphorodithioate (disulfoton), 4-chlorophenyl methylcarbamate (mephenate), O,O-diethyl O-phenyl phosphorothioate (dietholate), 4-carboxy-3,4-dihydro-2H-1-benzopyran-4-acetic acid (CL-304415, CAS-Regno: 31541-57-8), cyanomethoxyimino(phenyl)acetonitrile (cyometrinil)

1,3-dioxolan-2-ylmethoxyimino(phenyl)acetonitrile (oxabetrinil),

4'-chloro-2,2,2-trifluoroacetophenone O-1,3-dioxolan-2-ylmethyloxime (fluxofenim), 4,6-dichloro-2-phenylpyrimidine (fenclorim), benzyl 2-chloro-4-trifluoromethyl-1,3-thiazole-5-carboxylate (flurazole), 2-dichloromethyl-2-methyl-1,3-dioxolane (MG-191), N-(4-methylphenyl)-N'-(1-methyl-1-phenylethyl)urea (dymron), (2,4-dichlorophenoxy)acetic acid (2,4-D), (4-chlorophenoxy)acetic acid, (R,S)-2-(4-chloro-o-tolyloxy)propionic acid (mecoprop), 4-(2,4-dichlorophenoxy)butyric acid (2,4-DB), (4-chloro-o-tolyloxy)acetic acid (MCPA), 4-(4-chloro-o-tolyloxy)butyric acid, 4-(4-chlorophenoxy)butyric acid, 3,6-dichloro-2-methoxybenzoic acid (dicamba), 1-(ethoxycarbonyl)ethyl 3,6-dichloro-2-methoxybenzoate (lactidichlor) and their salts and esters, preferably $(C_1-C_8)$;

c) N-acylsulfonamides of the formula (S-V) and their salts,

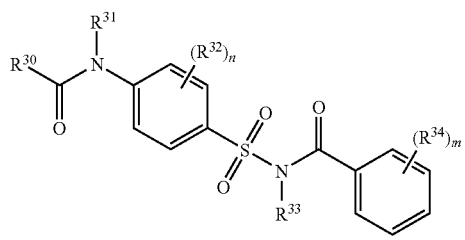

(S-V)

in which $R^{30}$ is hydrogen, a hydrocarbon radical, a hydrocarbonoxy radical, a hydrocarbonthio radical or a heterocyclyl radical which is preferably attached via a carbon atom, where each of the 4 last-mentioned radicals is unsubstituted or substituted by one or more identical or different radicals from the group consisting of halogen, cyano, nitro, amino, hydroxyl, carboxyl, formyl, carbonamide, sulfonamide and radicals of the formula $-Z^{a'}-R^{a'}$, where each hydrocarbon moiety has preferably 1 to 20 carbon atoms and a carbon-containing radical $R^{30}$ including substituents has preferably 1 to 30 carbon atoms;

$R^{31}$ is hydrogen or $(C_1-C_4)$-alkyl, preferably hydrogen, or $R^{30}$ and $R^{31}$ together with the group of the formula $-CO-N-$ are the radicals of a 3- to 8-membered saturated or unsaturated ring;

$R^{32}$ are identical or different radicals from the group consisting of halogen, cyano, nitro, amino, hydroxyl, carboxyl, formyl, $CONH_2$, $SO_2NH_2$ or a radical of the formula $-Z^{b'}-R^{b'}$;

$R^{33}$ is hydrogen or $(C_1-C_4)$-alkyl, preferably H;

$R^{34}$ are identical or different radicals from the group consisting of halogen, cyano, nitro, amino, hydroxyl, carboxyl, CHO, $CONH_2$, $SO_2NH_2$ and a radical of the formula $-Z^{c'}-R^{c'}$;

$R^{a'}$ is a hydrocarbon radical or a heterocyclyl radical, where each of the two last-mentioned radicals is unsubstituted or substituted by one or more identical or different radicals from the group consisting of halogen, cyano, nitro, amino, hydroxyl, mono- and di-$[(C_1-C_4)$-alkyl]amino, or an alkyl radical in which a plurality, preferably 2 or 3, non-adjacent $CH_2$ groups are in each case replaced by an oxygen atom;

$R^{b'}, R^{c'}$ are identical or different and are a hydrocarbon radical or a heterocyclyl radical, where each of the two last-mentioned radicals is unsubstituted or substituted by one or more identical or different radicals from the group consisting of halogen, cyano, nitro, amino, hydroxyl, phosphoryl, halo-$(C_1-C_4)$-alkoxy, mono- and di-$[(C_1-C_4)$-alkyl]amino, or an alkyl radical in which a plurality, preferably 2 or 3, non-adjacent $CH_2$ groups are in each case replaced by an oxygen atom;

$Z^{a'}$ is a divalent group of the formula $-O-$, $-S-$, $-CO-$, $-CS-$, $-CO-O-$, $-CO-S-$, $-O-CO-$, $-S-CO-$, $-SO-$, $-SO_2-$, $-NR^*-$, $-CO-NR^*-$, $-NR^*-CO-$, $-SO_2-NR^*-$ or $-NR^*-SO_2-$, where the bond indicated on the right-hand side of the divalent group in question is the bond to the radical $R^a$ and where the $R^*$ in the 5 last-mentioned radicals independently of one another are each H, $(C_1-C_4)$-alkyl or halo-$(C_1-C_4)$-alkyl;

$Z^{b'}, Z^{c'}$ independently of one another are a direct bond or a divalent group of the formula $-O-$, $-S-$, $-CO-$, $-CS-$, $-CO-O-$, $-CO-S-$, $-O-CO-$, $-S-CO-$, $-SO-$, $-SO_2-$, $-NR^*-$, $-SO_2-NR^*-$, $-NR^*-SO_2-$, $-CO-NR^*-$ or $-NR^*-$ CO—, where the bond indicated on the right-hand side of the divalent group in question is the bond to the radical $R^{b'}$ or $R^{c'}$ and where R* in the 5 last-mentioned radicals independently of one another are each H, $(C_1-C_4)$-alkyl or halo-$(C_1-C_4)$-alkyl;
n is an integer from 0 to 4, preferably 0, 1 or 2, particularly preferably 0 or 1, and
m is an integer from 0 to 5, preferably 0, 1, 2 or 3, in particular 0, 1 or 2;
d) acylsulfamoylbenzamides of the formula (S-VI), if appropriate also in salt form,

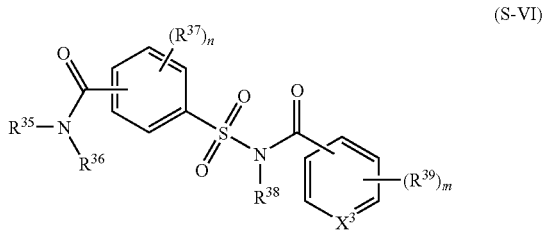

(S-VI)

in which
$X^3$ is CH or N,
$R^{35}$ is hydrogen, heterocyclyl or a hydrocarbon radical where the two last-mentioned radicals are optionally substituted by one or more identical or different radicals from the group consisting of halogen, cyano, nitro, amino, hydroxyl, carboxyl, CHO, $CONH_2$, $SO_2NH_2$ and $Z^{a'}$—$R^{a'}$;
$R^{36}$ is hydrogen, hydroxyl, $(C_1-C_6)$-alkyl, $(C_2-C_6)$-alkenyl, $(C_2-C_6)$-alkynyl, $(C_1-C_6)$-alkoxy, $(C_2-C_6)$-alkenyloxy, where the five last-mentioned radicals are optionally substituted by one or more identical or different radicals from the group consisting of halogen, hydroxyl, $(C_1-C_4)$-alkyl, $(C_1-C_4)$-alkoxy and $(C_1-C_4)$-alkylthio, or
$R^{35}$ and $R^{36}$ together with the nitrogen atom that carries them are a 3- to 8-membered saturated or unsaturated ring;
$R^{37}$ is halogen, cyano, nitro, amino, hydroxyl, carboxyl, CHO, $CONH_2$, $SO_2NH_2$ or $Z^{b'}$- $R^{b'}$;
$R^{38}$ is hydrogen, $(C_1-C_4)$-alkyl, $(C_2-C_4)$-alkenyl or $(C_2-C_4)$-alkynyl;
$R^{39}$ is halogen, cyano, nitro, amino, hydroxyl, carboxyl, phosphoryl, CHO, $CONH_2$, $SO_2NH_2$ or $Z^{c'}$—$R^{c'}$;
$R^{a'}$ is a $(C_2-C_{20})$-alkyl radical whose carbon chain is interrupted once or more than once by oxygen atoms, is heterocyclyl or a hydrocarbon radical, where the two last-mentioned radicals are optionally substituted by one or more identical or different radicals from the group consisting of halogen, cyano, nitro, amino, hydroxyl, mono- and di-[$(C_1-C_4)$-alkyl]amino;
$R^{b'},R^{c'}$ are identical or different and are a $(C_2-C_{20})$-alkyl radical whose carbon chain is interrupted once or more than once by oxygen atoms, are heterocyclyl or a hydrocarbon radical, where the two last-mentioned radicals are optionally substituted by one or more identical or different radicals from the group consisting of halogen, cyano, nitro, amino, hydroxyl, phosphoryl, $(C_1-C_4)$-haloalkoxy, mono- and di-[$(C_1-C_4)$-alkyl]amino;
$Z^{a'}$ is a divalent unit from the group consisting of O, S, CO, CS, C(O)O, C(O)S, SO, $SO_2$, $NR^{d'}$, $C(O)NR^{d'}$ and $SO_2NR^{d'}$;
$Z^{b'}$, $Z^{c'}$ are identical or different and are a direct bond or divalent unit from the group consisting of O, S, CO, CS, C(O)O, C(O)S, SO, $SO_2$, $NR^{d'}$, $SO_2NR^{d'}$ and $C(O)NR^{d'}$;
$R^{d'}$ is hydrogen, $(C_1-C_4)$-alkyl or $(C_1-C_4)$-haloalkyl;
N is an integer from 0 to 4, and
m if X=CH is an integer from 0 to 5, and if X=N is an integer from 0 to 4;
e) compounds of the type of the acylsulfamoylbenzamides, for example of the formula (S-VII) below, which are known, for example, from WO 99/16744,

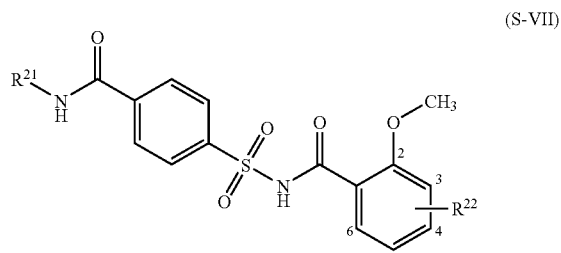

(S-VII)

for example those in which
$R^{21}$=cyclopropyl and $R^{22}$=H (S-3-1=4-cyclopropylaminocarbonyl-N-(2-methoxybenzoyl)benzenesulfonamide),
$R^{21}$=cyclopropyl and $R^{22}$=5-Cl (S-3-2),
$R^{21}$=ethyl and $R^{22}$=H (S-3-3),
$R^{21}$=isopropyl and $R^{22}$=5-Cl (S-3-4) and
$R^{21}$=isopropyl and $R^{22}$=H (S-3-5);
f) compounds of the type of the N-acylsulfamoylphenylureas of the formula (S-VIII), which are known, for example, from EP-A-365484

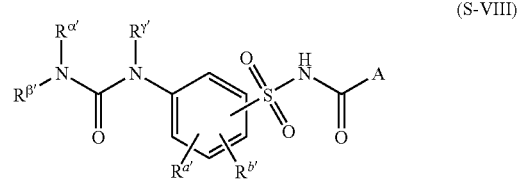

(S-VIII)

in which
A is a radical from the group consisting of

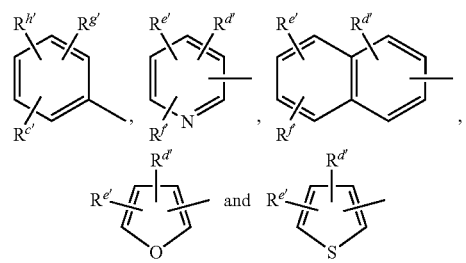

$R^{\alpha'}$ and $R^{\beta'}$ independently of one another are hydrogen or $(C_1-C_8)$-alkyl, $(C_3-C_8)$-cycloalkyl, $(C_3-C_6)$-alkenyl, $(C_3-C_6)$-alkynyl,

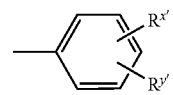

or $(C_1-C_4)$-,alkoxy or

[structure: phenyl ring with $R^{x'}$ and $R^{y'}$ substituents]

substituted by $C_1-C_4$-alkoxy or $R^{\alpha'}$ and $R^{\beta'}$ together are a $(C_4-C_6)$-alkylene bridge or a $(C_4-C_6)$-alkylene bridge which is interrupted by oxygen, sulfur, SO, SO$_2$, NH or —N(($C_1-C_4$)-alkyl)-, $R^{\gamma'}$ is hydrogen or $(C_1-C_4)$-alkyl, $R^{a'}$ and $R^{b'}$ independently of one another are hydrogen, halogen, cyano, nitro, trifluoromethyl, $(C_1-C_4)$-alkyl, $(C_1-C_4)$-alkoxy, $(C_1-C_4)$-alkylthio, $(C_1-C_4)$-alkylsulfinyl, $(C_1-C_4)$-alkylsulfonyl, —COOR$^j$, —CONR$^{k'}$R$^{m'}$, —COR$^{n'}$, —SO$_2$NR$^{k'}$R$^{m'}$ or —OSO$_2$—$(C_1-C_4)$-alkyl, or $R^{a'}$ and $R^{b'}$ together are a $(C_3-C_4)$-alkylene bridge which may be substituted by halogen or $(C_1-C_4)$-alkyl, or a $(C_3-C_4)$-alkenylene bridge which may be substituted by halogen or $(C_1-C_4)$-alkyl, or a $C_4$-alkadienylene bridge which may be substituted by halogen or $(C_1-C_4)$-alkyl, and $R^{g'}$ and $R^{h'}$ independently of one another are hydrogen, halogen, $(C_1-C_4)$-alkyl, trifluoromethyl, methoxy, methylthio or —COOR$^{j'}$, where $R^{c'}$ is hydrogen, halogen, $(C_1-C_4)$-alkyl or methoxy, $R^{d'}$ is hydrogen, halogen, nitro, $(C_1-C_4)$-alkyl, $(C_1-C_4)$-alkoxy, $(C_1-C_4)$-alkylthio, $(C_1-C_4)$-alkylsulfinyl, $(C_1-C_4)$-alkylsulfonyl, —COOR$^{j'}$ or —CONR$^{k'}$R$^{m'}$, $R^{e'}$ is hydrogen, halogen, $(C_1-C_4)$-alkyl, —COOR$^j$, trifluoromethyl or methoxy, or $R^d$ and $R^e$ together are a $(C_3-C_4)$-alkylene bridge, $R^{f'}$ is hydrogen, halogen or $(C_1-C_4)$-alkyl, $R^{X'}$ and $R^{Y'}$ independently of one another are hydrogen, halogen, $(C_1-C_4)$-alkyl, $(C_1-C_4)$-alkoxy, $(C_1-C_4)$-alkylthio, —COOR$^{j'}$, trifluoromethyl, nitro or cyano, $R^{j'}$, $R^{k'}$ and $R^{m'}$ independently of one another are hydrogen or $(C_1-C_4)$-alkyl, $R^{k'}$ and $R^{m'}$ together are a $C_4-C_6$-alkylene bridge or a $(C_4-C_6)$-alkylene bridge which is interrupted by oxygen, NH or —N(($C_1-C_4$)-alkyl)-, and $R^{n'}$ is $(C_1-C_4)$-alkyl, phenyl or phenyl which is substituted by halogen, $(C_1-C_4)$-alkyl, methoxy, nitro or trifluoromethyl, preferably 1-[4-(N-2-methoxybenzoylsulfamoyl)phenyl]-3-methylurea, 1-[4-(N-2-methoxybenzoylsulfamoyl)phenyl]-3,3-dimethylurea, 1-[4-(N-4,5-dimethylbenzoylsulfamoyl)phenyl]-3-methylurea, 1-[4-(N-naphthoylsulfamoyl)phenyl]-3,3-dimethylurea, g) compounds of the type of the acylsulfamoylbenzamides of the formula (S-IX), known from EP-A-1019368, if appropriate also in salt form, (S-IX)

[chemical structure of S-IX]

in which $R^{101}$ is methyl, methoxy or trifluoromethoxy;

$R^{102}$ is hydrogen, chlorine or methyl;

$R^{103}$ is hydrogen, ethyl or propargyl;

$R^{104}$ is ethyl, cyclopropyl, isopropyl or propargyl, or $R^{103}$ and $R^{104}$ together form the group $(CH_2)_4$, including the stereoisomers, and the salts customary in agriculture.

Preference is given to herbicide-safener combinations comprising (A) a herbicidally effective amount of one or more compounds of the formula (I) or salts thereof and (B) an amount, acting as an antidote, of one or more safeners.

Herbicidally effective amount in the sense of the invention is an amount of one or more herbicides sufficient to have an adverse impact on plant growth. In the sense of the invention, an amount which acts as an antidote is an amount of one or more safeners sufficient to reduce the phytotoxic action of crop protection agents (for example herbicides) in crop plants.

The compounds of the formula (S-II) are known, for example, from EP-A-0 333 131 (ZA-89/1960), EP-A-0 269 806 (U.S. Pat. No. 4,891,057), EP-A-0 346 620 (AU-A-89/34951), EP-A-0 174 562, EP-A-0 346 620 (WO-A-91/08 202), WO-A-91/07 874 or WO-A 95/07 897 (ZA 94/7120) and the literature cited therein or can be prepared by or analogously to the processes described therein. The compounds of the formula (S-III) are known from EP-A-0 086 750, EP-A-0 94349 (U.S. Pat. No. 4,902,340), EP-A-0 191736 (U.S. Pat. No. 4,881,966) and EP-A-0 492 366 and the literature cited therein or can be prepared by or analogously to the processes described therein. Furthermore, some compounds are described in EP-A-0 582 198 and WO 2002/34048.

The compounds of the formula (S-IV) are known from numerous patent applications, for example U.S. Pat. No. 4,021,224 and U.S. Pat. No. 4,021,229.

Compounds of the group B (b) are furthermore known from CN-A-87/102 789, EP-A-365484 and from "The Pesticide Manual", The British Crop Protection Council and the Royal Society of Chemistry, 11th edition, Farnham 1997.

The compounds of the group B (c) are described in WO-A-97/45016, those of group B (d) in WO-A-99/16744, those of group B (e) in EP-A-365484 and those of group B (g) in EP-A-1019368.

The publications cited contain detailed statements about preparation processes and starting materials and mention preferred compounds. These publications are expressly referred to; by reference, they form part of the present description.

Preference is given to herbicide-safener combinations comprising safeners of the formula (S-II) and/or (S-III) in which the symbols and indices are as defined below:

$R^{24}$ is hydrogen, $(C_1-C_{18})$-alkyl, $(C_3-C_{12})$-cycloalkyl, $(C_2-C_8)$-alkenyl and $(C_2-C_{18})$-alkynyl, where the carbon-containing groups may be substituted by one or more, preferably up to three, radicals $R^{50}$;

$R^{50}$ is identical or different and is halogen, hydroxyl, $(C_1-C_8)$-alkoxy, $(C_1-C_8)$-alkylthio, $(C_2-C_8)$-alkenylthio, $(C_2-C_8)$-alkynylthio, $(C_2-C_8)$-alkenyloxy, $(C_2-C_8)$-alkynyloxy, $(C_3-C_7)$-cycloalkyl, $(C_3-C_7)$-cycloalkoxy, cyano, mono- and di($C_1-C_4$)-alkylamino, carboxyl, $(C_1-C_8)$-alkoxycarbonyl, $(C_2-C_8)$-alkenyloxycarbonyl, $(C_1-C_8)$-alkylthiocarbonyl, $(C_2-C_8)$-alkynyloxycarbonyl, $(C_1-C_8)$-alkylcarbonyl, $(C_2-C_8)$-alkenylcarbonyl, $(C_2-C_8)$-alkynylcarbonyl, 1-(hydroxyimino)-$(C_1-C_6)$-alkyl, 1-[$(C_1-C_4)$-alkylimino]-$(C_1-C_4)$-alkyl, 1-[$(C_1-C_4)$-alkoxyimino]-$(C_1-C_6)$-alkyl, $(C_1-C_8)$-alkylcarbonylamino, $(C_2-C_8)$-alkenylcarbonylamino, $(C_2-C_8)$-alkynylcarbonylamino, aminocarbonyl, $(C_1-C_8)$-alkylaminocarbonyl, di-$(C_1-C_6)$-alkylaminocarbonyl, $(C_2-C_6)$-alkenylaminocarbonyl, $(C_2-C_6)$-alkynylaminocarbonyl, $(C_1-C_8)$-alkoxycarbonylamino, $(C_1-C_8)$-alkylaminocarbonylamino, $(C_1-C_6)$-alkylcarbonyloxy which is unsubstituted or substituted by $R^{51}$, $(C_2-C_6)$-alkenylcarbonyloxy, $(C_2-C_6)$-alkynylcarbonyloxy, $(C_1-C_8)$-alkylsulfonyl, phenyl, phenyl-$(C_1-C_6)$-alkoxy, phenyl-$(C_1-C_6)$-alkoxycarbonyl, phenoxy, phenoxy-$(C_1-C_6)$-alkoxy, phenoxy-$(C_1-C_6)$-alkoxycarbonyl, phenylcarbonyloxy, phenylcarbonylamino, phenyl-$(C_1-C_6)$-alkylcarbonylamino, where the phenyl ring of the 9 last-mentioned radicals is unsubstituted or mono- or polysubstituted, preferably up to trisubstituted, by radicals $R^{52}$; SiR'$_3$, —O—SiR'$_3$, R'$_3$Si—$(C_1-C_8)$-alkoxy, —CO—O—NR'$_2$, —O—N=CR'$_2$, —N=CR'$_2$, —O—NR'$_2$, —NR'$_2$, CH(OR')$_2$, —O—$(CH_2)_m$—CH(OR')$_2$, —CR'''(OR')$_2$, —O—$(CH_2)_m$CR'''(OR'')$_2$ or by R''O—CHR'''CHCOR''—$(C_1-C_6)$-alkoxy, $R^{51}$ is identical or different and is halogen, nitro, $(C_1-C_4)$-alkoxy and phenyl which is unsubstituted or substituted by one or more, preferably up to three, radicals $R^{52}$;

$R^{52}$ is identical or different and is halogen, $(C_1-C_4)$-alkyl, $(C_1-C_4)$-alkoxy, $(C_1-C_4)$-haloalkyl, $(C_1-C_4)$-haloalkoxy or nitro;

R' is identical or different and is hydrogen, $(C_1-C_4)$-alkyl, phenyl which is unsubstituted or substituted by one or more, preferably up to three, radicals $R^{52}$, or two radicals R' together form a $(C_2-C_6)$-alkanediyl chain;

R" is identical or different and is $(C_1-C_4)$-alkyl, or two radicals R" together form a $(C_2-C_6)$-alkanediyl chain;

R''' is hydrogen or $(C_1-C_4)$-alkyl;

m is 0, 1, 2, 3, 4, 5 or 6.

Particular preference is given to herbicide-safener combinations according to the invention comprising safeners of the formula (S-II) and/or (S-III) in which the symbols and indices are as defined below:

$R^{24}$ is hydrogen, $(C_1-C_8)$-alkyl or $(C_3-C_7)$-cycloalkyl, where the carbon-containing radicals above are unsubstituted or mono- or polysubstituted by halogen or mono- or disubstituted, preferably monosubstituted, by radicals $R^{50}$, $R^{50}$ are identical or different and are hydroxyl, $(C_1-C_4)$-alkoxy, carboxyl, $(C_1-C_4)$-alkoxycarbonyl, $(C_2-C_6)$-alkenyloxycarbonyl, $(C_2-C_6)$-alkynyloxycarbonyl, 1-(hydroxyimino)-$(C_1-C_4)$-alkyl, 1-[$(C_1-C_4)$-alkylimino]-$(C_1-C_4)$-alkyl and 1-[$(C_1-C_4)$-alkoxyimino]-$(C_1-C_4)$-alkyl; —SiR'$_3$, —O—N=CR'$_2$, —N=CR'$_2$, —NR'$_2$ and —O—NR'$_2$, in which R' is identical or different and is hydrogen, $(C_1-C_4)$-alkyl or, as a pair, is a $(C_4-C_5)$-alkanediyl chain, $R^{27}$, $R^{28}$, $R^{29}$ are identical or different and are hydrogen, $(C_1-C_8)$-alkyl, $(C_1-C_6)$-haloalkyl, $(C_3-C_7)$-cycloalkyl or phenyl which is unsubstituted or substituted by one or more radicals from the group consisting of halogen, cyano, nitro, amino, mono- and di-[$(C_1-C_4)$-alkyl]amino, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio and $(C_1-C_4)$-alkylsulfonyl;

$R^{x'}$ is hydrogen or COOR$^{24}$, where $R^{26}$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_7)$-cycloalkyl or tri-$(C_1-C_4)$-alkylsilyl, $R^{17}$, $R^{19}$ are identical or different and are halogen, methyl, ethyl, methoxy, ethoxy, $(C_1-C_2)$-haloalkyl, preferably hydrogen, halogen or $(C_1-C_2)$-haloalkyl.

Very particular preference is given to safeners in which the symbols and indices in the formula (S-II) are as defined below:

$R^{17}$ is halogen, nitro or $(C_1-C_4)$-haloalkyl;

n' is 0, 1, 2 or 3;

$R^{18}$ is a radical of the formula OR$^{24}$, $R^{24}$ is hydrogen, $(C_1-C_8)$-alkyl or $(C_3-C_7)$-cycloalkyl, where the carbon-containing radicals above are unsubstituted or mono- or polysubstituted, preferably up to trisubstituted, by identical or different halogen radicals or up to disubstituted, preferably monosubstituted, by identical or different radicals from the group consisting of hydroxyl, $(C_1-C_4)$-alkoxy, $(C_1-C_4)$-alkoxycarbonyl, $(C_2-C_6)$-alkenyloxycarbonyl, $(C_2-C_6)$-alkynyloxycarbonyl, 1-(hydroxyimino)-$(C_1-C_4)$-alkyl, 1-[$(C_1-C_4)$-alkylimino]-$(C_1-C_4)$-alkyl, 1-[$(C_1-C_4)$-alkoxyimino]-$(C_1-C_4)$-alkyl and radicals of the formulae —SiR'$_3$, —O—N=R'$_2$, —N=CR'$_2$, —R'$_2$ and —O—NR'$_2$, where the radicals R' in the formulae mentioned are identical or different and are hydrogen, $(C_1-C_4)$-alkyl or, as a pair, are $(C_4-C_5)$-alkanediyl;

$R^{27}$, $R^{28}$, $R^{29}$ are identical or different and are hydrogen, $(C_1-C_8)$-alkyl, $(C_1-C_6)$-haloalkyl, $(C_3-C_7)$-cycloalkyl or phenyl which is unsubstituted or substituted by one or more radicals from the group consisting of halogen, $(C_1-C_4)$-alkyl, $(C_1-C_4)$-alkoxy, nitro, $(C_1-C_4)$-haloalkyl and $(C_1-C_4)$-haloalkoxy, and $R^{x'}$ is hydrogen or COOR$^{26}$, where $R^{26}$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_7)$-cycloalkyl or tri-$(C_1-C_4)$-alkylsilyl.

Very particular preference is also given to safeners of the formula (S-III) in which the symbols and indices are as defined below:

$R^{19}$ is halogen or $(C_1-C4)$-haloalkyl;

n' is 0, 1, 2 or 3, where $(R^{19})_{n'}$ is preferably 5-Cl;

$R^{20}$ is a radical of the formula OR$^{24}$;

T is CH$_2$ or CH(COO—$((C_1-C_3)$-alkyl)) and $R^{24}$ is hydrogen, $(C_1-C_8)$-alkyl, $(C_1-C_8)$-haloalkyl or $(C_1-C_4)$-alkoxy-$(C_1-C_4)$-alkyl, preferably hydrogen or $(C_1-C_8)$-alkyl.

Especially preferred are safeners of the formula (II) in which the symbols and indices are as defined below:

W is (W1);

$R^{17}$ is halogen or $(C_1-C2)$-haloalkyl;

n' is 0, 1, 2 or 3, where $(R^{17})_{n'}$ is preferably 2,4-Cl$_2$;

$R^{18}$ is a radical of the formula OR$^{24}$;

$R^{24}$ is hydrogen, $(C_1-C_8)$-alkyl, $(C_1-C_4)$-haloalkyl, $(C_1-C_4)$-hydroxyalkyl, $(C_3-C_7)$-cycloalkyl, $(C_1-C_4)$-alkoxy-$(C_1-C_4)$-alkyl or tri-$(C_1-C_2)$-alkylsilyl, preferably $(C_1-C_4)$-alkyl;

$R^{27}$ is hydrogen, $(C_1-C_8)$-alkyl, $(C_1-C_4)$-haloalkyl or $(C_3-C_7)$-cycloalkyl, preferably hydrogen or $(C_1-C_4)$-alkyl, and $R^{x'}$ is COOR$^{26}$, where $R^{26}$ is hydrogen, $(C_1-C_8)$-alkyl, $(C_1-C_4)$-haloalkyl, $(C_1-C_4)$-hydroxyalkyl, $(C_3-C_7)$-cycloalkyl, $(C_1-C_4)$-alkoxy-$(C_1-C_4)$-alkyl or tri-$(C_1-C_2)$-alkylsilyl, preferably hydrogen or $(C_1-C_4)$-alkyl.

Also especially preferred are herbicidal compositions comprising a safener of the formula (S-II) in which the symbols and indices are as defined below:

W is (W2);

$R^{17}$ is halogen or $(C_1-C2)$-haloalkyl;

n' is 0, 1, 2 or 3, where $(R^{17})_{n'}$ is preferably 2,4-Cl$_2$;

$R^{18}$ is a radical of the formula OR$^{24}$;

$R^{24}$ is hydrogen, $(C_1-C_8)$-alkyl, $(C_1-C_4)$-haloalkyl, $(C_1-C_4)$-hydroxyalkyl, $(C_3-C_7)$-cycloalkyl, $((C_1-C_4)$-alkoxy)-$(C_1-C_4)$-alkyl or tri-$(C_1-C_2)$-alkylsilyl, preferably $(C_1-C_4)$-alkyl; and $R^{27}$ is hydrogen, $(C_1-C_8)$-alkyl, $(C_1-C_4)$-haloalkyl, $(C_3-C_7)$-cycloalkyl or unsubstituted or substituted phenyl, preferably hydrogen, $(C_1-C_4)$-alkyl or phenyl which is unsubstituted or substituted by one or more radicals from the group consisting of halogen, $(C_1-C_4)$-alkyl, $(C_1-C_4)$-haloalkyl, nitro, cyano and $(C_1-C_4)$-alkoxy.

Especially preferred are also safeners of the formula (II) in which the symbols and indices are as defined below:

W is (W3);
$R^{17}$ is halogen or $(C_1-C_2)$-haloalkyl;
n' is 0, 1, 2 or 3, where $(R^{17})_{n'}$ is preferably 2,4-$Cl_2$;
$R^{18}$ is a radical of the formula $OR^{24}$;
$R^{24}$ is hydrogen, $(C_1-C_8)$-alkyl, $(C_1-C_4)$-haloalkyl, $(C_1-C_4)$-hydroxyalkyl, $(C_3-C_7)$-cycloalkyl, $(C_1-C_4)$-alkoxy-$(C_1-C_4)$-alkyl or tri-$(C_1-C_2)$-alkylsilyl, preferably $(C_1-C_4)$-alkyl, and
$R^{28}$ is $(C_1-C_8)$-alkyl or $(C_1-C_4)$-haloalkyl, preferably $C_1$-haloalkyl.

Especially preferred are also safeners of the formula (S-II) in which the symbols and indices are as defined below:

W is (W4);
$R^{17}$ is halogen, nitro, $(C_1-C_4)$-alkyl, $(C_1-C_2)$-haloalkyl, preferably $CF_3$, or $(C_1-C_4)$-alkoxy;
n' is 0, 1, 2 or 3;
m' is 0 or 1;
$R^{18}$ is a radical of the formula $OR^{24}$;
$R^{24}$ is hydrogen, $(C_1-C_4)$-alkyl, carboxy-$(C_1-C_4)$-alkyl, $(C_1-C_4)$-alkoxycarbonyl-$(C_1-C_4)$-alkyl, preferably $(C_1-C_4)$-alkoxy-CO—$CH_2$, $(C_1-C_4)$-alkoxy-CO—C($CH_3$)H—, HO—CO—$CH_2$— or HO—CO—C($CH_3$)H, and
$R^{29}$ is hydrogen, $(C_1-C_4)$-alkyl, $(C_1-C_4)$-haloalkyl, $(C_3-C_7)$-cycloalkyl or phenyl which is unsubstituted or substituted by one or more radicals from the group consisting of halogen, $(C_1-C_4)$-alkyl, $(C_1-C_4)$-haloalkyl, nitro, cyano and $(C_1-C_4)$-alkoxy.

Particularly suitable safeners for the herbicidally active compounds of the formula (I) are the following groups of compounds:

a) compounds of the type of the dichlorophenylpyrazoline-3-carboxylic acid (i.e. of the formula (S-II) in which W=(W1) and $(R^{17})_n$=2,4-$Cl_2$), preferably compounds such as ethyl 1-(2,4-dichlorophenyl)-5-(ethoxycarbonyl)-5-methyl-2-pyrazoline-3-carboxylate (S-II-1, mefenpyr-diethyl), mefenpyr-di methyl and mefenpyr (S-II-0), and related compounds as described in WO-A 91/07874;

b) derivatives of dichlorophenylpyrazolecarboxylic acid (i.e. of the formula (S-II) in which W=(W2) and $(R^{17})_n$=2,4-$Cl_2$), preferably compounds such as ethyl 1-(2,4-dichlorophenyl)-5-methylpyrazole-3-carboxylate (S-II-2), ethyl 1-(2,4-dichlorophenyl)-5-isopropylpyrazole-3-carboxylate (S-II-3), ethyl 1-(2,4-dichlorophenyl)-5-(1,1-dimethylethyl)pyrazole-3-carboxylate (S-II-4), ethyl 1-(2,4-dichlorophenyl)-5-phenylpyrazole-3-carboxylate (S-II-5) and related compounds, as described in EP-A-0 333 131 and EP-A-0 269 806;

c) compounds of the type of the triazolecarboxylic acids (i.e. of the formula (S-II) in which W=(W3) and $(R^{17})_n$=2,4-$Cl_2$), preferably compounds such as fenchlorazole-ethyl, i.e. ethyl 1-(2,4-dichlorophenyl)-5-trichloromethyl-(1H)-1,2,4-triazole-3-carboxylate (S-II-6), and related compounds (see EP-A-0 174 562 and EP-A-0 346 620);

d) compounds of the type of the 5-benzyl- or 5-phenyl-2-isoxazoline-3-carboxylic acid or of the 5,5-diphenyl-2-isoxazoline-3-carboxylic acid, such as isoxadifen (S-II-12), (in which W=(W4)), preferably compounds such as ethyl 5-(2,4-dichlorobenzyl)-2-isoxazoline-3-carboxylate (S-II-7) or ethyl 5-phenyl-2-isoxazoline-3-carboxylate (S-II-8) and related compounds, as described in WO-A-91/08202, or of ethyl 5,5-diphenyl-2-isoxazolinecarboxylate (S-II-9, isoxadifen-ethyl) or n-propyl 5,5-diphenyl-2-isoxazolinecarboxylate (S-II-10) or of ethyl 5-(4-fluorophenyl)-5-phenyl-2-isoxazoline-3-carboxylate (S-II-11), as described in WO-A-95/07897.

e) Compounds of the type of the 8-quinolineoxyacetic acid, for example those of the formula (S-III) in which $(R^{19})_n$=5-Cl, $R^{20}$=$OR^{24}$ and T=$CH_2$, preferably the compounds
1-methylhexyl (5-chloro-8-quinolineoxy)acetate (S-III-1, cloquintocet-mexyl),
1,3-dimethylbut-1-yl (5-chloro-8-quinolineoxy)acetate (S-III-2),
4-allyloxybutyl (5-chloro-8-quinolineoxy)acetate (S-III-3),
1-allyloxyprop-2-yl (5-chloro-8-quinolineoxy)acetate (S-III-4),
ethyl (5-chloro-8-quinolineoxy)acetate (S-III-5),
methyl (5-chloro-8-quinolineoxy)acetate (S-III-6),
allyl (5-chloro-8-quinolineoxy)acetate (S-III-7),
2-(2-propylideneiminoxy)-1-ethyl (5-chloro-8-quinolineoxy)acetate (S-III-8),
2-oxoprop-1-yl (5-chloro-8-quinolineoxy)acetate (S-III-9),
(5-chloro-8-quinolineoxy)acetic acid (S-III-10) and its salts, as described, for example, in WO-A-2002/34048, and related compounds as described in EP-A-0 860 750, EP-A-0 094 349 and EP-A-0 191 736 or EP-A-0 492 366.

f) Compounds of the type of the (5-chloro-8-quinolineoxy) malonic acid, i.e. of the formula (S-III) in which $(R^{19})_n$=5-Cl, $R^{20}$=$OR^{24}$, T=—CH(COO-alkyl)-, preferably the compounds diethyl (5-chloro-8-quinolineoxy)malonate (S-III-11), diallyl (5-chloro-8-quinolineoxy)-malonate, methyl ethyl (5-chloro-8-quinolineoxy)malonate and related compounds, as described in EP-A-0 582 198.

g) Compounds of the type of the dichloroacetamide, i.e. of the formula (S-IV), preferably:
N,N-diallyl-2,2-dichloroacetamide (dichlormid (S-IV-1), from U.S. Pat. No. 4,137,070),
4-dichloroacetyl-3,4-dihydro-3-methyl-2H-1,4-benzoxazine (IV-2, benoxacor, from EP 0 149 974),
N1,N2-diallyl-N2-dichloroacetylglycinamide (DKA-24 (IV-3), from HU 2143821),
4-dichloroacetyl-1-oxa-4-azaspiro[4,5]decane (AD-67),
2,2-dichloro-N-(1,3-dioxolan-2-ylmethyl)-N-(2-propenyl)acetamide (PPG-1292),
3-dichloroacetyl-2,2,5-trimethyloxazolidine (R-29148, S-IV-4),
3-dichloroacetyl-2,2-dimethyl-5-phenyloxazolidine,
3-dichloroacetyl-2,2-dimethyl-5-(2-thienyl)oxazolidine,
3-dichloroacetyl-5-(2-furanyl)-2,2-dimethyloxazolidine (furilazole (S-IV-5), MON 13900),
1-dichloroacetylhexahydro-3,3,8a-trimethylpyrrolo[1,2-a]pyrimidin-6(2H)-one (dicyclonon, BAS 145138).

h) Compounds of the group B(b), preferably
1,8-naphthalic anhydride (S-b-1),
methyl diphenylmethoxyacetate (S-b-2),
cyanomethoxyimino(phenyl)acetonitrile (cyometrinil) (S-b-3),
1-(2-chlorobenzyl)-3-(1-methyl-1-phenylethyl)urea (cumyluron) (S-b-4),
O,O-diethyl S-2-ethylthioethyl phosphorodithioate (disulfoton) (S-b-5),
4-chlorophenyl methylcarbamate (mephenate) (S-b-6),
O,O-diethyl O-phenyl phosphorothioate (dietholate) (S-b-7),
4-carboxy-3,4-dihydro-2H-1-benzopyran-4-acetic acid (CL-304415, CAS-Regno: 31541-57-8) (S-b-8),
1,3-dioxolan-2-ylmethoxyimino(phenyl)acetonitrile (oxabetrinil) (S-b-9), 4'-chloro-2,2,2-trifluoroacetophenone O-1,3-dioxolan-2-ylmethyloxime (fluxofenim) (S-b-10),
4,6-dichloro-2-phenylpyrimidine (fenclorim) (S-b-11),
benzyl 2-chloro-4-trifluoromethyl-1,3-thiazole-5-carboxylate (flurazole) (S-b-12),
2-dichloromethyl-2-methyl-1,3-dioxolane (MG-191) (S-b-13),
N-(4-methylphenyl)-N'-(1-methyl-1-phenylethyl)urea (dymron) (S-b-14),
(2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichlor) and their salts and esters, preferably their $(C_1-C_8)$-esters.

Preferred safeners are furthermore compounds of the formula (S-V) or salts thereof in which $R^{30}$ is hydrogen, $(C_1-C_6)$-alkyl, $(C_3-C_6)$-cycloalkyl, furanyl or thienyl, where each of the 4 last-mentioned radicals is unsubstituted or substituted by one or more substituents from the group consisting of halogen, $(C_1-C_4)$-alkoxy, halo-$(C_1-C_6)$-alkoxy and $(C_1-C_4)$-alkylthio and, in the case of cyclic radicals, also $(C_1-C_4)$-alkyl and $(C_1-C_4)$-haloalkyl, $R^{31}$ is hydrogen, $R^{32}$ is halogen, halo-$(C_1-C_4)$-alkyl, halo-$(C_1-C_4)$-alkoxy, $(C_1-C_4)$-alkyl, $(C_1-C_4)$-alkoxy, $(C_1-C_4)$-alkylsulfonyl, $(C_1-C_4)$-alkoxycarbonyl or $(C_1-C_4)$-alkylcarbonyl, preferably halogen, $(C_1-C_4)$-haloalkyl, such as trifluoromethyl, $(C_1-C_4)$-alkoxy, halo-$(C_1-C_4)$-alkoxy, $(C_1-C_4)$-alkoxycarbonyl or $(C_1-C_4)$-alkylsulfonyl, $R^{33}$ is hydrogen, $R^{34}$ is halogen, $(C_1-C_4)$-alkyl, halo-$(C_1-C_4)$-alkyl, halo-$(C_1-C_4)$-alkoxy, $(C_3-C_6)$-cycloalkyl, phenyl, $(C_1-C_4)$-alkoxy, cyano, $(C_1-C_4)$-alkylthio, $(C_1-C_4)$-alkylsulfinyl, $(C_1-C_4)$-alkylsulfonyl, $(C_1-C_4)$-alkoxycarbonyl or $(C_1-C_4)$-alkylcarbonyl, preferably halogen, $(C_1-C_4)$-alkyl, $(C_1-C_4)$-haloalkyl, such as trifluoromethyl, halo-$(C_1-C_4)$-alkoxy, $(C_1-C_4)$-alkoxy or $(C_1-C_4)$-alkylthio, n is 0, 1 or 2 and
m is 1 or 2.

Particular preference is given to compounds of the formula (S-V) in which $R^{30}$=$H_3C$—O—$CH_2$—, $R^{31}$=$R^{33}$=H, $R^{34}$=2-OMe (S-V-1), $R^{30}$=$H_3C$—O—$CH_2$—, $R^{31}$=$R^{33}$=H, $R^{34}$=2-OMe-5-Cl (S-V-2), $R^{30}$=cyclopropyl, $R^{31}$=$R^{33}$=H, $R^{34}$=2-OMe (S-V-3),
$R^{30}$=cyclopropyl, $R^{31}$=$R^{33}$=H, $R^{34}$=2-OMe-5-Cl (S-V-4),
$R^{30}$=cyclopropyl, $R^{31}$=$R^{33}$=H, $R^{34}$=2-Me (S-V-5),
$R^{30}$=tert-butyl, $R^{31}$=$R^{33}$'H, $R^{34}$=2-OMe (S-V-6).

Preference is furthermore given to safeners of the formula (S-VI) in which
$X^3$ is CH;
$R^{35}$ is hydrogen, $(C_1-C_6)$-alkyl, $(C_3-C_6)$-cycloalkyl, $(C_2-C_6)$-alkenyl, $(C_5-C_6)$-cycloalkenyl, phenyl or 3- to 6-membered heterocyclyl having up to 3 heteroatoms from the group consisting of nitrogen, oxygen and sulfur, where the six last-mentioned radicals are optionally substituted by one or more identical or different substituents from the group consisting of halogen, $(C_1-C_6)$-alkoxy, $(C_1-C_6)$-haloalkoxy, $(C_1-C_2)$-alkylsulfinyl, $(C_1-C_2)$-alkylsulfonyl, $(C_3-C_6)$-cycloalkyl, $(C_1-C_4)$-alkoxycarbonyl, $(C_1-C_4)$-alkylcarbonyl and phenyl and, in the case of cyclic radicals, also $(C_1-C_4)$-alkyl and $(C_1-C_4)$-haloalkyl;

$R^{36}$ is hydrogen, $(C_1-C_6)$-alkyl, $(C_2-C_6)$-alkenyl, $(C_2-C_6)$-alkynyl, where the three last-mentioned radicals are optionally substituted by one or more identical or different substituents from the group consisting of halogen, hydroxy, $(C_1-C_4)$-alkyl, $(C_1-C_4)$-alkoxy and $(C_1-C_4)$-alkylthio;

$R^{37}$ is halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulfonyl, $(C_1-C_4)$-alkoxycarbonyl or $(C_1-C_4)$-alkylcarbonyl;

$R^{38}$ is hydrogen;

$R^{39}$ is halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulfinyl, $(C_1-C_4)$-alkylsulfonyl, $(C_1-C_4)$-alkoxycarbonyl or $(C_1-C_4)$-alkylcarbonyl;

n is 0, 1 or 2 and
m is 1 or 2.

Preferred safeners of the formula (S-VII) are (S-3-1), (S-3-2), (S-3-3), (S-3-4) and (S-3-5).

Preferred safeners of the formula (VIII) are

1-[4-(N-2-methoxybenzoylsulfamoyl)phenyl]-3-methylurea (S-VIII-1),

1-[4-(N-2-methoxybenzoylsulfamoyl)phenyl]-3,3-dimethylurea (S-VIII-2),

1-[4-(N-4,5-dimethylbenzoylsulfamoyl)phenyl]-3-methylurea (S-VIII-3) and

1-[4-(N-naphthoylsulfamoyl)phenyl]-3,3-dimethylurea (S-VIII-4),

Preferred safeners of the formula S-IX are compounds of the formulae S-IX-A1 to S-IX-A4,

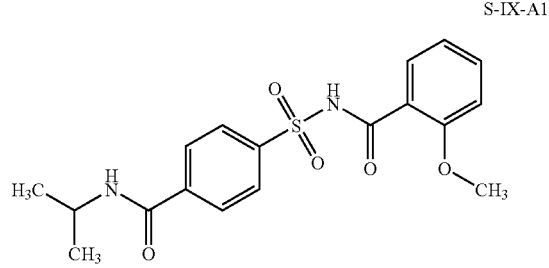

S-IX-A1

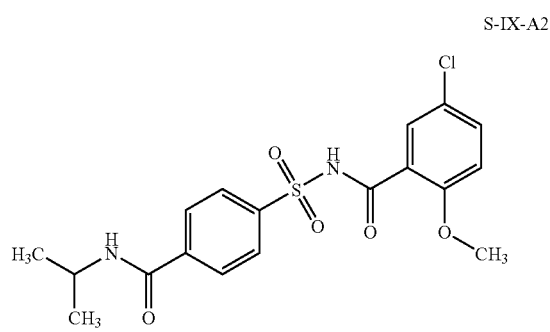

S-IX-A2

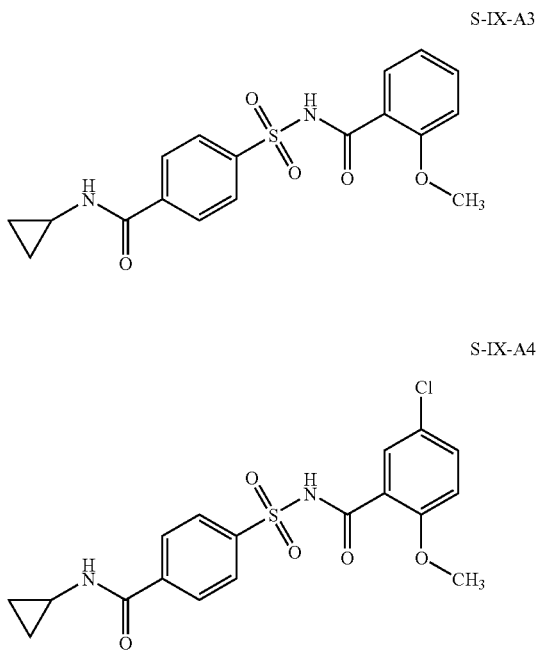

S-IX-A3

S-IX-A4 from among which the compound S-IX-A3 is very particularly preferred as safener.

Particularly preferred combinations of herbicidally active compounds of the formula (I) as listed in any of Tables 1 to 4 and safeners (B) are those in which the safener (B) is selected from the group of safeners consisting of the compounds of the formulae S-II-1 (mefenpyr-diethyl), S-II-9 (isoxadifen-ethyl), S-III-1 (chloquintocet-mexyl), S-b-11 (fenclorim), S-b-14 (dymron), S-IX-A3 (4-cyclopropylaminocarbonyl-N-(2-methoxybenzoyl)benzenesulfonamide, N-({4-[(cyclopropylamino)carbonyl]phenyl}-sulfonyl)-2-methoxybenzamide, very particularly preferred as safeners (B) are the compounds S-II-1 and S-IX-A3).

Particularly preferred for use in rice is isoxadifen-ethyl. Particularly preferred for use in cereals are mefenpyr-diethyl, cloquintocet-mexyl and 4-cyclopropylaminocarbonyl-N-(2-methoxybenzoyl)benzenesulfonamide [N-({4-[(cyclopropylamino)carbonyl]phenyl}sulfonyl)-2-methoxybenzamide], in corn in particular isoxadifen-ethyl and 4-cyclopropylaminocarbonyl-N-(2-methoxybenzoyl)-benzenesulfonamide [N-({4-[(cyclopropylamino)carbonyl]phenyl}sulfonyl)-2-methoxy-benzamide]. For use in sugar cane, preference is given to isoxadifen-ethyl. A mixture with other known active compounds, such as fungicides, insecticides, acaricides, nematicides, bird repellents, plant nutrients and agents which improve soil structure, is also possible.

Some of the safeners are already known as herbicides and accordingly, in addition to the herbicidal action against harmful plants, also act by protecting the crop plants.

The weight ratios of herbicide (mixture) to safener generally depend on the herbicide application rate and the effectiveness of the safener in question and may vary within wide limits, for example in the range from 200:1 to 1:200, preferably from 100:1 to 1:100, in particular from 20:1 to 1:20. The safeners may be formulated analogously to the compounds of the formula (I) or their mixtures with other herbicides/pesticides and be provided and used as a finished formulation or as a tank mix with the herbicides.

For application, the formulations present in commercial form are, if appropriate, diluted in a customary manner, for example in the case of wettable powders, emulsifiable concentrates, dispersions and water-dispersable granules with water. Preparations in the form of dusts, granules for soil application or granules for broadcasting and sprayable solutions are usually not diluted with other inert substances prior to application.

The required application rate of the compounds of the formula (I) varies according to the external conditions such as, inter alia, temperature, humidity and the type of herbicide used. It may vary within wide limits, for example between 0.001 and 10.0 kg/ha or more of active substance; however, preferably it is between 0.005 and 5 kg/ha.

The present invention is illustrated in more detail by the examples below; however, these examples do not limit the invention in any way.

A. SYNTHESIS EXAMPLES

Some examples of syntheses of compounds of the formula (I) or salts thereof are described in an examplary manner below.

3-[(S)-{([5-(Difluoromethoxy)-1-methyl-3-(trifluoromethyl)-1H-pyrazol-4-yl]methyl}sulfinyl]-5,5-dimethyl-4,5-dihydroisoxazole (Ex. 483) and 3-[(R)-{([5-(difluoromethoxy)-1-methyl-3-(trifluoromethyl)-1H-pyrazol-4-yl]methyl}sulfinyl]-5,5-dimethyl-4,5-dihydroisoxazole (Ex. 664)

3-({[5-(Difluoromethoxy)-1-methyl-3-(trifluoromethyl)-1H-pyrazol-4-yl]methyl}thio)-5,5-dimethyl-4,5-dihydroisoxazole (3.5 g, 9.741 mmol), which can be obtained according to EP 1 541 561 A, WO 2005/105755 A, WO 2004/014138 A or WO 2007/003295 A, is initially charged in 80 ml of toluene. With stirring, 3-chloroperbenzoic acid (1.856 g, 8.28 mmol, 77% pure) is then added a little at a time, and the mixture is stirred at room temperature for a further 4 hours. For work-up, the reaction mixture is washed successively with water, aqueous $NaHSO_3$ solution, aqueous $NaHCO_3$ solution and finally with NaCl solution. The organic phase is dried over magnesium sulfate, filtered off and concentrated. The residue is triturated with n-heptane, filtered off and dried. The racemic 3-({[5-(difluoromethoxy)-1-methyl-3-(trifluoromethyl)-1H-pyrazol-4-yl]methyl}sulfinyl)-5,5-dimethyl-4,5-dihydroisoxazole obtained (3.0 g, 99% pure) is separated into the enantiomers by preparative chiral HPLC (column: Chiralcel® OD; mobile phase: n-hexane/2-propanol 90:10; flow rate: 0.6 ml/min; column temperature: 25° C.). This gives 1.524 g (41.7% of theory) of 3-[(S)-{([5-(difluoromethoxy)-1-methyl-3-(trifluoromethyl)-1H-pyrazol-4-yl]methyl}sulfinyl]-5,5-dimethyl-4,5-dihydroisoxazole ($R_t$=11.124 min) and 1.410 g (38.6% of theory) of 3-[(R)-{([5-(difluoromethoxy)-1-methyl-3-(trifluoromethyl)-1H-pyrazol-4-yl]methyl}sulfinyl]-5,5-dimethyl-4,5-dihydroisoxazole ($R_t$=14.244 min).

The absolute configuration of 3-[(R)-{([5-(difluoromethoxy)-1-methyl-3-(trifluoromethyl)-1H-pyrazol-4-yl]methyl}sulfinyl]-5,5-dimethyl-4,5-dihydroisoxazole was confirmed by X-ray analysis.

3-[(S)-(2,6-Difluorobenzyl)sulfinyl]-5,5-dimethyl-4,5-dihydroisoxazole (Ex. 6) and 3-[(R)-(2,6-difluorobenzyl)sulfinyl]-5,5-dimethyl-4,5-dihydroisoxazole (Ex. 228)

Commercially available (−)-2,2'-dihydroxy-1,1'-binaphthyl [(S)-binol], 0.056 g, 0.2 mmol] is initially charged in chlororform (5 ml). The catalyst titanium(IV) isopropoxide (0.03 ml, 0.1 mmol) is then added dropwise, followed by water (0.070 g, 3.9 mmol). The mixture is stirred at room temperature for 15 minutes. 3-[(2,6-Difluorobenzyl)sulfanyl]-5,5-dimethyl-4,5-dihydroisoxazole (0.5 g, 1.9 mmol), which can be obtained according to WO 2001/01 261 3 A, WO 2006/024820 A or WO 2006/037945 A, is then added, followed by the dropwise addition of cumene hydroperoxide (0.43 ml, 80%, 2.2 mmol). The reaction is stirred at room temperature for 6 hours and then allowed to stand overnight. For work-up, the reaction mixture is diluted with chloroform and washed successively with water, twice with 5% strength $Na_2S_2O_5$ solution and finally with NaCl solution. The organic phase is dried over magnesium sulfate, filtered off and concentrated. The residue is chromatographed on silica gel (heptane/ethyl acetate 10:0 to 7:3). This gives 100 mg (19% of theory) of 3-[(2,6-difluorobenzyl)sulfinyl]-5,5-dimethyl-4,5-dihydroisoxazole with an ee (R) of 12%. The enantiomer mixture obtained is then separated into the enantiomers by preparative chiral HPLC. This gives 0.03 g (6% of theory) of 3-[(S)-(2,6-difluorobenzyl)sulfinyl]-5,5-dimethyl-4,5-dihydroisoxazole ($R_t$=18.293 min) and 0.03 g (6% of theory) of 3-[(R)-(2,6-difluorobenzyl)sulfinyl]-5,5-dimethyl-4,5-dihydroisoxazole ($R_t$=35.353 min).

3-[(S)-(2,6-Dichlorobenzyl)sulfinyl]-5,5-dimethyl-4,5-dihydroisoxazole (Ex. 32) and 3-[(R)-(2,6-dichlorobenzyl)sulfinyl]-5,5-dimethyl-4,5-dihydroisoxazole (Ex. 254)

a) Preparation of 2,6-dichlorobenzyl imidothiocarbamate hydrochloride 2,6-Dichlorobenzyl chloride (19.0 g, 97 mmol) is initially charged in 200 ml of ethanol. Thiourea is added, and the mixture is stirred at reflux for 8 hours. The reaction is concentrated and the solid is triturated with tetrahydrofuran, filtered off with suction and dried. This gives 26.12 g of product (94% of theory). The salt is reacted further without any further reaction steps.

b) Preparation of 3-(2,6-dichlorobenzyl)sulfanyl-5,5-dimethyl-4,5-dihydroisoxazole 2,6-Dichlorobenzyl imidothiocarbamate hydrochloride (1.533 g, 6 mmol) is added to a vigorously stirred mixture consisting of 50 ml of toluene and 50% strength aqueous sodium hydroxide solution (21 g), and the mixture is stirred vigorously for a further 1.5 hours. Tetra-n-butylammonium bromide (0.509 g, 2 mmol) and 5,5-dimethyl-3-(methyl-sulfonyl)-4,5-dihydroisoxazole (1.0 g, 6 mmol) are then added, and the mixture is stirred vigorously at 25° C. for a further 4 hours. For work-up, the reaction solution is added to water and extracted with toluene. The combined organic phases are dried and concentrated. This gives 1.50 g of product (87% of theory). NMR ($CDCl_3$, 400 MHz): 1.44 (s, 6H, $CH_3$); 2.83 (s, 2H, $CH_2$); 4.63 (s, 2H, $SCH_2$); 7.18 (m, 1H, Ar); 7.31 (d, 2H, Ar).

c) Asymmetric Sulfoxidation

The catalyst tungsten(VI) oxide ($WO_3$; 0.018 g, 0.07 mmol), the ligand $(DHQ)_2Pyr$ (0.134 g, 0.15 mmol) and 3-[(2,6-dichlorobenzyl)sulfanyl]-5,5-dimethyl-4,5-dihydroisoxazole (0.440 g, 1.5 mmol) are initially charged in THF (5 ml). Hydrogen peroxide ($H_2O_2$ 30%, 0.17 ml, 1.65 mmol) is added dropwise with ice-bath cooling. The mixture is stirred at the same temperature for a further 8 hours and allowed to stand in the fridge (−5° C.) over the weekend. For work-up, the reaction mixture is filtered, added to water and extracted with ethyl acetate. The organic phase is dried over magnesium sulfate, filtered off and concentrated. The crude product contains 3-[(2,6-dichlorobenzyl)sulfinyl]-5,5-dimethyl-4,5-dihydroisoxazole with an ee (S) of 41% and the corresponding sulfone (0.2 g) and is directly separated into the enantiomeric sulfoxides by preparative chiral HPLC. This gives 0.02 g (4% of theory) of 3-[(S)-(2,6-dichlorobenzyl)sulfinyl]-5,5-dimethyl-4,5-dihydroisoxazole ($R_t$=19.746 min) and 0.03 g (6% of theory) of 3-[(R)-(2,6-dichlorobenzyl)sulfinyl]-5,5-dimethyl-4,5-dihydroisoxazole ($R_t$=32.760 min).

Retention times ($R_t$, in Minuten) and enantiomeric excess (ee) of chiral compounds were determined by analytic chiral HPLC [Chiralcel® OD column (250×4.6 mm, particle size 5 µm), temperature 25° C., flow rate 0.6 ml/min, hexane/2-propanol 90:10 v/v].

The racemates or enantiomeric mixtures were separated into the respective enantiomers by preparative chiral HPLC [Chiralcel® OD column (250×5 mm, particle size 10 µm), temperature 25° C., flow rate 0.6 ml/min, hexane/2-propanol 90:10 v/v].

The compounds described in Tables 1-4 below are obtained according to or analogously to the synthesis examples described above.

In the tables:
Me=methyl
Et=ethyl
Ph=phenyl
Pr=n-propyl
cPr=cyclopropyl
iPr=isopropyl
Bu=n-butyl
cBu=cyclobutyl
iBu=isobutyl
sBu=sec-butyl
tBu=tert-butyl
cPen=cyclopentyl
cHex=cyclohexyl

TABLE 1

Compounds of the formula Ia-S (Ia-S)

| Ex. No. | R¹ | R² | R³ | R⁴ | R⁵ |
|---|---|---|---|---|---|
| 1. | H | H | H | H | H |
| 2. | F | H | H | H | H |
| 3. | F | F | H | H | H |
| 4. | F | H | F | H | H |
| 5. | F | H | H | F | H |
| 6. | F | H | H | H | F |
| 7. | H | F | H | F | H |
| 8. | F | Me | H | H | F |
| 9. | Ph | H | H | H | H |
| 10. | OCH$_2$C≡CH | H | H | H | H |
| 11. | OS(O)$_2$Me | H | H | H | H |
| 12. | F | H | H | H | Cl |
| 13. | CF$_3$ | H | H | H | H |
| 14. | OCHF$_2$ | H | H | H | H |
| 15. | S(O)CH$_3$ | H | H | H | H |
| 16. | SCF$_3$ | H | H | H | H |
| 17. | CN | H | H | H | H |
| 18. | Me | H | H | H | H |
| 19. | H | OMe | H | OMe | H |
| 20. | F | H | H | H | CF$_3$ |
| 21. | F | CF$_3$ | H | H | F |
| 22. | OCH$_2$CH$_2$O | | H | F | H |
| 23. | S(O)CF$_3$ | H | H | H | H |
| 24. | F | H | C(O)OMe | H | H |
| 25. | F | H | C(O)OEt | H | H |
| 26. | OCF$_3$ | H | H | H | H |
| 27. | OCF$_2$O | | H | H | H |
| 28. | OCH$_2$OCH$_2$ | | H | H | H |
| 29. | Br | H | H | H | H |
| 30. | I | H | H | H | H |
| 31. | Cl | H | Cl | H | H |
| 32. | Cl | H | H | H | Cl |
| 33. | H | Cl | Cl | H | H |
| 34. | Cl | Cl | Cl | H | H |
| 35. | Cl | Cl | H | Cl | H |
| 36. | Cl | Cl | H | H | Cl |
| 37. | Cl | H | Cl | Cl | H |
| 38. | Cl | H | H | Cl | Cl |
| 39. | H | Cl | Cl | Cl | H |
| 40. | NO$_2$ | H | H | H | H |
| 41. | H | Cl | H | H | H |
| 42. | H | H | Cl | H | H |
| 43. | Cl | Cl | H | H | H |
| 44. | Cl | H | H | Cl | H |
| 45. | H | Cl | H | Cl | H |
| 46. | C(O)OEt | H | H | H | H |
| 47. | Me | H | H | H | H |
| 48. | H | OMe | H | H | H |
| 49. | H | H | OMe | H | H |
| 50. | H | OEt | H | H | H |
| 51. | H | OPr | H | H | H |
| 52. | H | OiPr | H | H | H |
| 53. | H | OCHF$_2$ | H | H | H |
| 54. | H | OCF$_3$ | H | H | H |
| 55. | C(O)OMe | H | H | H | H |
| 56. | CH$_2$OMe | H | H | H | H |
| 57. | F | Cl | H | H | H |
| 58. | Me | H | H | H | Me |
| 59. | OEt | Me | H | H | H |
| 60. | F | Me | H | H | H |
| 61. | H | Me | H | H | H |
| 62. | H | H | Me | H | H |

TABLE 1-continued

Compounds of the formula Ia-S (Ia-S)

| Ex. No. | R¹ | R² | R³ | R⁴ | R⁵ |
|---|---|---|---|---|---|
| 63. | OMe | H | H | H | H |
| 64. | H | H | OMe | H | H |
| 65. | H | CN | H | H | H |
| 66. | H | C(O)OMe | H | H | H |
| 67. | C(O)OH | H | H | H | H |
| 68. | H | F | F | H | H |
| 69. | F | H | H | H | NO₂ |
| 70. | F | H | F | H | F |
| 71. | F | F | H | H | F |
| 72. | Et | H | H | H | Et |
| 73. | NO₂ | C(O)OMe | H | H | H |
| 74. | F | F | F | H | H |
| 75. | F | F | H | F | H |
| 76. | H | F | F | F | H |
| 77. | F | H | F | F | H |
| 78. | Me | H | Me | H | H |
| 79. | Me | H | H | Me | H |
| 80. | H | Me | Me | H | H |
| 81. | F | H | H | CF₃ | H |
| 82. | F | CF₃ | H | H | H |
| 83. | F | H | Br | H | H |
| 84. | S(O)₂CF₃ | H | H | H | H |
| 85. | Cl | H | H | H | H |
| 86. | Me | Me | H | H | H |
| 87. | H | Me | H | Me | H |
| 88. | Me | H | H | H | Et |
| 89. | F | H | H | H | OEt |
| 90. | F | H | CF₃ | H | H |
| 91. | Me | H | Me | H | Me |
| 92. | OMe | H | H | NO₂ | H |
| 93. | F | F | F | F | F |
| 94. | F | H | H | H | OMe |
| 95. | OMe | H | H | H | OMe |
| 96. | OEt | H | H | H | OEt |
| 97. | Me | NO₂ | H | H | H |
| 98. | Cl | H | F | H | H |
| 99. | NO₂ | H | Cl | H | H |
| 100. | NO₂ | H | H | Me | H |
| 101. | H | CF₃ | F | H | H |
| 102. | H | F | H | CF₃ | H |
| 103. | H | CF₃ | H | CF₃ | H |
| 104. | CF₃ | H | H | CF₃ | H |
| 105. | H | Br | H | Br | H |
| 106. | H | NO₂ | H | NO₂ | H |
| 107. | Me | Me | H | Me | Me |
| 108. | F | H | H | H | I |
| 109. | NH₂ | H | H | H | F |
| 110. | NH₂ | H | H | H | H |
| 111. | F | H | H | H | Br |
| 112. | Br | H | H | H | Br |
| 113. | F | H | H | H | C(O)OMe |
| 114. | F | H | H | H | NMe₂ |
| 115. | F | H | H | H | NEt₂ |
| 116. | Cl | H | H | H | Me |
| 117. | Cl | H | H | H | OCHF₂ |
| 118. | Cl | H | H | H | OMe |
| 119. | Cl | H | H | H | OEt |
| 120. | Cl | H | H | H | OPr |
| 121. | Cl | H | H | H | OiPr |
| 122. | Cl | H | H | H | OCH₂CF₃ |
| 123. | OBu | H | H | H | H |
| 124. | F | H | H | H | OBu |

TABLE 1-continued

Compounds of the formula Ia-S (Ia-S)

| Ex. No. | R¹ | R² | R³ | R⁴ | R⁵ |
|---|---|---|---|---|---|
| 125. | F | H | H | H | OPr |
| 126. | F | H | H | H | OiPr |
| 127. | Cl | H | H | H | OiBu |
| 128. | F | H | H | H | OCHF$_2$ |
| 129. | Cl | H | H | H | OBu |
| 130. | F | H | H | H | OCH$_2$C≡CH |
| 131. | OCH$_2$C(O)OMe | H | H | H | H |
| 132. | OCH$_2$C(O)OEt | H | H | H | H |
| 133. | O(CH$_2$)$_2$OMe | H | H | H | H |
| 134. | O(CH$_2$)$_2$OEt | H | H | H | H |
| 135. | Me | H | H | H | OMe |
| 136. | Me | iPr | H | H | OMe |
| 137. | OEt | H | H | H | CF$_3$ |
| 138. | CH$_2$OEt | H | H | H | H |
| 139. | OC(O)Me | H | H | H | H |
| 140. | OCH$_2$Ph | H | H | H | H |
| 141. | OCH$_2$CH=CH$_2$ | H | H | H | H |
| 142. | Cl | H | H | H | OCH$_2$CH=CH$_2$ |
| 143. | Cl | H | H | H | OCH$_2$C≡CH |
| 144. | C(O)OPr | H | H | H | H |
| 145. | C(O)OiPr | H | H | H | H |
| 146. | C(O)OBu | H | H | H | H |
| 147. | C(O)OsBu | H | H | H | H |
| 148. | C(O)OiBu | H | H | H | H |
| 149. | C(O)OCH$_2$CH=CH$_2$ | H | H | H | H |
| 150. | C(O)OCH$_2$C≡CH | H | H | H | H |
| 151. | C(O)OcPen | H | H | H | H |
| 152. | OEt | H | H | H | Me |
| 153. | OPr | H | H | H | Me |
| 154. | OBu | H | H | H | Me |
| 155. | Me | H | H | H | OCH$_2$CH=CH$_2$ |
| 156. | Me | H | H | H | OCH$_2$C≡CH |
| 157. | OCH$_2$cPr | H | H | H | H |
| 158. | OcPen | H | H | H | H |
| 159. | OcHex | H | H | H | H |
| 160. | C(O)OCH$_2$Ph | H | H | H | H |
| 161. | C(O)OCH$_2$Ph(2-Cl) | H | H | H | H |
| 162. | C(O)OCH$_2$Ph(3-Cl) | H | H | H | H |
| 163. | C(O)OCH$_2$Ph(4-Cl) | H | H | H | H |
| 164. | CH$_2$OBu | H | H | H | H |
| 165. | Me | Me | H | H | Me |
| 166. | Cl | H | H | H | C(O)OMe |
| 167. | Cl | H | H | H | C(O)OEt |
| 168. | Cl | H | H | H | C(O)OPr |
| 169. | Cl | H | H | H | C(O)OiPr |
| 170. | Cl | H | H | H | C(O)OBu |
| 171. | Cl | H | H | H | C(O)OsBu |
| 172. | Cl | H | H | H | C(O)OiBu |
| 173. | Cl | H | H | H | C(O)OCH$_2$Ph |
| 174. | Cl | H | H | H | C(O)OCH$_2$Ph(2-Cl) |
| 175. | Cl | H | H | H | C(O)OCH$_2$Ph(3-Cl) |
| 176. | Cl | H | H | H | C(O)OCH$_2$Ph(4-Cl) |
| 177. | Cl | H | H | OMe | H |
| 178. | Cl | H | H | OEt | H |
| 179. | Cl | H | H | OPr | H |
| 180. | Cl | H | H | OiPr | H |
| 181. | Cl | H | H | OBu | H |
| 182. | Cl | H | H | OCH$_2$CH=CH$_2$ | H |
| 183. | Cl | H | H | OCH$_2$C≡CH | H |
| 184. | Et | H | H | H | OMe |
| 185. | Cl | H | H | H | C(O)OH |
| 186. | F | H | H | H | C(O)OH |

TABLE 1-continued

Compounds of the formula Ia-S (Ia-S)

| Ex. No. | R¹ | R² | R³ | R⁴ | R⁵ |
|---|---|---|---|---|---|
| 187. | F | H | H | H | C(O)OEt |
| 188. | F | H | H | H | C(O)OPr |
| 189. | F | H | H | H | C(O)OiPr |
| 190. | F | H | H | H | C(O)OBu |
| 191. | F | H | H | H | C(O)OsBu |
| 192. | F | H | H | H | C(O)OiBu |
| 193. | F | H | H | H | C(O)OCH$_2$Ph |
| 194. | F | H | H | H | C(O)OCH$_2$Ph(2-Cl) |
| 195. | F | H | H | H | C(O)OCH$_2$Ph(3-Cl) |
| 196. | F | H | H | H | C(O)OCH$_2$Ph(4-Cl) |
| 197. | OEt | H | H | H | Et |
| 198. | OPr | H | H | H | Et |
| 199. | OiPr | H | H | H | Et |
| 200. | OCH$_2$CH=CH$_2$ | H | H | H | Et |
| 201. | OCH$_2$C≡CH | H | H | H | Et |
| 202. | F | F | H | F | F |
| 203. | C(O)OMe | Me | H | H | H |
| 204. | C(O)OEt | Me | H | H | H |
| 205. | C(O)OiBu | Me | H | H | H |
| 206. | Me | H | H | Me | OMe |
| 207. | Me | H | H | Me | OEt |
| 208. | Me | H | H | Me | OPr |
| 209. | F | Me | H | H | Cl |
| 210. | Cl | H | H | F | H |
| 211. | F | H | H | F | Cl |
| 212. | F | H | H | Cl | H |
| 213. | Cl | H | H | CF$_3$ | H |
| 214. | Cl | Me | H | H | H |
| 215. | F | H | H | OMe | H |
| 216. | F | H | H | CF$_3$ | H |
| 217. | Cl | H | OCH$_2$O | | H |
| 218. | F | H | H | Me | Cl |
| 219. | OMe | H | H | Cl | H |
| 220. | Me | H | H | F | H |
| 221. | OMe | H | H | OMe | H |
| 222. | H | OCF$_2$O | | H | H |

TABLE 2

Compounds of the formula Ia-R (Ia-R)

| Ex. No. | R¹ | R² | R³ | R⁴ | R⁵ |
|---|---|---|---|---|---|
| 223. | H | H | H | H | H |
| 224. | F | H | H | H | H |
| 225. | F | F | H | H | H |
| 226. | F | H | F | H | H |

TABLE 2-continued

Compounds of the formula Ia-R (Ia-R)

| Ex. No. | R¹ | R² | R³ | R⁴ | R⁵ |
|---|---|---|---|---|---|
| 227. | F | H | H | F | H |
| 228. | F | H | H | H | F |
| 229. | H | F | H | F | H |
| 230. | F | Me | H | H | F |
| 231. | Ph | H | H | H | H |
| 232. | OCH$_2$C≡CH | H | H | H | H |
| 233. | OS(O)$_2$Me | H | H | H | H |
| 234. | F | H | H | H | Cl |
| 235. | CF$_3$ | H | H | H | H |
| 236. | OCHF$_2$ | H | H | H | H |
| 237. | S(O)CH$_3$ | H | H | H | H |
| 238. | SCF$_3$ | H | H | H | H |
| 239. | CN | H | H | H | H |
| 240. | Me | H | H | H | H |
| 241. | H | OMe | H | OMe | H |
| 242. | F | H | H | H | CF$_3$ |
| 243. | F | CF$_3$ | H | H | F |
| 244. | OCH$_2$CH$_2$O | | H | F | H |
| 245. | S(O)CF$_3$ | H | H | H | H |
| 246. | F | H | C(O)OMe | H | H |
| 247. | F | H | C(O)OEt | H | H |
| 248. | OCF$_3$ | H | H | H | H |
| 249. | OCF$_2$O | | H | H | H |
| 250. | OCH$_2$OCH$_2$ | | H | H | H |
| 251. | Br | H | H | H | H |
| 252. | I | H | H | H | H |
| 253. | Cl | H | Cl | H | H |
| 254. | Cl | H | H | H | Cl |
| 255. | H | Cl | Cl | H | H |
| 256. | Cl | Cl | Cl | H | H |
| 257. | Cl | Cl | H | Cl | H |
| 258. | Cl | Cl | H | H | Cl |
| 259. | Cl | H | Cl | Cl | H |
| 260. | Cl | H | H | Cl | Cl |
| 261. | H | Cl | Cl | Cl | H |
| 262. | NO$_2$ | H | H | H | H |
| 263. | H | Cl | H | H | H |
| 264. | H | H | Cl | H | H |
| 265. | Cl | Cl | H | H | H |
| 266. | Cl | H | H | Cl | H |
| 267. | H | Cl | H | Cl | H |
| 268. | C(O)OEt | H | H | H | H |
| 269. | Me | H | H | H | H |
| 270. | H | OMe | H | H | H |
| 271. | H | H | OMe | H | H |
| 272. | H | OEt | H | H | H |
| 273. | H | OPr | H | H | H |
| 274. | H | OiPr | H | H | H |
| 275. | H | OCHF$_2$ | H | H | H |
| 276. | H | OCF$_3$ | H | H | H |
| 277. | C(O)OMe | H | H | H | H |
| 278. | CH$_2$OMe | H | H | H | H |
| 279. | F | Cl | H | H | H |
| 280. | Me | H | H | H | Me |
| 281. | OEt | Me | H | H | H |
| 282. | F | Me | H | H | H |
| 283. | H | Me | H | H | H |
| 284. | H | H | Me | H | H |
| 285. | OMe | H | H | H | H |
| 286. | H | H | OMe | H | H |
| 287. | H | CN | H | H | H |
| 288. | H | C(O)OMe | H | H | H |

TABLE 2-continued

Compounds of the formula Ia-R

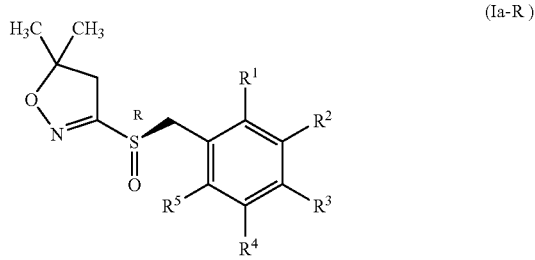

(Ia-R)

| Ex. No. | R¹ | R² | R³ | R⁴ | R⁵ |
|---|---|---|---|---|---|
| 289. | C(O)OH | H | H | H | H |
| 290. | H | F | F | H | H |
| 291. | F | H | H | H | $NO_2$ |
| 292. | F | H | F | H | F |
| 293. | F | F | H | H | F |
| 294. | Et | H | H | H | Et |
| 295. | $NO_2$ | C(O)OMe | H | H | H |
| 296. | F | F | F | H | H |
| 297. | F | F | H | F | H |
| 298. | H | F | F | F | H |
| 299. | F | H | F | F | H |
| 300. | Me | H | Me | H | H |
| 301. | Me | H | H | Me | H |
| 302. | H | Me | Me | H | H |
| 303. | F | H | H | $CF_3$ | H |
| 304. | F | $CF_3$ | H | H | H |
| 305. | F | H | Br | H | H |
| 306. | $S(O)_2CF_3$ | H | H | H | H |
| 307. | I | H | H | H | H |
| 308. | Me | Me | H | H | H |
| 309. | H | Me | H | Me | H |
| 310. | H | OMe | H | OMe | H |
| 311. | Me | H | H | H | Et |
| 312. | F | H | H | H | OEt |
| 313. | F | H | $CF_3$ | H | H |
| 314. | Me | H | Me | H | Me |
| 315. | OMe | H | H | $NO_2$ | H |
| 316. | F | F | F | F | F |
| 317. | F | H | H | H | OMe |
| 318. | OMe | H | H | H | OMe |
| 319. | OEt | H | H | H | OEt |
| 320. | Me | $NO_2$ | H | H | H |
| 321. | Cl | H | F | H | H |
| 322. | $NO_2$ | H | Cl | H | H |
| 323. | $NO_2$ | H | H | Me | H |
| 324. | H | $CF_3$ | F | H | H |
| 325. | H | F | H | $CF_3$ | H |
| 326. | H | $CF_3$ | H | $CF_3$ | H |
| 327. | $CF_3$ | H | H | $CF_3$ | H |
| 328. | H | Br | H | Br | H |
| 329. | H | $NO_2$ | H | $NO_2$ | H |
| 330. | Me | Me | H | Me | Me |
| 331. | F | H | H | H | I |
| 332. | $NH_2$ | H | H | H | F |
| 333. | F | Me | H | H | F |
| 334. | $NH_2$ | H | H | H | H |
| 335. | F | H | H | H | Br |
| 336. | Br | H | H | H | Br |
| 337. | F | H | H | H | C(O)OMe |
| 338. | F | H | H | H | $NMe_2$ |
| 339. | F | H | H | H | $NEt_2$ |
| 340. | Cl | H | H | H | Me |
| 341. | Cl | H | H | H | $OCHF_2$ |
| 342. | Cl | H | H | H | OMe |
| 343. | Cl | H | H | H | OEt |
| 344. | Cl | H | H | H | OPr |
| 345. | Cl | H | H | H | OiPr |
| 346. | Cl | H | H | H | $OCH_2CF_3$ |
| 347. | OBu | H | H | H | H |
| 348. | F | H | H | H | OBu |
| 349. | F | H | H | H | OPr |
| 350. | F | H | H | H | OiPr |

TABLE 2-continued

Compounds of the formula Ia-R

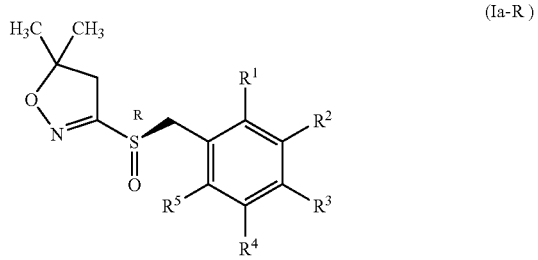

(Ia-R)

| Ex. No. | R¹ | R² | R³ | R⁴ | R⁵ |
|---|---|---|---|---|---|
| 351. | Cl | H | H | H | OiBu |
| 352. | F | H | H | H | OCHF$_2$ |
| 353. | Cl | H | H | H | OBu |
| 354. | F | H | H | H | OCH$_2$C≡CH |
| 355. | OCH$_2$C(O)OMe | H | H | H | H |
| 356. | OCH$_2$C(O)OEt | H | H | H | H |
| 357. | O(CH$_2$)$_2$OMe | H | H | H | H |
| 358. | O(CH$_2$)$_2$OEt | H | H | H | H |
| 359. | Me | H | H | H | OMe |
| 360. | Me | iPr | H | H | OMe |
| 361. | OEt | H | H | H | CF$_3$ |
| 362. | CH$_2$OEt | H | H | H | H |
| 363. | OC(O)Me | H | H | H | H |
| 364. | OCH$_2$Ph | H | H | H | H |
| 365. | OCH$_2$CH=CH$_2$ | H | H | H | H |
| 366. | Cl | H | H | H | OCH$_2$CH=CH$_2$ |
| 367. | Cl | H | H | H | OCH$_2$C≡CH |
| 368. | C(O)OPr | H | H | H | H |
| 369. | C(O)OiPr | H | H | H | H |
| 370. | C(O)OBu | H | H | H | H |
| 371. | C(O)OsBu | H | H | H | H |
| 372. | C(O)OiBu | H | H | H | H |
| 373. | C(O)OCH$_2$CH=CH$_2$ | H | H | H | H |
| 374. | C(O)OCH$_2$C≡CH | H | H | H | H |
| 375. | C(O)OcPen | H | H | H | H |
| 376. | OEt | H | H | H | Me |
| 377. | OPr | H | H | H | Me |
| 378. | OBu | H | H | H | Me |
| 379. | Me | H | H | H | OCH$_2$CH=CH$_2$ |
| 380. | Me | H | H | H | OCH$_2$C≡CH |
| 381. | OCH$_2$cPr | H | H | H | H |
| 382. | OcPen | H | H | H | H |
| 383. | OcHex | H | H | H | H |
| 384. | C(O)OCH$_2$Ph | H | H | H | H |
| 385. | C(O)OCH$_2$Ph(2-Cl) | H | H | H | H |
| 386. | C(O)OCH$_2$Ph(3-Cl) | H | H | H | H |
| 387. | C(O)OCH$_2$Ph(4-Cl) | H | H | H | H |
| 388. | CH$_2$OBu | H | H | H | H |
| 389. | Me | Me | H | H | Me |
| 390. | Cl | H | H | H | C(O)OMe |
| 391. | Cl | H | H | H | C(O)OEt |
| 392. | Cl | H | H | H | C(O)OPr |
| 393. | Cl | H | H | H | C(O)OiPr |
| 394. | Cl | H | H | H | C(O)OBu |
| 395. | Cl | H | H | H | C(O)OsBu |
| 396. | Cl | H | H | H | C(O)OiBu |
| 397. | Cl | H | H | H | C(O)OCH$_2$Ph |
| 398. | Cl | H | H | H | C(O)OCH$_2$Ph(2-Cl) |
| 399. | Cl | H | H | H | C(O)OCH$_2$Ph(3-Cl) |
| 400. | Cl | H | H | H | C(O)OCH$_2$Ph(4-Cl) |
| 401. | Cl | H | H | OMe | H |
| 402. | Cl | H | H | OEt | H |
| 403. | Cl | H | H | OPr | H |
| 404. | Cl | H | H | OiPr | H |
| 405. | Cl | H | H | OBu | H |
| 406. | Cl | H | H | OCH$_2$CH=CH$_2$ | H |
| 407. | Cl | H | H | OCH$_2$C≡CH | H |
| 408. | Et | H | H | H | OMe |
| 409. | Cl | H | H | H | C(O)OH |
| 410. | F | H | H | H | C(O)OH |
| 411. | F | H | H | H | C(O)OEt |
| 412. | F | H | H | H | C(O)OPr |

TABLE 2-continued

Compounds of the formula Ia-R (Ia-R)

| Ex. No. | R¹ | R² | R³ | R⁴ | R⁵ |
|---|---|---|---|---|---|
| 413. | F | H | H | H | C(O)OiPr |
| 414. | F | H | H | H | C(O)OBu |
| 415. | F | H | H | H | C(O)OsBu |
| 416. | F | H | H | H | C(O)OiBu |
| 417. | F | H | H | H | C(O)OCH$_2$Ph |
| 418. | F | H | H | H | C(O)OCH$_2$Ph(2-Cl) |
| 419. | F | H | H | H | C(O)OCH$_2$Ph(3-Cl) |
| 420. | F | H | H | H | C(O)OCH$_2$Ph(4-Cl) |
| 421. | OEt | H | H | H | Et |
| 422. | OPr | H | H | H | Et |
| 423. | OiPr | H | H | H | Et |
| 424. | OCH$_2$CH=CH$_2$ | H | H | H | Et |
| 425. | OCH$_2$C≡CH | H | H | H | Et |
| 426. | F | F | H | F | F |
| 427. | C(O)OMe | Me | H | H | H |
| 428. | C(O)OEt | Me | H | H | H |
| 429. | C(O)OiBu | Me | H | H | H |
| 430. | Me | H | H | Me | OMe |
| 431. | Me | H | H | Me | OEt |
| 432. | Me | H | H | Me | OPr |
| 433. | F | Me | H | H | Cl |
| 434. | Cl | H | H | F | H |
| 435. | F | H | H | F | Cl |
| 436. | F | H | H | Cl | H |
| 437. | Cl | H | H | CF$_3$ | H |
| 438. | Cl | Me | H | H | H |
| 439. | F | H | H | OMe | H |
| 440. | F | H | H | CF$_3$ | H |
| 441. | Cl | H | H | OCH$_2$O | H |
| 442. | F | H | H | Me | Cl |
| 443. | OMe | H | H | Cl | H |
| 444. | Me | H | H | F | H |
| 445. | OMe | H | H | OMe | H |
| 446. | H | H | OCF$_2$O | H | H |

TABLE 3

Compounds of the formula Ib-S (Ib-S)

| Ex. No. | R⁶ | R⁷ | R⁸ |
|---|---|---|---|
| 447. | CF$_3$ | Ph | Cl |
| 448. | Ph | Me | Cl |
| 449. | CF$_3$ | Ph | SO$_2$Me |
| 450. | CF$_3$ | Ph | NMe$_2$ |
| 451. | CF$_3$ | tBu | Cl |
| 452. | CF$_3$ | H | Cl |
| 453. | CF$_3$ | CHF$_2$ | Cl |
| 454. | Cl | CHF$_2$ | CF$_3$ |
| 455. | OEt | Me | CF$_3$ |
| 456. | CF$_3$ | Me | OMe |

TABLE 3-continued

Compounds of the formula Ib-S (Ib-S)

| Ex. No. | R⁶ | R⁷ | R⁸ |
|---|---|---|---|
| 457. | $CF_3$ | Me | OPh(2-Cl) |
| 458. | $CF_3$ | Me | OcPen |
| 459. | $CF_3$ | Me | CN |
| 460. | Cl | Et | Cl |
| 461. | $CHF_2$ | Me | Cl |
| 462. | $CF_3$ | —$(CH_2)_3$O— | |
| 463. | $CF_3$ | H | Cl |
| 464. | H | Me | Cl |
| 465. | Me | Me | Me |
| 466. | Me | Me | Cl |
| 467. | Cl | Me | Cl |
| 468. | $CF_3$ | Me | Cl |
| 469. | Cl | Me | $CF_3$ |
| 470. | $CF_3$ | Me | F |
| 471. | $CF_3$ | Me | OH |
| 472. | OMe | Me | $CF_3$ |
| 473. | $CF_3$ | Me | OEt |
| 474. | $CF_3$ | Me | OiPr |
| 475. | $CF_3$ | Me | OPr |
| 476. | $CF_3$ | Me | OtBu |
| 477. | $CF_3$ | Me | OBu |
| 478. | $CF_3$ | Me | OcHex |
| 479. | $CF_3$ | Me | $OCH_2cPr$ |
| 480. | $CF_3$ | Me | $OCH_2cPen$ |
| 481. | $CF_3$ | Me | $OCH_2cHex$ |
| 482. | $CF_3$ | Me | $OCH_2C\equiv CH$ |
| 483. | $CF_3$ | Me | $OCHF_2$ |
| 484. | $OCHF_2$ | Me | $CF_3$ |
| 485. | $CF_3$ | Me | $OCH_2CHF_2$ |
| 486. | $CF_3$ | Me | $OCH_2CF_3$ |
| 487. | $CF_3$ | Me | $OCH_2CN$ |
| 488. | $CF_3$ | Me | $OCH_2Ph$ |
| 489. | $CF_3$ | Me | OPh |
| 490. | $CF_3$ | Me | OPh(3-Cl) |
| 491. | $CF_3$ | Me | OPh(3-OMe) |
| 492. | $CF_3$ | Me | OPh(4-Cl) |
| 493. | $CF_3$ | Me | OPh(4-Me) |
| 494. | $CF_3$ | Me | OPh(4-OMe) |
| 495. | $CF_3$ | Me | OC(O)Me |
| 496. | $CF_3$ | Me | $SO_2Me$ |
| 497. | $CF_3$ | Me | SEt |
| 498. | $CF_3$ | Me | $SO_2Et$ |
| 499. | $CF_3$ | Me | $SO_2Ph$ |
| 500. | $CF_3$ | Me | Me |
| 501. | $CF_3$ | Me | Et |
| 502. | $CF_3$ | Et | Cl |
| 503. | Cl | Et | $CF_3$ |
| 504. | $CF_3$ | iPr | Cl |
| 505. | Cl | iPr | $CF_3$ |
| 506. | $CF_3$ | Pr | Cl |
| 507. | Cl | Pr | $CF_3$ |
| 508. | $CF_3$ | tBu | Cl |
| 509. | Cl | tBu | $CF_3$ |
| 510. | $CF_3$ | sBu | Cl |
| 511. | Cl | sBu | $CF_3$ |
| 512. | $CF_3$ | iBu | Cl |
| 513. | Cl | iBu | $CF_3$ |
| 514. | $CF_3$ | Bu | Cl |
| 515. | Cl | Bu | $CF_3$ |
| 516. | $CF_3$ | $CH_2Ph$ | Cl |
| 517. | Cl | $CH_2Ph$ | $CF_3$ |
| 518. | $CF_3$ | cPen | Cl |
| 519. | Cl | cPen | $CF_3$ |
| 520. | $CF_3$ | cHex | Cl |
| 521. | $CF_3$ | $CH_2cPr$ | Cl |
| 522. | Cl | $CH_2cPr$ | $CF_3$ |
| 523. | $CF_3$ | CHMecPr | Cl |
| 524. | Cl | CHMecPr | $CF_3$ |
| 525. | $CF_3$ | $CH_2cPr(2-Me)$ | Cl |
| 526. | Cl | $CH_2cPr(2-Me)$ | $CF_3$ |
| 527. | $CF_3$ | $CH_2cBu$ | Cl |
| 528. | Cl | $CH_2cBu$ | $CF_3$ |
| 529. | $CF_3$ | $CH_2cPen$ | Cl |
| 530. | Cl | $CH_2cPen$ | $CF_3$ |
| 531. | $CF_3$ | $CH_2cHex$ | Cl |
| 532. | Cl | $CH_2cHex$ | $CF_3$ |
| 533. | $CF_3$ | $CH_2CH=CH_2$ | Cl |
| 534. | Cl | $CH_2CH=CH_2$ | $CF_3$ |
| 535. | $CF_3$ | $CH_2C\equiv CH$ | Cl |
| 536. | Cl | $CH_2C\equiv CH$ | $CF_3$ |
| 537. | $CF_3$ | $CHMeC\equiv CH$ | Cl |
| 538. | Cl | $CHMeC\equiv CH$ | $CF_3$ |
| 539. | $CF_3$ | $CH_2C\equiv CMe$ | Cl |
| 540. | Cl | $CH_2C\equiv CMe$ | $CF_3$ |
| 541. | $CF_3$ | $CHF_2$ | OMe |
| 542. | OMe | $CHF_2$ | $CF_3$ |
| 543. | $CF_3$ | $CH_2CF_3$ | Cl |
| 544. | Cl | $CH_2CF_3$ | $CF_3$ |
| 545. | $CF_3$ | $CH_2OMe$ | Cl |
| 546. | Cl | $CH_2OMe$ | $CF_3$ |
| 547. | $CF_3$ | $CH_2OEt$ | Cl |
| 548. | Cl | $CH_2OEt$ | $CF_3$ |
| 549. | $CF_3$ | $CH_2CH_2OH$ | Cl |
| 550. | Cl | $CH_2CH_2OH$ | $CF_3$ |
| 551. | $CF_3$ | $CH_2CH_2OMe$ | Cl |
| 552. | Cl | $CH_2CH_2OMe$ | $CF_3$ |
| 553. | $CF_3$ | $CH_2CH_2OEt$ | Cl |
| 554. | Cl | $CH_2CH_2OEt$ | $CF_3$ |
| 555. | $CF_3$ | $CH_2SMe$ | Cl |
| 556. | Cl | $CH_2SMe$ | $CF_3$ |
| 557. | $CF_3$ | $CH_2SO_2Me$ | Cl |
| 558. | Cl | $CH_2SO_2Me$ | $CF_3$ |
| 559. | $CF_3$ | $CH_2CN$ | Cl |
| 560. | Cl | $CH_2CN$ | $CF_3$ |
| 561. | $CF_3$ | $CH_2C(O)OEt$ | Cl |
| 562. | Cl | $CH_2C(O)OEt$ | $CF_3$ |
| 563. | $CF_3$ | $CH_2C(O)NH_2$ | Cl |
| 564. | Cl | $CH_2C(O)NH_2$ | $CF_3$ |
| 565. | $CF_3$ | $CH_2C(O)NMe_2$ | Cl |
| 566. | Cl | $CH_2C(O)NMe_2$ | $CF_3$ |
| 567. | $CF_3$ | $CH_2C(O)Me$ | Cl |
| 568. | Cl | $CH_2C(O)Me$ | $CF_3$ |
| 569. | $CF_3$ | $CH_2CH_2C(O)Me$ | Cl |
| 570. | Me | Ph | Me |
| 571. | Me | Ph | Cl |
| 572. | Et | Ph | Cl |
| 573. | Pr | Ph | Cl |
| 574. | iPr | Ph | Cl |
| 575. | tBu | Ph | Cl |
| 576. | $CF_3$ | Ph | H |
| 577. | $CF_3$ | Ph | Me |
| 578. | $CF_3$ | Ph | $CF_3$ |
| 579. | $CF_3$ | Ph | F |
| 580. | $CF_3$ | Ph | OMe |

TABLE 3-continued

Compounds of the formula Ib-S

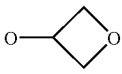

(Ib-S)

| Ex. No. | R⁶ | R⁷ | R⁸ |
|---|---|---|---|
| 581. | $CF_3$ | Ph | OEt |
| 582. | $CF_3$ | Ph | OiPr |
| 583. | $CF_3$ | Ph | OPr |
| 584. | $CF_3$ | Ph | OtBu |
| 585. | $CF_3$ | Ph | $OCHF_2$ |
| 586. | $CF_3$ | Ph | $SO_2Me$ |
| 587. | $CF_3$ | Ph | CN |
| 588. | $CF_3$ | Ph(2-Cl) | Cl |
| 589. | $CF_3$ | Ph(3-Cl) | Cl |
| 590. | $CF_3$ | Ph(4-Cl) | Cl |
| 591. | $CF_3$ | Ph(4-F) | Cl |
| 592. | $CF_3$ | Ph(4-OMe) | Cl |
| 593. | $CF_3$ | Ph(4-Me) | Cl |
| 594. | $CF_3$ | Ph(4-$NO_2$) | Cl |
| 595. | $CF_3$ | Ph(4-CN) | Cl |
| 596. | $CF_3$ | Ph(4-C(O)Me) | Cl |
| 597. | $CF_3$ | Ph(4-C(O)OMe) | Cl |
| 598. | $CF_3$ | pyrimidinyl-2-yl | Cl |
| 599. | $CF_3$ | 4,6-dimethoxypyrimidinyl-2-yl | Cl |
| 600. | $CF_3$ | $SO_2Me$ | Cl |
| 601. | $CF_3$ | $SO_2Ph$ | Cl |
| 602. | $CF_3$ | C(O)Me | Cl |
| 603. | $CF_3$ | C(O)Ph | Cl |
| 604. | $CF_3$ | C(O)OMe | Cl |
| 605. | $CF_3$ | tBu | OMe |
| 606. | Me | Me | $OCH_2CF_3$ |
| 607. | $CF_3$ | Me | oxetanyl |
| 608. | $CF_3$ | Me | H |
| 609. | $CF_3$ | Me | $SO_2iPr$ |
| 610. | $CF_3$ | Me | $CF_3$ |
| 611. | $CF_3$ | Me | $CHF_2$ |
| 612. | $CHF_2$ | Me | $CF_3$ |
| 613. | $CF_2CF_3$ | Me | $CF_3$ |
| 614. | $CF_3$ | Me | $CF_2CF_3$ |
| 615. | $CF_3$ | Me | $OCH_2CH_2OMe$ |
| 616. | $CF_3$ | Me | $OCH_2CH_2CH_2F$ |
| 617. | $CF_3$ | Me | $OCH(CH_2F)_2$ |
| 618. | $CF_3$ | Me | $OCH_2CF_2CHF_2$ |
| 619. | $CF_3$ | Me | $OCH_2CF=CH_2$ |
| 620. | $CF_3$ | Me | $OCH(Me)CF_3$ |
| 621. | $CF_3$ | Me | $OCH(Me)CH_2F$ |
| 622. | $CF_3$ | Me | $OCH_2CHF_2$ |
| 623. | $OCH_2CF_3$ | Me | $CF_3$ |
| 624. | $OCH_2CF_3$ | Me | $CHF_2$ |
| 625. | $CHF_2$ | Me | $CHF_2$ |
| 626. | $CHF_2$ | Me | $OCH_2CF_3$ |
| 627. | $CHF_2$ | Me | $OCHF_2$ |

TABLE 4

Compounds of the formula Ib-R (Ib-R)

| Ex. No. | R⁶ | R⁷ | R⁸ |
|---|---|---|---|
| 628. | $CF_3$ | Ph | Cl |
| 629. | Ph | Me | Cl |
| 630. | $CF_3$ | Ph | $SO_2Me$ |
| 631. | $CF_3$ | Ph | $NMe_2$ |
| 632. | $CF_3$ | tBu | Cl |
| 633. | $CF_3$ | H | Cl |
| 634. | $CF_3$ | $CHF_2$ | Cl |
| 635. | Cl | $CHF_2$ | $CF_3$ |
| 636. | OEt | Me | $CF_3$ |
| 637. | $CF_3$ | Me | OMe |
| 638. | $CF_3$ | Me | OPh(2-Cl) |
| 639. | $CF_3$ | Me | OcPen |
| 640. | $CF_3$ | Me | CN |
| 641. | Cl | Et | Cl |
| 642. | $CHF_2$ | Me | Cl |
| 643. | $CF_3$ | —$(CH_2)_3$O— | Cl |
| 644. | $CF_3$ | H | Cl |
| 645. | H | Me | Cl |
| 646. | Me | Me | Me |
| 647. | Me | Me | Cl |
| 648. | Cl | Me | Cl |
| 649. | $CF_3$ | Me | Cl |
| 650. | Cl | Me | $CF_3$ |
| 651. | $CF_3$ | Me | F |
| 652. | $CF_3$ | Me | OH |
| 653. | OMe | Me | $CF_3$ |
| 654. | $CF_3$ | Me | OEt |
| 655. | $CF_3$ | Me | OiPr |
| 656. | $CF_3$ | Me | OPr |
| 657. | $CF_3$ | Me | OtBu |
| 658. | $CF_3$ | Me | OBu |
| 659. | $CF_3$ | Me | OcHex |
| 660. | $CF_3$ | Me | $OCH_2cPr$ |
| 661. | $CF_3$ | Me | $OCH_2cPen$ |
| 662. | $CF_3$ | Me | $OCH_2cHex$ |
| 663. | $CF_3$ | Me | $OCH_2C≡CH$ |
| 664. | $CF_3$ | Me | $OCHF_2$ |
| 665. | $OCHF_2$ | Me | $CF_3$ |
| 666. | $CF_3$ | Me | $OCH_2CHF_2$ |
| 667. | $CF_3$ | Me | $OCH_2CF_3$ |
| 668. | $CF_3$ | Me | $OCH_2CN$ |
| 669. | $CF_3$ | Me | $OCH_2Ph$ |
| 670. | $CF_3$ | Me | OPh |
| 671. | $CF_3$ | Me | OPh(3-Cl) |
| 672. | $CF_3$ | Me | OPh(3-OMe) |
| 673. | $CF_3$ | Me | OPh(4-Cl) |
| 674. | $CF_3$ | Me | OPh(4-Me) |
| 675. | $CF_3$ | Me | OPh(4-OMe) |
| 676. | $CF_3$ | Me | OC(O)Me |
| 677. | $CF_3$ | Me | $SO_2Me$ |
| 678. | $CF_3$ | Me | SEt |
| 679. | $CF_3$ | Me | $SO_2Et$ |
| 680. | $CF_3$ | Me | $SO_2Ph$ |
| 681. | $CF_3$ | Me | Me |
| 682. | $CF_3$ | Me | Et |
| 683. | $CF_3$ | Et | Cl |
| 684. | Cl | Et | $CF_3$ |
| 685. | $CF_3$ | iPr | Cl |
| 686. | Cl | iPr | $CF_3$ |
| 687. | $CF_3$ | Pr | Cl |
| 688. | Cl | Pr | $CF_3$ |
| 689. | $CF_3$ | tBu | Cl |

TABLE 4-continued

Compounds of the formula Ib-R (Ib-R)

| Ex. No. | R⁶ | R⁷ | R⁸ |
|---|---|---|---|
| 690. | Cl | tBu | CF₃ |
| 691. | CF₃ | sBu | Cl |
| 692. | Cl | sBu | CF₃ |
| 693. | CF₃ | iBu | Cl |
| 694. | Cl | iBu | CF₃ |
| 695. | CF₃ | Bu | Cl |
| 696. | Cl | Bu | CF₃ |
| 697. | CF₃ | CH₂Ph | Cl |
| 698. | Cl | CH₂Ph | CF₃ |
| 699. | CF₃ | cPen | Cl |
| 700. | Cl | cPen | CF₃ |
| 701. | CF₃ | cHex | Cl |
| 702. | CF₃ | CH₂cPr | Cl |
| 703. | Cl | CH₂cPr | CF₃ |
| 704. | CF₃ | CHMecPr | Cl |
| 705. | Cl | CHMecPr | CF₃ |
| 706. | CF₃ | CH₂cPr(2-Me) | Cl |
| 707. | Cl | CH₂cPr(2-Me) | CF₃ |
| 708. | CF₃ | CH₂cBu | Cl |
| 709. | Cl | CH₂cBu | CF₃ |
| 710. | CF₃ | CH₂cPen | Cl |
| 711. | Cl | CH₂cPen | CF₃ |
| 712. | CF₃ | CH₂cHex | Cl |
| 713. | Cl | CH₂cHex | CF₃ |
| 714. | CF₃ | CH₂CH=CH₂ | Cl |
| 715. | Cl | CH₂CH=CH₂ | CF₃ |
| 716. | CF₃ | CH₂C≡CH | Cl |
| 717. | Cl | CH₂C≡CH | CF₃ |
| 718. | CF₃ | CHMeC≡CH | Cl |
| 719. | Cl | CHMeC≡CH | CF₃ |
| 720. | CF₃ | CH₂C≡CMe | Cl |
| 721. | Cl | CH₂C≡CMe | CF₃ |
| 722. | CF₃ | CHF₂ | OMe |
| 723. | OMe | CHF₂ | CF₃ |
| 724. | CF₃ | CH₂CF₃ | Cl |
| 725. | Cl | CH₂CF₃ | CF₃ |
| 726. | CF₃ | CH₂OMe | Cl |
| 727. | Cl | CH₂OMe | CF₃ |
| 728. | CF₃ | CH₂OEt | Cl |
| 729. | Cl | CH₂OEt | CF₃ |
| 730. | CF₃ | CH₂CH₂OH | Cl |
| 731. | Cl | CH₂CH₂OH | CF₃ |
| 732. | CF₃ | CH₂CH₂OMe | Cl |
| 733. | Cl | CH₂CH₂OMe | CF₃ |
| 734. | CF₃ | CH₂CH₂OEt | Cl |
| 735. | Cl | CH₂CH₂OEt | CF₃ |
| 736. | CF₃ | CH₂SMe | Cl |
| 737. | Cl | CH₂SMe | CF₃ |
| 738. | CF₃ | CH₂SO₂Me | Cl |
| 739. | Cl | CH₂SO₂Me | CF₃ |
| 740. | CF₃ | CH₂CN | Cl |
| 741. | Cl | CH₂CN | CF₃ |
| 742. | CF₃ | CH₂C(O)OEt | Cl |
| 743. | Cl | CH₂C(O)OEt | CF₃ |
| 744. | CF₃ | CH₂C(O)NH₂ | Cl |
| 745. | Cl | CH₂C(O)NH₂ | CF₃ |
| 746. | CF₃ | CH₂C(O)NMe₂ | Cl |
| 747. | Cl | CH₂C(O)NMe₂ | CF₃ |
| 748. | CF₃ | CH₂C(O)Me | Cl |
| 749. | Cl | CH₂C(O)Me | CF₃ |
| 750. | CF₃ | CH₂CH₂C(O)Me | Cl |
| 751. | Me | Ph | Me |
| 752. | Me | Ph | Cl |
| 753. | Et | Ph | Cl |
| 754. | Pr | Ph | Cl |
| 755. | iPr | Ph | Cl |
| 756. | tBu | Ph | Cl |
| 757. | CF₃ | Ph | H |
| 758. | CF₃ | Ph | Me |
| 759. | CF₃ | Ph | CF₃ |
| 760. | CF₃ | Ph | F |
| 761. | CF₃ | Ph | OMe |
| 762. | CF₃ | Ph | OEt |
| 763. | CF₃ | Ph | OiPr |
| 764. | CF₃ | Ph | OPr |
| 765. | CF₃ | Ph | OtBu |
| 766. | CF₃ | Ph | OCHF₂ |
| 767. | CF₃ | Ph | SO₂Me |
| 768. | CF₃ | Ph | CN |
| 769. | CF₃ | Ph(2-Cl) | Cl |
| 770. | CF₃ | Ph(3-Cl) | Cl |
| 771. | CF₃ | Ph(4-Cl) | Cl |
| 772. | CF₃ | Ph(4-F) | Cl |
| 773. | CF₃ | Ph(4-OMe) | Cl |
| 774. | CF₃ | Ph(4-Me) | Cl |
| 775. | CF₃ | Ph(4-NO₂) | Cl |
| 776. | CF₃ | Ph(4-CN) | Cl |
| 777. | CF₃ | Ph(4-C(O)Me) | Cl |
| 778. | CF₃ | Ph(4-C(O)OMe) | Cl |
| 779. | CF₃ | pyrimidinyl-2-yl | Cl |
| 780. | CF₃ | 4,6-dimethoxypyrimidinyl-2-yl | Cl |
| 781. | CF₃ | SO₂Me | Cl |
| 782. | CF₃ | SO₂Ph | Cl |
| 783. | CF₃ | C(O)Me | Cl |
| 784. | CF₃ | C(O)Ph | Cl |
| 785. | CF₃ | C(O)OMe | Cl |
| 786. | CF₃ | tBu | OMe |
| 787. | Me | Me | OCH₂CF₃ |
| 788. | CF₃ | Me | (oxetane-3,3-diyl dioxy) |
| 789. | CF₃ | Me | H |
| 790. | CF₃ | Me | SO₂iPr |
| 791. | CF₃ | Me | CF₃ |
| 792. | CF₃ | Me | CHF₂ |
| 793. | CHF₂ | Me | CF₃ |
| 794. | CF₂CF₃ | Me | CF₃ |
| 795. | CF₃ | Me | CF₂CF₃ |
| 796. | CF₃ | Me | OCH₂CH₂OMe |
| 797. | CF₃ | Me | OCH₂CH₂CH₂F |
| 798. | CF₃ | Me | OCH(CH₂F)₂ |
| 799. | CF₃ | Me | OCH₂CF₂CHF₂ |
| 800. | CF₃ | Me | OCH₂CF=CH₂ |
| 801. | CF₃ | Me | OCH(Me)CF₃ |
| 802. | CF₃ | Me | OCH(Me)CH₂F |
| 803. | CF₃ | Me | OCH₂CHF₂ |
| 804. | OCH₂CF₃ | Me | CF₃ |
| 805. | OCH₂CF₃ | Me | CHF₂ |
| 806. | CHF₂ | Me | CHF₂ |

TABLE 4-continued

Compounds of the formula Ib-R

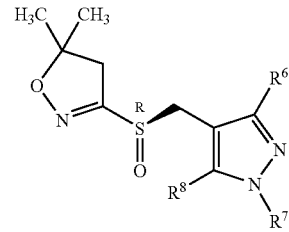
(Ib-R)

| Ex. No. | R⁶ | R⁷ | R⁸ |
|---|---|---|---|
| 807. | CHF₂ | Me | OCH₂CF₃ |
| 808. | CHF₂ | Me | OCHF₂ |

Retention times ($R_t$, in minutes) of selected compounds of Tables 1-4 of chiral compounds were determined by analytic chiral HPLC [Chiralcel® OD column (250×4.6 mm, particle size 5 μm), temperature 25° C., flow rate 0.6 ml/min, hexane/2-propanol 90:10 v/v].

TABLE 5

Compounds of the formula Ia-S

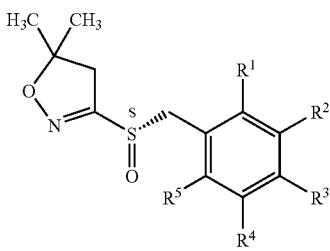
(Ia-S)

| Ex. No. | R¹ | R² | R³ | R⁴ | R⁵ | Physical data |
|---|---|---|---|---|---|---|
| 6 | F | H | H | H | F | $[\alpha]_D = +218.3°$ $R_t = 18.293$ min |
| 12 | F | H | H | H | Cl | $R_t = 18.729$ min |
| 32 | Cl | H | H | H | Cl | $[\alpha]_D = +136.3°$ $R_t = 19.746$ min |

TABLE 6

Compounds of the formula Ia-R

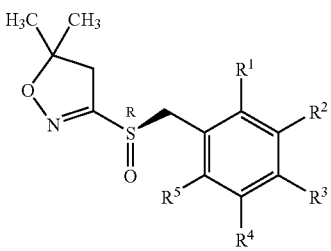
(Ia-R)

| Ex. No. | R¹ | R² | R³ | R⁴ | R⁵ | Physical data |
|---|---|---|---|---|---|---|
| 228 | F | H | H | H | F | $[\alpha]_D = -212.2°$ $R_t = 35.353$ min |

TABLE 6-continued

Compounds of the formula Ia-R

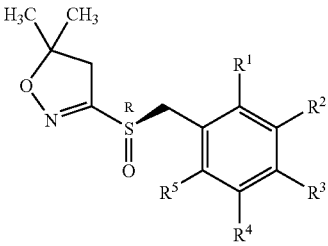
(Ia-R)

| Ex. No. | R¹ | R² | R³ | R⁴ | R⁵ | Physical data |
|---|---|---|---|---|---|---|
| 234 | F | H | H | H | Cl | $R_t = 34.250$ min |
| 254 | Cl | H | H | H | Cl | $[\alpha]_D = -127.9°$ $R_t = 32.760$ min |

TABLE 7

Compounds of the formula Ib-S

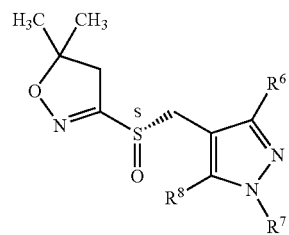
(Ib-S)

| Ex. No. | R⁶ | R⁷ | R⁸ | Physical data |
|---|---|---|---|---|
| 483 | CF₃ | Me | OCHF₂ | $[\alpha]_D = -70.7°$ $R_t = 11.124$ min |
| 610 | CF₃ | Me | CF₃ | $[\alpha]_D = -30.2°$ *$R_t = 4.658$ min |

*hexane/2-propanol 80:20 v/v.

Compounds of the formula Ib-R

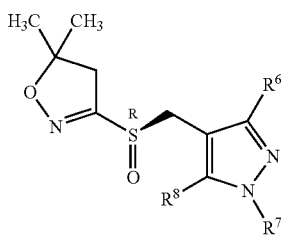
(Ib-R)

| Ex. No. | R⁶ | R⁷ | R⁸ | Physical data |
|---|---|---|---|---|
| 664 | CF₃ | Me | OCHF₂ | $[\alpha]_D = +63.4°$ $R_t = 14.244$ min |
| 791 | CF₃ | Me | CF₃ | $[\alpha]_D = +27.3°$ *$R_t = 5.490$ min |

*hexane/2-propanol 80:20 v/v.

In addition, NMR data for racemates comprising compounds of the formula (I) according to the invention were generated. Hereinbelow, to distinguish them from the stereochemically pure compounds of the formula (I), the racemates are referred to as compounds of the formula (Ia) and of the formula (Ib), respectively.

NMR data were measured at 400 MHz and in the solvent CDCl$_3$. The chemical shift δ is stated in ppm (TMS reference).

Compounds of the Formula (Ia) (Racemates)

(Ia)

| Ex. No. | R$^1$ | R$^2$ | R$^3$ | R$^4$ | R$^5$ |
|---|---|---|---|---|---|
| 6/228 | F | H | H | H | F |
| 12/234 | F | H | H | H | Cl |
| 32/254 | Cl | H | H | H | Cl |

NMR Compound 6/228 (CDCl$_3$, 400 MHz, δ in ppm): 1.47 (s, 3H, CH$_3$); 1.49 (s, 3H, CH$_3$); 3.07 (d, 1H, CH$_2$); 3.22 (d, 1H, CH$_2$); 4.36 (d, 1H, S(O)CH$_2$); 4.40 (d, 1H, S(O)CH$_2$); 6.95 (m, 2H, Ar); 7.31 (m, 1H, Ar).

NMR Compound 12/234 (CDCl$_3$, 400 MHz, δ in ppm): 1.47 (s, 3H, CH$_3$); 1.51 (s, 3H, CH$_3$); 3.13 (d, 1H, CH$_2$); 3.25 (d, 1H, CH$_2$); 4.48 (d, 1H, S(O)CH$_2$); 4.54 (d, 1H, S(O)CH$_2$); 7.04 (m, 1H, Ar); 7.28 (m, 2H, Ar).

NMR Compound 32/254 (CDCl$_3$, 400 MHz, δ in ppm): 1.47 (s, 3H, CH$_3$); 1.53 (s, 3H, CH$_3$); 3.21 (d, 1H, CH$_2$); 3.27 (d, 1H, CH$_2$); 4.69 (br s, 2H, S(O)CH$_2$); 7.23 (t, 1H, Ar); 7.37 (d, 2H, Ar).

Compounds of the Formula (Ib) (Racemates)

(Ib)

| Ex. No. | R$^6$ | R$^7$ | R$^8$ |
|---|---|---|---|
| 483/664 | CF$_3$ | Me | OCHF$_2$ |
| 610/791 | CF$_3$ | Me | CF$_3$ |

NMR Compound 483/664 (CDCl$_3$, 400 MHz): 1.50 (s, 3H, CH$_3$); 1.52 (s, 3H, CH$_3$); 3.04 (d, 1H, CH$_2$); 3.17 (d, 1H, CH$_2$); 3.84 (s, 3H, NCH$_3$); 4.15 (br s, 2H, S(O)CH$_2$); 6.94 (dd, 1H, OCHF$_2$).

NMR Compound 610/791 (CDCl$_3$, 400 MHz, δ in ppm): 1.47 (s, 3H, CH$_3$); 1.52 (s, 3H, CH$_3$); 3.04 (d, 1H, CH$_2$); 3.20 (d, 1H, CH$_2$); 4.09 (s, 3H); 4.30 (d, 1H, S(O)CH$_2$); 4.39 (d, 1H, S(O)CH$_2$).

B. FORMULATION EXAMPLES a) A dust is obtained by mixing 10 parts by weight of a compound of the formula (I) and 90 parts by weight of talc as inert substance and comminuting the mixture in a hammer mill.

b) A wettable powder which is readily dispersible in water is obtained by mixing 25 parts by weight of a compound of the formula (I), 64 parts by weight of kaolin-containing quartz as inert substance, 10 parts by weight of potassium lignosulfonate and 1 part by weight of sodium oleoylmethyltaurate as wetting agent and dispersant, and grinding the mixture in a pinned-disk mill.

c) A readily water-dispersible dispersion concentrate is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.) and grinding the mixture in a ball mill to a fineness of below 5 microns.

d) An emulsifiable concentrate is obtained from 15 parts by weight of a compound of the formula (I), 75 parts by weight of cyclohexanone as solvent and 10 parts by weight of oxethylated nonylphenol as emulsifier.

e) Water-dispersible granules are obtained by mixing

| | |
|---|---|
| 75 parts by weight | of a compound of the formula (I) |
| 10 parts by weight | of calcium lignosulfonate, |
| 5 parts by weight | of sodium lauryl sulfate, |
| 3 parts by weight | of polyvinyl alcohol and |
| 7 parts by weight | kaolin | grinding the mixture in a pinned-disk mill, and granulating the powder in a fluidized bed by spraying on water as granulating liquid.

f) Water-dispersible granules are also obtained by homogenizing and precomminuting

| | |
|---|---|
| 25 parts by weight | of a compound of the formula (I), |
| 5 parts by weight | of sodium 2,2'-dinaphthylmethane-6,6'-disulfonate, |
| 2 parts by weight | of sodium oleoylmethyltaurate, |
| 1 part by weight | of polyvinyl alcohol, |
| 17 parts by weight | calcium carbonate and |
| 50 parts by weight | of water | in a colloid mill, then grinding the mixture in a bead mill, and atomizing and drying the resulting suspension in a spray tower, using a single-fluid nozzle.

C. BIOLOGICAL EXAMPLES

1. Pre-emergence Herbicidal Effect and Crop Plant Compatibility

Seeds of monocotyledonous or dicotyledonous weed plants or crop plants are planted in wood-fiber pots in sandy loam and covered with soil. The compounds according to the invention, formulated in the form of wettable powders (WP), are then applied as aqueous suspension at a water application rate of 600 l/ha (converted) with the addition of 0.2% of wetting agent to the surface of the covering soil.

After the treatment, the pots are placed in a greenhouse and kept under good growth conditions for the test plants.

After about 3 weeks, the effect of the preparations is scored visually in comparison with untreated controls (herbicidal effect in percent (%): 100% activity=the plants have died, 0% activity=like control plants).

As shown by the results, the compounds according to the invention have good herbicidal pre-emergence activity against a broad spectrum of weed grasses and broad-leaved weeds. The compounds according to Examples 6, 32, 228, 254, 483, 664, 610, 791 and other compounds from Tables 1-4, for example, have very good herbicidal activity against harmful plants such as, for example, *Avena fatua, Stellaria media, Echinochloa crus-galli, Lolium multiflorum, Setaria viridis, Amaranthus retroflexus, Viola tricolor, Veronica persica* and *Alopecurus myosuroides* when applied by the pre-emergence method at an application rate of 0.32 kg and less of active substance per hectare.

In addition, some substances also spare monocotyledonous and dicotyledonous crops such as corn and oilseed rape. Some of the compounds according to the invention have high selectivity and are therefore suitable for controlling unwanted vegetation in agricultural crops by the pre-emergence method.

The following results were achieved with the compounds of the formula (Ia) by the pre-emergence method:

| Compound | Application rate | BRSNW | ALOMY | LOLMU | SETVI |
| --- | --- | --- | --- | --- | --- |
| 6 (S config.) | 320 g of active compound/ha | 0 | 100 | 100 | 100 |
| | 80 g of active compound/ha | 0 | 90 | 80 | 60 |
| Racemate of 6 (S config.) and 228 (R config.) | 320 g of active compound/ha | 30 | 100 | 80 | 40 |
| | 80 g of active compound/ha | 20 | 70 | 80 | 40 |
| 228 (R config.) | 320 g of active compound/ha | 0 | 80 | 0 | 50 |
| | 80 g of active compound/ha | 0 | 60 | 0 | 0 |

From the above table, it can be deduced that the (S) stereoisomers of the compounds of the formula (Ia) according to the invention have better herbicidal action against the weed grasses examined than the racemic mixture. At the same time, the crop compatibility of the (S) stereoisomers in oilseed rape is surprisingly high. In addition, the crop compatibility of the compound of the formula (Ia) having the (R) configuration is better than that of the racemate. With potent herbicidal activity, the (S) stereoisomer has better crop compatibility (selectivity) in the crop plant winter rape (SETVI). At an active compound application rate of 80 g of ai/ha, there is a marked difference in the activity S>rac>R.

The following results were achieved with the compounds of the formula (Ib) by the pre-emergence method:

| Compound | Application rate | BRSNW | ALOMY | LOLMU | SETVI |
| --- | --- | --- | --- | --- | --- |
| 483 (S config.) | 80 g of active compound/ha | 0 | 100 | 100 | 90 |
| | 20 g of active compound/ha | 0 | 80 | 60 | 80 |
| Racemate of 483 (S config.) and 664 (R config.) | 80 g of active compound/ha | 0 | 90 | 90 | 80 |
| | 20 g of active compound/ha | 0 | 0 | 0 | 40 |

From the above table, it can be deduced that the (S) stereoisomers of the compounds of the formula (Ib) according to the invention have better herbicidal action against the weed grasses examined than the racemic mixture. This is true in particular for the application rate of 20 g of active compound/ha.

At the same time, the crop compatibility of the (S) stereoisomers in oilseed rape is surprisingly high. It is particularly surprising that, at increased herbicidal activity, the crop compatibility can be maintained at a constant good level. Usually, crop compatibility (selectivity) decreases with improved herbicidal activity.

The following results were achieved with the compounds of the formula (Ib) by the pre-emergence method:

| Compound | Application rate | ZEAMX | ALOMY | POLCO | VERPE |
|---|---|---|---|---|---|
| 32 (S config.) | 80 g of active compound/ha | 0 | 100 | 80 | 100 |
|  | 20 g of active compound/ha | 0 | 80 | 40 | 40 |
| Racemate of 32 (S config.) and 254 (R config.) | 80 g of active compound/ha | 10 | 90 | 20 | — |
|  | 20 g of active compound/ha | 0 | 80 | — | 0 |
| 254 (R config.) | 80 g of active compound/ha | 0 | 60 | 20 | 20 |
|  | 20 g of active compound/ha | 0 | 0 | 10 | 0 |

From the above table, it can be deduced that the (S) stereoisomers of the compounds of the formula (Ib) according to the invention have better herbicidal action against the weed grasses examined than the racemic mixture.

At the same time, the crop compatibility of the (S) stereoisomers in corn (ZEAMX) is surprisingly high.

Abbreviations:
ALOMY *Alopecurus myosuroides* (black-grass)
LOLMU: *Lolium multiflorum* (Italian ryegrass)
SETVI: *Setaria viridis* (green foxtail)
BRSNW: *Brassica napus* (winter rape)
ZEAMX: *Zea mays* (corn)

2. Post-Emergence Herbicidal Effect and Crop Plant Compatibility

Seeds of monocotyledonous and dicotyledonous weed and crop plants are placed in sandy loam in wood fibre pots, covered with soil and cultivated in a greenhouse under good growth conditions. 2 to 3 weeks after sowing, the test plants are treated at the one-leaf stage. The compounds according to the invention, formulated in the form of wettable powders (WP), are then applied by spraying as aqueous suspension at a water application rate of 600 l/ha (converted) with the addition of 0.2% of wetting agent to the green parts of the plants. After the test plants have been kept in the greenhouse under optimum growth conditions for about 3 weeks, the activity of the preparations is rated visually in comparison to untreated controls (herbicidal activity in percent (%): 100% activity=the plants have died, 0% activity=like control plants).

As shown by the results, the compounds according to the invention have good herbicidal post-emergence activity against a plurality of weed grasses and broad-leaved weeds. The compounds Nos. 6, 32, 228, 254, 483, 664, 610 and 791 and other compounds from Tables 1-4, for example, have very good herbicidal activity against harmful plants such as, for example, *Avena fatua*, *Echinochloa crus-galli*, *Lolium multiflorum*, *Setaria viridis* and *Alopecurus myosuroides* when applied by the post-emergence method at an application rate of 0.32 kg and less of active substance per hectare.

In addition, some substances also spare monocotyledonous and dicotyledonous crops such as corn and oilseed rape. Some of the compounds according to the invention have high selectivity and are therefore suitable for controlling unwanted vegetation in agricultural crops by the post-emergence method.

The invention claimed is:

1. An optically active compound of the formula (I) in the form of its (s) stereoisomer, and/or an agrochemically acceptable salt and/or an agrochemically acceptable quaternized nitrogen derivative thereof

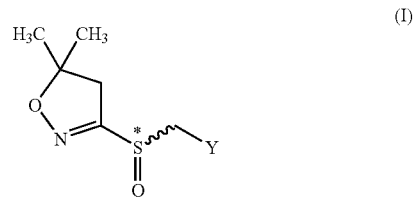

wherein
Y is

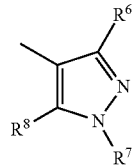

and
the individual substituents $R^6$ to $R^8$ are each independently of one another selected from the group consisting of
hydrogen, halogen, hydroxyl, cyano, nitro, amino, C(O)OH, formyl, ($C_1$-$C_6$)-alkyl, ($C_1$-$C_6$)-haloalkyl, ($C_1$-$C_6$)-alkylcarbonyl, ($C_1$-$C_6$)-haloalkylcarbonyl, ($C_1$-$C_6$)-alkylcarbonyloxy, ($C_1$-$C_6$)-haloalkylcarbonyloxy, ($C_1$-$C_6$)-alkylcarbonyl-($C_1$-$C_4$)-alkyl, ($C_1$-$C_6$)-haloalkylcarbonyl-($C_1$-$C_4$)-alkyl, ($C_1$-$C_6$)-alkylcarbonyl-($C_1$-$C_4$)-haloalkyl, ($C_1$-$C_6$)-haloalkylcarbonyl-($C_1$-$C_4$)-haloalkyl, ($C_1$-$C_6$)-alkoxy, ($C_1$-$C_6$)-haloalkoxy, ($C_1$-$C_6$)-alkoxycarbonyl, ($C_1$-$C_6$)-haloalkoxycarbonyl, ($C_1$-$C_6$)-alkoxycarbonyl-($C_1$-$C_6$)-alkyl, ($C_1$-$C_6$)-haloalkoxycarbonyl- ($C_1$-$C_6$)-alkyl, ($C_1$-$C_6$)-alkoxycarbonyl-($C_1$-$C_6$)-haloalkyl, ($C_1$-$C_6$)-haloalkoxycarbonyl-($C_1$-$C_6$)-haloalkyl, ($C_2$-$C_6$)-alkenyl, ($C_2$-$C_6$)-haloalkenyl, ($C_2$-$C_6$)-alkenylcarbonyl, ($C_2$-$C_6$)-haloalkenylcarbonyl, ($C_2$-$C_6$)-alkenyloxy, ($C_2$-$C_6$)-haloalkenyloxy, ($C_2$-$C_6$)-alkenyloxycarbonyl, ($C_2$-$C_6$)-haloalkenyloxycarbonyl, ($C_2$-$C_6$)-alkynyl, ($C_2$-$C_6$)-haloalkynyl, ($C_2$-$C_6$)-alkynylcarbonyl, ($C_2$-$C_6$)-haloalkynylcarbonyl, ($C_2$-$C_6$)-alkynyloxy, ($C_2$-$C_6$)-haloalkynyloxy, ($C_2$-$C_6$)-alkynyloxycarbonyl, ($C_2$-$C_6$)-haloalkynyloxycarbonyl, ($C_1$-$C_6$)-alkylthiocarbonyl, ($C_1$-$C_6$)-haloalkylthiocarbonyl, ($C_1$-$C_6$)-alkylthiocarbonyloxy, ($C_2$-$C_6$)-haloalkylthiocarbonyloxy, ($C_1$-$C_6$)-alkylthio-($C_1$-$C_6$)-alkoxy, ($C_1$-$C_6$)-alkylthio-($C_1$-$C_6$)-alkylcarbonyl, ($C_1$-$C_6$) -alkylthio-($C_1$-$C_6$)-alkylcarbonyloxy, ($C_6$-$C_{14}$)-aryl, ($C_6$-$C_{14}$)-aryloxy, ($C_6$-$C_{14}$)-arylcarbonyl, ($C_6$-$C_{14}$)-aryloxycarbonyl, ($C_6$-$C_{14}$)-aryl-($C_1$-$C_6$)-alkyl,($C_6$-$C_{14}$)-aryloxy-($C_1$-$C_6$)-alkyl, ($C_6$-$C_{14}$)-aryl-($C_1$-$C_6$)-alkoxy, ($C_6$-$C_{14}$)-aryl-($C_1$-$C_6$)-alkylcarbonyl, ($C_6$-$C_{14}$)-aryl-($C_1$-$C_6$)-alkylcarbonyloxy, ($C_6$-$C_{14}$)-aryl-($C_1$-$C_6$)-alkoxycarbonyl, ($C_6$-$C_{14}$)-aryl-($C_1$-$C_6$)-alkoxycarbonyloxy, ($C_1$-$C_6$)-alkylsulfonyl, ($C_1$-$C_6$)-alkylthio, ($C_1$-$C_6$)-alkylsulfinyl, ($C_1$-$C_6$)-haloalkylsulfonyl, ($C_1$-$C_6$)-haloalkylthio, ($C_1$-$C_6$)-haloalkylsulfinyl, ($C_1$-$C_6$) -alkylsulfonyl-($C_1$-$C_6$)-alkyl, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-haloalkylsulfonyl-($C_1$-$C_6$)-alkyl, ($C_1$-$C_6$)-haloalkylthio-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-haloalkyl, ($C_1$-$C_6$)-alkylthio-($C_1$-$C_6$)-haloalkyl, ($C_1$-$C_6$)-alkylsulfinyl-($C_1$-$C_6$)-haloalkyl, ($C_1$-$C_6$)-haloalkylsulfonyl-($C_1$-$C_6$)-haloalkyl, ($C_1$-$C_6$)-haloalkylthio-($C_1$-$C_6$)-haloalkyl, ($C_1$-$C_6$)-haloalkylsulfinyl-($C_1$-$C_6$)-haloalkyl, ($C_1$-$C_6$)-alkylsulfonyloxy, ($C_1$-$C_6$)-haloalkylsulfonyloxy, ($C_4$-$C_{14}$)-arylsulfonyl, ($C_6$-$C_{14}$)-arylthio, ($C_6$-$C_{14}$)-arylsulfinyl, mono-(($C_1$-$C_6$)-alkyl)-amino, mono-(($C_1$-$C_6$)-haloalkyl)-amino, di-(($C_1$-$C_6$)-alkyl)-amino, di-(($C_1$-$C_6$)-haloalkyl)-amino, (($C_1$-$C_6$)-alkyl-($C_1$-$C_6$)-haloalkyl)-amino, N—(($C_1$-$C_6$)-alkanoyl)-amino, N—(($C_1$-$C_6$)-haloalkanoyl)-amino, aminocarbonyl-($C_1$-$C_6$)-alkyl, mono-($C_1$-$C_6$)-alkylaminocarbonyl-($C_1$-$C_6$)-alkyl, mono-(($C_1$-$C_6$)-alkyl)-aminocarbonyl, di-($C_1$-$C_6$)-alkylaminocarbonyl-($C_1$-$C_6$)-alkyl, ($C_1$-$C_6$)-alkoxy-($C_1$-$C_6$)-alkyl, ($C_1$-$C_6$)-alkoxy-($C_1$-$C_6$)-alkoxy, ($C_1$-$C_6$)-alkoxycarbonyl-($C_1$-$C_6$)-alkoxy, ($C_3$-$C_8$)-cycloalkyl, ($C_3$-$C_8$)-cycloalkoxy, ($C_3$-$C_8$)-cycloalkyl-($C_1$-$C_6$)-alkyl, ($C_3$-$C_8$)-cycloalkyl-($C_1$-$C_6$)-haloalkyl, ($C_3$-$C_8$)-cycloalkyl-($C_1$-$C_6$)-alkoxy, ($C_3$-$C_8$)-cycloalkyl-($C_1$-$C_6$)-haloalkoxy, ($C_3$-$C_8$)-cycloalkylcarbonyl, ($C_3$-$C_8$)-cycloalkoxycarbonyl, ($C_3$-$C_8$)-cycloalkyl-($C_1$-$C_6$)-alkylcarbonyl, ($C_3$-$C_8$)-cycloalkyl-($C_1$-$C_6$)-haloalkylcarbonyl, ($C_3$-$C_8$)-cycloalkyl-($C_1$-$C_6$)-alkoxycarbonyl, ($C_3$-$C_8$)-cycloalkyl-($C_1$-$C_6$)-haloalkoxycarbonyl, ($C_3$-$C_8$)-cycloalkylcarbonyloxy, ($C_3$-$C_8$)-cycloalkoxycarbonyloxy, ($C_3$-$C_8$)-cycloalkyl-($C_1$-$C_6$)-alkylcarbonyloxy, ($C_3$-$C_8$)-cycloalkyl-($C_1$-$C_6$)-haloalkylcarbonyloxy, ($C_3$-$C_8$)-cycloalkyl-($C_1$-$C_6$)-alkoxycarbonyloxy, ($C_3$-$C_8$)-cycloalkyl-($C_1$-$C_6$)-haloalkoxycarbonyloxy, ($C_3$-$C_8$)-cycloalkenyl, ($C_3$-$C_8$)-cycloalkenyloxy, ($C_3$-$C_8$)-cycloalkenyl-($C_1$-$C_6$)-alkyl, ($C_3$-$C_8$)-cycloalkenyl-($C_1$-$C_6$)-haloalkyl, ($C_3$-$C_8$)-cycloalkenyl-($C_1$-$C_6$)-alkoxy, ($C_3$-$C_8$)-cycloalkenyl-($C_1$-$C_6$)-haloalkoxy, ($C_3$-$C_8$)-cycloalkenylcarbonyl, ($C_3$-$C_8$)-cycloalkenyloxycarbonyl, ($C_3$-$C_8$)-cycloalkenyl-($C_1$-$C_6$)-alkylcarbonyl, ($C_3$-$C_8$)-cycloalkenyl-($C_1$-$C_6$)-haloalkylcarbonyl, ($C_3$-$C_8$)-cycloalkenyl-($C_1$-$C_6$)-alkoxycarbonyl, ($C_3$-$C_8$)-cycloalkenyl-($C_1$-$C_6$)-haloalkoxycarbonyl, ($C_3$-$C_8$)-cycloalkenylcarbonyloxy, ($C_3$-$C_8$)-cycloalkenyloxycarbonyloxy, ($C_3$-$C_8$)-cycloalkenyl-($C_1$-$C_6$)-alkylcarbonyloxy, ($C_3$-$C_8$)-cycloalkenyl-($C_1$-$C_6$)-haloalkylcarbonyloxy, ($C_3$-$C_8$)-cycloalkenyl-($C_1$-$C_6$)-alkoxycarbonyloxy, ($C_3$-$C_8$)-cycloalkenyl-($C_1$-$C_6$)-haloalkoxycarbonyloxy, ($C_3$-$C_8$)-cycloalkylthio, ($C_3$-$C_8$)-alkenylthio, ($C_3$-$C_8$)-cycloalkenylthio, ($C_3$-$C_6$)-alkynylthio, hydroxy-($C_1$-$C_6$)-alkyl, hydroxy-($C_1$-$C_6$)-alkoxy, cyano-($C_1$-$C_6$)-alkoxy, cyano-($C_1$-$C_6$)-alkyl, 3-oxetanyloxy, pyrimidinyl-2-yl and 4,6-dimethoxypyrimidinyl-2-yl, C(O)NR$^9$R$^{10}$ where R$^9$ and R$^{10}$ independently of one another are hydrogen, ($C_1$-$C_6$)-alkyl, ($C_3$-$C_6$)-cycloalkyl, ($C_1$-$C_6$)-haloalkyl, or where R$^9$ and R$^{10}$ together form a ($C_1$-$C_6$)-alkylene group which may contain one oxygen or sulfur atom or one or two amino or ($C_1$-$C_6$)-alkylamino groups, where the radicals mentioned may, if appropriate, be attached cyclically to one another, provided they are ortho to one another and/or two substituents ortho to one another together form a ($C_1$-$C_6$)-alkylene group which may contain one or more oxygen and/or sulfur atoms, where the ($C_1$-$C_6$)-alkylene group may be mono- or polysubstituted by halogen and the halogen substituents in question may be identical or different; and where the radicals cycloalkyl and aryl may be mono- or polysubstituted independently of one another.

2. The compound of the formula (I) as claimed in claim 1 wherein Y is

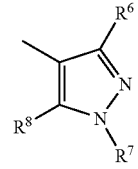

and the substituents R$^6$ and R$^8$ are independently of one another selected from the group consisting of hydrogen, halogen, hydroxyl, cyano, nitro, amino, ($C_1$-$C_4$)-alkyl, ($C_3$-$C_6$)-cycloalkyl, ($C_1$-$C_4$)-haloalkyl, ($C_1$-$C_4$)-alkoxy, ($C_1$-$C_4$)-alkoxy-($C_1$-$C_2$)-alkyl, ($C_3$-$C_6$)-cycloalkoxy, ($C_1$-$C_4$)-haloalkoxy, ($C_1$-$C_4$)-alkylthio , ($C_1$-$C_4$)-alkylthio-($C_1$-$C_2$)-alkyl, ($C_1$-$C_4$)-alkylsulfinyl, ($C_1$-$C_4$)-alkylsulfinyl-($C_1$-$C_2$)-alkyl, ($C_1$-$C_4$)-alkylsulfonyl, ($C_1$-$C_4$)-alkylsulfonyl-($C_1$-$C_2$)-alkyl, di-($C_1$-$C_4$)-alkylamino , ($C_2$-$C_4$)-alkenyl, ($C_2$-$C_4$)-alkynyl, ($C_3$-$C_4$)-alkenyloxy, ($C_3$-$C_4$)-alkynyloxy, ($C_3$-$C_6$)-cycloalkyl-($C_1$-$C_2$)-alkoxy, hydroxy-($C_1$-$C_2$)-alkyl, hydroxy-($C_1$-$C_2$)-alkoxy, cyano-($C_1$-$C_2$)-alkoxy, cyano-($C_1$-$C_2$)-alkyl, $C_6$-aryl, phenyl-($C_1$-$C_2$)-alkyl, phenyl-($C_1$-$C_2$)-alkoxy, $C_6$-aryloxy, ($C_1$-$C_4$)-alkylcarbonyloxy, ($C_3$ -$C_6$)- cycloalkyl-($C_1$-$C_2$)-alkyl, ($C_1$-$C_4$)-alkylcarbonyl-($C_1$-$C_2$)-alkyl, ($C_1$-$C_4$)-alkoxycarbonyl-($C_1$-$C_2$)-alkyl, aminocarbonyl-($C_1$-$C_2$)-alkyl and 3

-oxetanyloxy, —C(O)NR$^9$R$^{10}$, where R$^9$ and R$^{10}$ independently of one another are selected from the group consisting of hydrogen, (C$_1$-C$_6$)-alkyl, (C$_3$-C$_6$)-cycloalkyl, (C$_1$-C$_6$)-haloalkyl, or where R$^9$ and R$^{10}$ together form a (C$_1$-C$_6$)-alkylene group which may contain one oxygen or sulfur atom or one or two amino or (C$_1$-C$_6$)-alkylamino groups, or R$^8$ together with R$^7$ may form a radical —O(CH$_2$)$_3$O—,
where the radicals cycloalkyl and aryl may be mono- or polysubstituted independently of one another.

3. The compound of the formula (I) as claimed in claim 1 wherein Y is

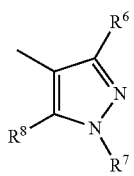

and R$^7$ is selected from the group consisting of hydrogen, (C$_1$-C$_4$)-alkyl, (C$_1$-C$_4$)-haloalkyl, C$_6$-aryl, phenyl-(C$_1$-C$_2$)-alkyl, (C$_3$-C$_6$)-cycloalkyl; (C$_3$-C$_6$)-cycloalkyl-(C$_1$-C$_2$)-alkyl, where the cycloalkyl radical is optionally substituted by (C$_1$-C$_4$)-alkyl; (C$_2$-C$_4$)-alkenyl, (C$_2$-C$_4$)-alkynyl, (C$_1$-C$_4$)-alkoxy-(C$_1$-C$_2$)-alkyl, (C$_1$-C$_4$)-alkylthio-(C$_1$-C$_2$)-alkyl, (C$_1$-C$_4$)-alkylsulfinyl-(C$_1$-C$_2$)-alkyl, cyano-(C$_1$-C$_2$)-alkyl, (C$_1$-C$_4$)-alkylsulfonyl-(C$_1$-C$_2$)-alkyl, (C$_1$-C$_4$)-alkoxycarbonyl-(C$_1$-C$_2$)-alkyl, aminocarbonyl-(C$_1$-C$_2$)-alkyl, mono-(C$_1$-C$_6$)-alkylaminocarbonyl-(C$_1$-C$_6$)-alkyl, mono-((C$_1$-C$_6$)-alkylaminocarbonyl, di-(C$_1$-C$_4$)-alkylaminocarbonyl-(C$_1$-C$_2$)-alkyl, hydroxy-(C$_1$-C$_4$)-alkyl, (C$_1$-C$_4$)-alkylcarbonyl-(C$_1$-C$_4$)-alkyl, (C$_1$-C$_4$)-alkoxycarbonyl-(C$_1$-C$_2$)-alkyl, (C$_1$-C$_4$)-alkylsulfonyl; phenylsulfonyl which is optionally substituted by one or more identical or different radicals from the group consisting of halogen, nitro, cyano, (C$_1$-C$_6$)-alkyl, (C$_1$-C$_6$)-haloalkyl, (C$_3$-C$_6$)-cycloalkyl, (C$_1$-C$_6$)-alkoxy, (C$_1$-C$_6$)-haloalkoxy, (C$_1$-C$_6$)-alkylcarbonyl, (C$_1$-C$_6$)-alkoxycarbonyl and (C$_1$-C$_6$)-alkylthio; (C$_1$-C$_4$)-alkylcarbonyl; phenylcarbonyl which is optionally substituted by one or more identical or different radicals from the group consisting of halogen, nitro, cyano, (C$_1$-C$_6$)-alkyl, (C$_1$-C$_6$)-haloalkyl, (C$_3$-C$_6$)-cycloalkyl, (C$_1$-C$_6$)-alkoxy, (C$_1$-C$_6$)-haloalkoxy, (C$_1$-C$_6$)-alkylcarbonyl, (C$_1$-C$_6$)-alkoxycarbonyl and (C$_1$-C$_6$)-alkylthio; pyrimidinyl-2-yl, 4,6-dimethoxypyrimidinyl-2-yl and (C$_1$-C$_4$)-alkoxycarbonyl; or R$^7$ together with R$^8$ may form a radical —O(CH$_2$)$_3$O—, where the radicals cycloalkyl and aryl may be mono- or polysubstituted independently of one another.

4. A process for preparing a compound of the formula (I) as claimed in claim 1, which comprises oxidizing a thioether of the formula (II)

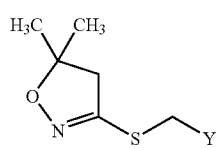

with one equivalent of an oxidizing agent to give a sulfoxide of the formula (I)

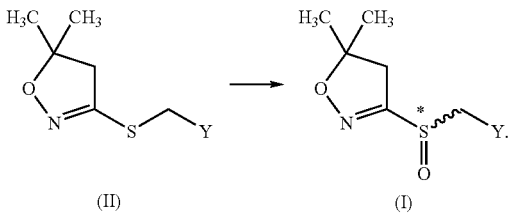

5. The process as claimed in claim 4 wherein the oxidizing agent is selected from the group consisting of hydrogen peroxide, sodium metaperiodate, organic peroxides and organic peracids.

6. A composition comprising at least one compound of the formula (I) as claimed in claim 1.

7. The composition as claimed in claim 6 wherein the composition comprises at least one further active compound selected from the group consisting of a further herbicide and at least one safener.

8. A plant growth regulator comprising a compound of the formula (I) as claimed in claim 1.

9. A plant growth regulator comprising a composition as claimed in claim 6.

10. A method for controlling plants in specific plant crops comprising applying a plant protection regulator as claimed in claim 8 to said crops.

11. The compound of formula (I) as claimed in claim 1, wherein R$^6$ is selected from the group consisting of H, F, Cl, Br, I, CN, OH, NH$_2$, NO$_2$, Me, Et, Pr, iPr, tBu, CHF$_2$, CF$_3$, Ph, OMe, OEt, OCHF$_2$ and OCH$_2$CF$_3$.

12. The compound of formula (I) as claimed in claim 1, wherein R$^6$ is selected from the group consisting of F, Cl, Br, CHF$_2$, CF$_3$, OCHF$_2$, OCF$_3$ and OCH$_2$CF$_3$.

13. The compound of formula (I) as claimed in claim 1, wherein R$^7$ is selected from the group consisting of H, Me, Et, Pr, cPr, iPr, Bu, iBu, sBu, tBu, cPen, cHex, CHF$_2$, CH$_2$CF$_3$, Ph, CH$_2$cPr, CH$_2$cPr(2-Me), CHMecPr, CH$_2$cBu, CH$_2$cPen, CH$_2$cHex, CH$_2$Ph, CH$_2$CH=CH$_2$, CH$_2$C≡CH, CHMeC≡CH, CH$_2$C≡CMe, CH$_2$OMe, CH$_2$OEt, CH$_2$CH$_2$OH, CH$_2$CH$_2$OMe, CH$_2$CH$_2$OEt, CH$_2$CH$_2$C(O)Me, CH$_2$SMe, CH$_2$SO$_2$Me, CH$_2$CN, CH$_2$C(O)OMe, CH$_2$C(O)OEt, CH$_2$C(O)NH$_2$, CH$_2$C(O)NMe$_2$, CH$_2$C(O)Me, SO$_2$Me, SO$_2$Ph, C(O)Me, C(O)Ph, C(O)OMe, Ph(2-Cl), Ph(3-Cl), Ph(4-Cl), Ph(4-OMe), Ph(4-Me), Ph(4-NO$_2$), Ph(4-CN) and Ph(4-C(O)OMe); or R$^7$ together with R$^8$ forms a radical
—O(CH$_2$)$_3$O—.

14. The compound of formula (I) as claimed in claim 1, wherein R$^7$ is selected from the group consisting of Me, Et and CHF$_2$.

15. The compound of formula (I) as claimed in claim 1, wherein R$^8$ is selected from the group consisting of H, F, Cl, Br, I, CN, OH, NH$_2$, NO$_2$, Me, Et, CHF$_2$, CF$_3$, OCHF$_2$, OCH$_2$CF$_3$, OMe, OEt, OPr, OiPr, OBu, OtBu, SO$_2$Me, SO$_2$iPr, 3-oxetanyloxy, OPh, OPh(2-Cl), OPh(3-Cl), OPh (4-Cl), OPh(3-OMe), OPh(4-Me), OPh(4-OMe), OCH$_2$CHF$_2$, OCH$_2$CN, OCH$_2$Ph, SEt, SO$_2$Et, SO$_2$Ph, NMe$_2$, OcHex, OCH$_2$Pr, OCH$_2$Pen, OCH$_2$cHex, OcPen, OC(O)Me, CH$_2$cPen, CH$_2$cHex, CH$_2$CH=CH$_2$, CH$_2$C≡CH, CHMeC≡CH, CH$_2$C≡CMe, CH$_2$OMe, CH$_2$OEt, CH$_2$CH$_2$OH, CH$_2$CH$_2$OMe, CH$_2$CH$_2$OEt, CH$_2$SMe, CH$_2$SO$_2$Me, OCH$_2$CH=CH$_2$ and OCH$_2$C≡CH.

16. The compound of formula (I) as claimed in claim 1, wherein $R^8$ is selected from the group consisting of F, Cl, $CHF_2$, $CF_3$, $OCHF_2$ and $OCH_2CF_3$.

17. A method for controlling plants in specific plant crops comprising applying the compound of formula (I) as claimed in claim 1 to said crops.

18. The method according to claim 17, wherein the compound is applied at a rate of 0.001 to 10 kg/ha.

19. The method according to claim 17, wherein the plant regulator is applied at a rate of 0.005 to 5 kg/ha.

* * * * *